(12) United States Patent
Leonhardt et al.

(10) Patent No.: US 11,185,691 B2
(45) Date of Patent: Nov. 30, 2021

(54) TUMOR THERAPY

(71) Applicant: LEONHARDT VENTURES LLC, Corona Del Mar, CA (US)

(72) Inventors: Howard J. Leonhardt, Playa Vista, CA (US); Jorge Genovese, Buenos Aires (AR)

(73) Assignee: LEONHARDT VENTURES LLC, Corona Del Mar, CA (US)

( * ) Notice: Subject to any disclaimer, the term of this patent is extended or adjusted under 35 U.S.C. 154(b) by 156 days.

(21) Appl. No.: 16/137,035

(22) Filed: Sep. 20, 2018

(65) Prior Publication Data
US 2019/0030330 A1  Jan. 31, 2019

Related U.S. Application Data

(63) Continuation-in-part of application No. 15/460,129, filed on Mar. 15, 2017, now Pat. No. 10,646,644.
(Continued)

(51) Int. Cl.
*A61N 1/36* (2006.01)
*A61N 1/08* (2006.01)
(Continued)

(52) U.S. Cl.
CPC .......... *A61N 1/36002* (2017.08); *A61N 1/08* (2013.01); *A61N 1/36017* (2013.01); *A61N 1/3629* (2017.08); *A61N 1/375* (2013.01)

(58) Field of Classification Search
CPC .. A61N 1/36002; A61N 1/08; A61N 1/36017; A61N 1/3629; A61N 1/375
See application file for complete search history.

(56) References Cited

U.S. PATENT DOCUMENTS

| D273,893 S | 5/1984 | Weitzman |
|---|---|---|
| 4,622,952 A | 11/1986 | Gordon |

(Continued)

FOREIGN PATENT DOCUMENTS

| CA | 2685161 A1 | 10/2007 |
|---|---|---|
| EP | 0603451 A1 | 6/1994 |

(Continued)

OTHER PUBLICATIONS

Zupan et al. "The relationship between osteoclastogenic and anti-osteoclastogenic pro-inflammatory cytokines differs in human osteoporotic and osteoarthritic bone tissues," Journal of Biomedical Science, 2012, 19:28 (DOI: 10.1186/1423-0127-19-28).
(Continued)

*Primary Examiner* — Mark W. Bockelman
(74) *Attorney, Agent, or Firm* — TraskBritt

(57) ABSTRACT

Described are a system and method that "reads" cancer tumors real time and custom delivers individualized bio-electric therapy to the patient. For example, the system reads a cancer tumor, and based upon this read, delivers to the subject "a confounding signal" to jam communication within that tumor. A cancer tumor may change its communication patterns and the therapy is designed to change with these patterns, attempting to always jam the relevant communication signaling pathway. The described system includes parameters not tied to communication jamming, which should also be customized to induce apoptosis to the cancer tumor. Such parameters include signals for starving a cancer tumor of blood supply and signals for changing the cancer tumor's surface proteins and/or charge so that the immune system attacks the cancer tumor.

20 Claims, 20 Drawing Sheets

Related U.S. Application Data

(60) Provisional application No. 62/454,521, filed on Feb. 3, 2017, provisional application No. 62/385,124, filed on Sep. 8, 2016, provisional application No. 62/375,271, filed on Aug. 15, 2016, provisional application No. 62/364,472, filed on Jul. 20, 2016, provisional application No. 62/363,012, filed on Jul. 15, 2016, provisional application No. 62/352,930, filed on Jun. 21, 2016, provisional application No. 62/308,702, filed on Mar. 15, 2016.

(51) Int. Cl.
*A61N 1/362* (2006.01)
*A61N 1/375* (2006.01)

(56) References Cited

U.S. PATENT DOCUMENTS

| | | |
|---|---|---|
| 4,976,733 A | 12/1990 | Girardot |
| 5,211,622 A | 5/1993 | Liboff et al. |
| 5,543,318 A | 8/1996 | Smith et al. |
| 5,693,029 A | 12/1997 | Leonhardt |
| 5,713,917 A | 2/1998 | Leonhardt et al. |
| 5,725,377 A | 3/1998 | Lemler et al. |
| 5,817,139 A | 10/1998 | Kasano |
| 5,957,949 A | 9/1999 | Leonhardt et al. |
| 6,344,052 B1 | 2/2002 | Greenan et al. |
| 6,618,625 B2 | 9/2003 | Silverstone |
| 6,957,106 B2 | 10/2005 | Schuler et al. |
| 6,988,004 B2 | 1/2006 | Kanno et al. |
| 7,029,276 B2 | 4/2006 | Mao |
| 7,136,699 B2 | 11/2006 | Palti |
| 7,341,062 B2 | 3/2008 | Chachques et al. |
| 7,483,749 B2 | 1/2009 | Leonhardt et al. |
| 7,686,799 B2 | 3/2010 | Leonhardt et al. |
| 7,881,784 B2 | 2/2011 | Pasricha et al. |
| 8,041,428 B2 | 10/2011 | Errico et al. |
| 8,133,267 B2 | 3/2012 | Leonhardt et al. |
| 8,166,976 B2 | 5/2012 | Webster et al. |
| 8,226,407 B2 | 7/2012 | Hanewinkel et al. |
| 8,465,533 B2 | 6/2013 | Palti |
| 8,639,361 B2 | 1/2014 | Nathanson |
| 8,656,930 B2 | 2/2014 | Schuler et al. |
| 8,660,669 B2 | 2/2014 | Nemeh et al. |
| 8,738,144 B2 | 5/2014 | Schneider |
| 8,909,346 B2 | 12/2014 | Chalmers |
| 8,945,104 B2 | 2/2015 | Boone et al. |
| 9,032,964 B2 | 5/2015 | Schuler et al. |
| 9,533,170 B2 | 1/2017 | Dye et al. |
| 9,545,331 B2 | 1/2017 | Ingemarsson-Matzen |
| D778,449 S | 2/2017 | Ingemarsson-Matzen |
| 9,656,096 B2 | 5/2017 | Pilla |
| 9,662,184 B2 | 5/2017 | Lowe |
| 9,687,383 B2 | 6/2017 | Ingemarsson-Matzen |
| 9,707,403 B2 | 7/2017 | Schuler |
| D832,447 S | 10/2018 | Wiffen |
| D881,399 S | 4/2020 | Ingemarsson-Matzen |
| 10,646,644 B2 | 5/2020 | Leonhardt et al. |
| 2002/0143373 A1 | 10/2002 | Courtnage et al. |
| 2003/0032998 A1 | 2/2003 | Altman |
| 2003/0220556 A1 | 11/2003 | Porat et al. |
| 2004/0010231 A1 | 1/2004 | Leonhardt et al. |
| 2004/0115587 A1 | 6/2004 | Breining et al. |
| 2004/0147906 A1 | 7/2004 | Voyiazis et al. |
| 2004/0236238 A1 | 11/2004 | Schuler et al. |
| 2005/0171578 A1 | 8/2005 | Leonhardt |
| 2006/0030908 A1 | 2/2006 | Powell et al. |
| 2006/0100553 A1 | 5/2006 | Lodin |
| 2007/0167984 A1 | 7/2007 | Kieval et al. |
| 2007/0190028 A1 | 8/2007 | Qu et al. |
| 2007/0265680 A1 | 11/2007 | Liu et al. |
| 2008/0227046 A1 | 9/2008 | Lowe et al. |
| 2008/0243060 A1 | 10/2008 | Hartmann et al. |
| 2010/0082027 A1 | 4/2010 | Chalmers |
| 2010/0184183 A1 | 7/2010 | Schussler et al. |
| 2012/0156648 A1 | 6/2012 | Kaufman et al. |
| 2013/0253413 A1 | 9/2013 | Levine et al. |
| 2014/0023983 A1 | 1/2014 | Lowe et al. |
| 2014/0214115 A1 | 7/2014 | Greiner et al. |
| 2014/0214116 A1 | 7/2014 | Peterson et al. |
| 2014/0214124 A1 | 7/2014 | Greiner et al. |
| 2014/0214144 A1 | 7/2014 | Peterson et al. |
| 2017/0028184 A1 | 2/2017 | Godden et al. |
| 2017/0036032 A1 | 2/2017 | Schuler et al. |
| 2017/0112983 A1 | 4/2017 | Thorne et al. |
| 2017/0266371 A1 | 9/2017 | Leonhardt et al. |
| 2017/0274206 A1 | 9/2017 | Leonhardt |
| 2018/0064935 A1 | 3/2018 | Leonhardt et al. |
| 2018/0071135 A1 | 3/2018 | Ingemarsson-Matzen |
| 2019/0015661 A1 | 1/2019 | Leonhardt et al. |
| 2019/0022389 A1 | 1/2019 | Leonhardt |
| 2019/0022396 A1 | 1/2019 | Leonhardt |
| 2020/0030136 A1 | 1/2020 | Hernandez |
| 2020/0289826 A1 | 9/2020 | Leonhardt |
| 2020/0324106 A1 | 10/2020 | Leonhardt |
| 2020/0330753 A1 | 10/2020 | Leonhardt et al. |

FOREIGN PATENT DOCUMENTS

| | | |
|---|---|---|
| JP | 2013-034881 A | 2/2013 |
| KR | 10-2007-0010908 A | 1/2007 |
| KR | 10-0726825 B1 | 6/2007 |
| WO | 92/17118 A1 | 10/1992 |
| WO | 2006/116728 A2 | 11/2006 |
| WO | 2007/146187 A2 | 12/2007 |
| WO | 2008/145724 A1 | 12/2008 |
| WO | 2009/021535 A1 | 2/2009 |
| WO | 2011/016629 A2 | 2/2011 |

OTHER PUBLICATIONS

Zhang et al. "Exosomes derived from human embryonic mesenchymal stem cells promote osteochondral regeneration", Osteoarthritis and Cartilage, vol. 24, Issue 12, Dec. 2016, pp. 2135-2140.

Yamakazi et al., "Hair cycle-dependent expression of hepatocyte growth factor (HGF) activator, other proteinases, and proteinase inhibitors correlates with the expression of HGF in rat hair follicles", J Investig Dermatol Symp Proc., 4(3):312-5 (Dec. 1999).

Yamaguchi, "RANK/RANKL/OPG during orthodontic tooth movement", Orthod Craniofac Res. May 2009; 12(2):113-9. doi: 10.1111/J.1601-6343.2009.01444.x.

What Is Elastin? http://www.keracyte.com/index.php/site/page?view=whatIsElastin.

Wei et al., "Epicardial FSTL1 reconstitution regenerates the adult mammalian heart," Nature 525: 479-485 (Sep. 24, 2015).

Walsh & Choi "Biology of the RANK* RAN* OPG System in Immunity, Bone, and Beyond", Front Immunol. 2014; 5:511.

W. Hoffmann, "Regeneration of the gastric mucosa and its glands from stem cells", Curr Med Chem, 15(29):3133-44 (2008).

Thattaliyath et al. "Modified Skeletal Myoblast Therapy for Cardiac Failure Using AAV SDF-1," Proc. Inti. Soc. Mag. Reson. Med. 16, p. 579 (2008).

Tamaki et al., "Cardiomyocyte Formation by Skeletal Muscle-Derived Multi-Myogenic Stem Cells after Transplantation into Infarcted Myocardium", PLoS One 3(3): e1789. doi:10.1371/journal.pone.0001789 (Mar. 2008).

Stenn et al., "Bioengineering the Hair Follicle," Organogenesis, 3(1): 6-13 (Jan.-Mar. 2007).

Spadari et al., Electrical stimulation enhances tissue reorganization during orthodontic tooth movement in rats; Clinical Oral Investigations, Jan. 2017, vol. 21, Issue 1, pp. 111-120, Abstract.

Signature Orthodontics "Accelerated Tooth Movement", http://www.sigortho.com/accelerated-tooth-movement, visited Mar. 15, 2017.

Seifi & Jeszri "Correlation of bone resorption induced by orthodontic tooth movement and expression of RANKL in rats", Dental Journal, vol. 26, No. 4 (2009).

Salcedo et al., "Low current electrical stimulation upregulates cytokine expression in the anal sphincter," Int. J. Colorectal Dis., Feb. 2012;27(2):221-5. doi: 10.1007/s00384-011-1324-3. Epub (Oct. 2011).

(56) References Cited

OTHER PUBLICATIONS

Sahoo and Losardo, "Exosomes and Cardiac Repair After Myocardial Infarction", Circulation Research, 114:333-344 (Jan. 16, 2014).
Robert Ferris, "Battle against baldness turns to stem cells" http://www.cnbc.com/2015/01/29/studies-indicate-its-possible-to-use-stem-cells-to-cure-baldness.html (Jan. 29, 2015).
Reversing Age-Related Hair Loss and Restoring Healthy Hair Growth in Men and Women https://nutritionreview.org/2015/08/reversing-age-related-hair-loss-and-restoring-healthy-hair-growth-in-men-and-women/ (Aug. 24, 2015).
R. Hamman "Modulation of RANKL and Osteoprotegerin in Adolescents Using Orthodontic Forces", Masters Thesis, University of Tennessee (2010).
Prochazka et al., "Cocktail of Factors from Fat-derived Stem Cells Shows Promise for Critical Limb Ischemia" http://www.sciencenewsline.com/news/2016012204520017.html (Jan. 21, 2016).
Prochazka et al. "Therapeutic Potential of Adipose-Derived Therapeutic Factor Concentrate for Treating Critical Limb Ischemia," Cell Transplantation, 25(9), pp. 1623-1633(11) (2016).
Park et al. "Effects of SM-215 on Hair Growth by Hair Follicle Stimulation", Indian Journal of Science and Technology, vol. 8(25), DOI: 10.17485/ijst/2015/v8i25/80263, (Oct. 2015).
P. Banerjee "Electrical muscle stimulation for chronic heart failure: an alternative tool for exercise training?" Curr Heart Fail Rep., 7(2):52-8. doi: 10.1007/s11897-010-0013-9 (Jun. 2010).
Our Approach to Improve Hair Loss by Increasing Hair Growth Factor IGF-1, http://www.jhgc.com.sg/theory/igf-1/index.html.
Otero et al. "Expression and Presence of OPG and RANKL mRNA and Protein in Human Periodontal Ligament with Orthodontic Force", Gene-Regulation-and-Systems-Biology, 2016, 10, 15-20.
Nimeri et al. "Acceleration of tooth movement during orthodontic treatment—a frontier in Orthodontics", Prog Orthod 2013; 14:42; DOI: 10.1186/2196-1042-14-42.
Mosteiro et al. "Tissue damage and senescence provide critical signals for cellular reprogramming in vivo." Science, 2016; 354 (6315): aaf4445 DOI: 10.1126/science.aaf4445.
Medtronic "Cardiac Resynchronization Therapy (CRT) Devices for Heart Failure" http://www.medtronic.com/us-en/patients/treatments-therapies/crt-devices.html.
Mass Device "Greatbatch wins FDA PMA for Algovita SCS" http://www.massdevice.com/greatbatch-wins-fda-pma-for-algovita-scs/ (Dec. 1, 2015).
Marie Ellis, "Cure for baldness? Stem cells bring hope" http://www.medicalnewstoday.com/articles/271898.php.
Li et al., "Exogenous IGF-1 promotes hair growth by stimulating cell proliferation and down regulating TGF-(Beta)1 in C57BL/6 mice in vivo" Growth Hormone & IGF Research, vol. 24, Issues 2-3, pp. 89-94 (Apr.-Jun. 2014).
Kim et al., The effects of electrical current from a micro-electrical device on tooth movement, http://e-kjo.org/search.php?where=aview&id=10.4041/kjod.2008.38.5.337& . . . visited Aug. 2, 2017.
Khan et al. "Accelerating Tooth Movement: What Options We Have?" J Dent Health Oral Disord Ther 2016, 5(7):00181.
Keles et al. "Inhibition of tooth movement by osteoprotegerin vs. pamidronate under conditions of constant orthodontic force", Eur J Oral Sci. Apr. 2007;115(2):131-6.
Kaur et al. "Electrically conductive polymers and composites for biomedical applications", RSC Adv., 2015,5, 37553-37567 DOI: 10.1039/C5RA01851J.
Kanzaki et al. "Periodontal ligament cells under mechanical stress induce osteoclastogenesis by receptor activator of nuclear factor kappaB ligand up-regulation via prostaglandin E2 synthesis", J Bone Miner Res 2002;17:21 / 220.
Kanzaki et al. "Local RANKL gene transfer to the periodontal tissue accelerates orthodontic tooth movement", Gene Therapy, (2006) 13, 678-685.
Kanzaki et al. "Local OPG gene transfer to periodontal tissue inhibits orthodontic tooth movement." J Dent Res 2004;83:92/ 925.
Kanno et al., Establishment of a Simple and Practical Procedure Applicable to Therapeutic Angiogenesis, Circulation, 1999, pp. 2682-2687, vol. 99.
K. Hart, Katherine A.nn D.D.S., "RANKL and Osteoprotegerin Levels in Response to Orthodontic Forces" (2012). Theses and Dissertations (ETD). Paper 107. http://dx.doi.org/10.21007/etd.cghs/012.0127.
Jia et al., "Activin B Promotes Initiation and Development of Hair Follicles in Mice" Cells Tissues Organs, 198:318-326 (Feb. 2014).
Jansen et al. "Stimulation of osteogenic differentiation in human osteoprogenitor cells by pulsed electromagnetic fields: an in vitro study" BMC Musculoskeletal Disorders (2010) 11:188 DOI: 10.1186/1471-2474-11-188.
Israeli innovation uses nerve stimulation to treat heart failure https://www.israel21c.org/israeli-innovation-uses-nerve-stimulation-to-treat-heart-failure/ (Feb. 11, 2007).
Involvement of hepatocyte growth factor/scatter factor and Met receptor signaling in hair follicle morphogenesis and cycling, FASEB J Feb. 2000 14:319-332.
Interesting study about prolactin, VEGF and angiogenic inhibition, http://www.regrowth.com/hair-loss-forums/topic/interesting-study-about-prolactin-vegf-and-angiogenic-inhibition/ (Nov. 2006).
Hy et al., "Insulin-like growth factor 1 and hair growth," Dermatol Online J,; 5(2):1 (Nov. 1999).
Hu Klein, "Vagus Nerve Stimulation: A new approach to reduce heart failure" Cardiology Journal (2010).
Hopkins Medicine "Overview of Pacemakers and Implantable Cardioverter Defibrillators (ICDs)," hopkinsmedicine.org/healthlibrary/conditions/cardiovascular_diseases/ )verview of pacemakers and implantable cardioverter defibrillators icds 85,P00234/, last visited Sep. 12, 2018.
Holding et al. "The correlation of RANK, RANKL and TNFa expression with bone loss volume and polyethylene wear debris around hip implants" Biomaterials 27(30):5212-9—Nov. 2006.
HN Sabbah "Electrical vagus nerve stimulation for the treatment of chronic heart failure", Cleve Clin J Med, 78 Suppl 1: S24-9. doi: 10.3949/ccjm.78.s1.04 (Aug. 2011).
Anne Trafton, "A Noninvasive Method for Deep Brain Stimulation," MIT News Office, (available at http://news.mit.edu/2017/noninvasive-method-deep-brain-stimulation-0601), (Jun. 1, 2017), 3 pages.
Aydin et al., "Focusing of Electromagnetic Waves by a Left-Handed Metamaterial Flat Lens," vol. 13, (2005), pp. 8753-8759.
Barker et al., "A Formidable Foe is Sabotaging Your Results: What You Should Know About Biofilms and Wound Healing," Plastic and Reconstructive Surgery, vol. 139, (2017), pp. 1184e-1194e.
Bioleohardnew, "Leonhardt Ventures Files Patent for Heart Valve Regeneration," (available at https://bioleonhardt.com/leonhardt-ventures-files-patent-for-heart-valve-regeneration/), (Mar. 20, 2018), 6 pages.
Borden et al., "Electric Current-Induced Detachment of *Staphylococcus epidermidis* Biofilms from Surgical Stainless Steel," Applied and Environmental Microbiology, vol. 70, (2004), pp. 6871-6874.
Cai et al., "Intermedin Inhibits Vascular Calcification by Increasing the Level of Matrix (Gamma)-Carboxyglutamic Acid Protein," Cardiovascular Research, vol. 85, (2010), pp. 864-873.
Canty et al., "Antibiotics Enhance Prevention and Eradication Efficacy of Cathodic-Voltage-Controlled Electrical Stimulation against Titanium-Associated Methicillin-Resistant *Staphylococcus aureus* and Pseudomonas aeruginosa Biofilms," mSphere, vol. 4, (May/Jun. 2019), e00178-19, 14 pages.
Caubet et al., "A Radio Frequency Electric Current Enhances Antibiotic Efficacy Against Bacterial Biofilms," Antimicrobial Agents and Chemotherapy, vol. 48, (2004), vol. 4662-4664.
Chen et al., "Deficiency in the Anti-Aging Gene Klotho Promotes Aortic Valve Fibrosis Through AMPK(Alpha)-Mediated Activation of RUNX2," Aging Cell, vol. 15, (Oct. 2016), pp. 853-860.
Chen et al., "The Role and Mechanism of (Alpha)-Klotho in the Calcification of Rat Aortic Vascular Smooth Muscle Cells," BioMed Research International, vol. 2015, (2015), 7 pages.
Chen et al., "The Strategy to Prevent and Regress the Vascular Calcification in Dialysis Patients," BioMed Research International, vol. 2017, (2017), 11 pages.

(56) References Cited

OTHER PUBLICATIONS

Chiang et al., "Silver-Palladium Surfaces Inhibit Biofilm Formation," Applied and Environmental Microbiology, vol. 75, (2009), pp. 1674-1678.
Costerton et al., "Mechanism of Electrical Enhancement of Efficacy of Antibiotics in Killing Biofilm Bacteria," Antimicrobial Agents and Chemotherapy, vol. 38, (1994), pp. 2803-2809.
Costerton et al., "The Application of Biofilm Science to the Study and Control of Chronic Bacterial Infections," The Journal of Clinical Investigation, vol. 112, (2003), pp. 1466-1477.
Delcaru et al., "Microbial Biofilms in Urinary Tract Infections and Prostatitis: Etiology, Pathogenicity, and Combating strategies," Pathogens, vol. 5, (2016), 12 pages.
Ehrlich et al., "Engineering Approaches for the Detection and Control of Orthopaedic Biofilm Infections," Clinical Orthopaedics and Related Research, vol. 437, (2005), pp. 59-66.
Froughreyhani et al., "Effect of Electric Currents on Antibacterial Effect of Chlorhexidine Against Entrococcus Faecalis Biofilm: An in Vitro Study," Journal of Clinical and Experimental Dentistry, vol. 10, (Dec. 2018), pp. e1223-e1229.
Giladi et al., "Microbial Growth Inhibition by Alternating Electric Fields," Antimicrobial Agents and Chemotherapy, vol. 52, (2008), pp. 3517-3522.
Golberg et al., "Eradication of Multidrug-Resistant A. Baumannii in Burn Wounds by Antiseptic Pulsed Electric Field," Technology, vol. 2, (2014), pp. 153-160.
Golberg et al., "Pulsed Electric Fields for Burn Wound Disinfection in a Murine Model," Journal of Burn Care & Research, vol. 36, (2015), pp. 7-13.
Hari et al., "Application of Bioelectric Effect to Reduce the Antibiotic Resistance of Subgingival Plaque Biofilm: An in Vitro Study," Journal of Indian Society of Periodontology, vol. 22, (2018), pp. 133-139.
Harkins et al., "Chitosan-Cellulose Composite for Wound Dressing Material. Part 2. Antimicrobial Activity, Blood Absorption Ability, and Biocompatibility," Journal of Biomedical Materials Research Part B, Applied biomaterials, vol. 102, (2014), 1199-1206.
HLeonhardt, Leonhardt Announces Vibrational Energy Device for Preventing Blood Clots Provisional Patent Application and License Agreements, (available at https://leonhardtventures.com/leonhardt-announces-vibrational-energy-device-preventing-blood-clots-provisional-patent-application-license-agreements/), (Jul. 5, 2017), 5 pages.
https://www.dicardiology.com/content/bioleonhardt-unveils-stem-pump Jan. 28, 2014.
Istanbullu et al., "Electrochemical Biofilm Control: Mechanism of Action," Biofouling, vol. 28, (2012), pp. 769-778.
Kasimanickam et al., "Prevention and Treatment of Biofilms by Hybrid- and Nanotechnologies," International journal of Nanomedicine, vol. 8, (2013), pp. 2809-2819.
Kim et al., "Effect of Electrical Energy on the Efficacy of Biofilm Treatment Using the Bioelectric Effect," NPJ Biofilms and Microbiomes, vol. 1, (2015), Article 15016, 8 pages.
Kinney et al., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine, vol. 51, (2019), pp. 40-46.
Lasserre et al., "Influence of Low Direct Electric Currents and Chlorhexidine Upon Human Dental Biofilms," Clinical and Experimental Dental Research, vol. 2, (Jul. 2016), pp. 146-154.
Lasserre et al., "Oral Microbes, Biofilms and Their Role in Periodontal and Peri-Implant Diseases," Materials, vol. 11, (Sep. 2018), Article 1802, 17 pages.
Lee et al. "Hepatocyte growth factor (HGF) activator expressed in hair follicles is involved in in vitro HGF-dependent hair follicle elongation," J. Dermatol. Sci., 25(2):156-63 (Feb. 2001).
Lee et al., "Targeted Release of Tobramycin From a pH-Responsive Grafted Bilayer Challenged With *S. aureus*," Biomacromolecules, vol. 16, (2015), pp. 650-659.

Lei et al., "Efficacy of Reversal of Aortic Calcification by Chelating Agents," Calcified Tissue International, vol. 93, (Nov. 2013), 15 pages.
Leibrock et al., "NH4Cl Treatment Prevents Tissue Calcification in Klotho Deficiency," Journal of the American Society of Nephrology, vol. 26, (2015), pp. 2423-2433.
Li, et al. "Local injection of RANKL facilitates tooth movement and alveolar bone remodelling." Oral Diseases, 25(2), 550-560. https://doi.org/10.1111/odi.13013.
Lop et al., Cutting-Edge Regenerative Medicine Technologies for the Treatment of Heart Valve Calcification, Calcific Aortic Valve Disease, (2013), (available at http://dx.doi.org/10.5772/55327), 57 pages.
McLean et al., "Training the Biofilm Generation-a Tribute to J. W. Costerton," Journal of Bacteriology, vol. 194, (Dec. 2012), pp. 6706-6711.
Miles et al. "Assessment of the changes in arch perimeter and irregularity in the mandibular arch during initial alignment with the AcceleDent Aura appliance vs no appliance in adolescents: A single-blind randomized clinical trial", Dec. 2016, vol. 150, Issue 6 American Journal of Orthodontics and Dentofacial Orthopedics (9 pages).
Nodzo et al., "Cathodic Electrical Stimulation Combined With Vancomycin Enhances Treatment of Methicillin-Resistant *Staphylococcus aureus* Implant-Associated Infections," Clinical Orthopaedics and Related Research, vol. 473, (2015), pp. 2856-2864.
Nodzo et al., "Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), 1668-1675.
Novickij et al., "Induction of Different Sensitization Patterns of MRSA to Antibiotics Using Electroporation," Molecules, vol. 23,(2018), Article 1799, 10 pages.
O'Neill et al., "Recent Progress in the Treatment of Vascular Calcification," Kidney International, vol. 78, (Dec. 2010), pp. 1232-1239.
Palza et al., "Electroactive Smart Polymers for Biomedical Applications," Materials, vol. 12, (2019), 24 pages.
Pozo et al., "Bioelectric Effect and Bacterial Biofilms. A Systematic Review," The International Journal of Artificial Organs, vol. 31, (2008), pp. 786-795.
Pozo et al., "Effect of Electrical Current on the Activities of Antimicrobial Agents Against Pseudomonas Aeruginosa, *Staphylococcus aureus*, and *Staphylococcus epidermidis* Biofilms," Antimicrobial Agents and Chemotherapy, vol. 53, (2009), pp. 35-40.
Pozo et al., "Prevention of *Staphylococcus epidermidis* Biofilm Formation Using Electrical Current," Journal of Applied Biomaterials & Functional Materials, vol. 12, (2014), pp. 81-83.
Pozo et al., "The Electricidal Effect: Reduction of *Staphylococcus* and Pseudomonas Biofilms by Prolonged Exposure to Low-Intensity Electrical Current," Antimicrobial Agents and Chemotherapy, vol. 53, (2009), pp. 41-45.
Ren et al., "Efficient Eradication of Mature Pseudomonas Aeruginosa Biofilm via Controlled Delivery of Nitric Oxide Combined with Antimicrobial Peptide and Antibiotics," Frontiers in Microbiology, vol. 7, Article 1260, (Aug. 2016), 8 pages.
Roy et al., "Disposable Patterned Electroceutical Dressing (PED-10) Is Safe for Treatment of Open Clinical Chronic Wounds," Advances in Wound Care, vol. 8, (1019), pp. 149-159.
Hearts build new muscle with this simple protein patch, jacobsschool.ucsd.edu/news/news_releases/release.sfe?id=1813 (Sep. 16, 2015).
Hair Growth Factors, Nanogen, http://www.svijet-kose.com/dokumenti/Serum-vegf.pdf.
Giganti et al. "Changes in serum levels of TNF-alpha, IL-6, OPG, RANKL and their correlation with radiographic and clinical assessment in fragility fractures and high energy fractures", J Biol Regul Homeost Agents, Oct.-Dec. 2012; 26(4):671-80.
Fukuoka et al., "The Latest Advance in Hair Regeneration Therapy Using Proteins Secreted by Adipose-Derived Stem Cells" The American Journal of Cosmetic Surgery, 29(4):273-282 (2012).
Fukuoka and Suga, "Hair Regeneration Treatment Using Adipose-Derived Stem Cell Conditioned Medium: Follow-up With Trichograms" Eplasty, 15:e10 (Mar. 2015).

(56) References Cited

OTHER PUBLICATIONS

FDA Approves Algovita Spinal Cord Stimulation System from Greatbatch, http://www.odtmag.com/contents/view_breaking-news/2015-12-02/fda-approves-algovita-spinal-cord-stimulation-system-from-greatbatch (Dec. 2, 2015).
Electrical brain stimulation could support stroke recovery https://www.sciencedaily.com/releases/2016/03/160316151108.htm (Mar. 16, 2016).
Electric Tumor Treatment Fields, No. 0827 Policy, http://www.aetna.com/cpb/medical/data/800_899/0827.html (Nov. 18, 2016).
Elastatropin(Registered) in Scalp & Hair Conditioning https://www.proteingenomics.com/haircare.html.
Dong-Hwan Kim et al., The effects of electrical current from a micro-electrical device on tooth movement, Korean Orthod., Oct. 2008, 38(5):337-346.
Dibart et al. "Tissue response during Piezocision-assisted tooth movement: a histological study in rats", Eur J Orthod (2014) 36 (4): 457-464; DOI: https://doi.org/10.1093/ejo/cjt079.
D. Grad, "Electrical Scalp Device Can Slow Progression of Deadly Brain Tumors", New York Times, https://www.nytimes.com/2014/11/16/health/electrical-scalp-device-can-slow-progression-of-deadly-brain-tumors.html?_r=0 (Nov. 15, 2014).
d'Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.org/10.1155/2013/105873.
Control of pelage hair follicle development and cycling by complex interactions between follistatin and activin, FASEB J (Jan. 2, 2003).
Control of Hair Growth by a Growth Factor Protein, http://www.hairloss-reversible.com/control-of-hair-growth-by-a-growth-factor-protein/.
Columbia "Implant Procedure Concepts—Pacemaker, ICD and CRT Overview," columbia.edu/itc/hs/medical/hickey/docs/Pacemaker,%20ICD%20and%20CRT%200verview%20022007.pdf, last risited Sep. 12, 2018.
Chen et al., "Regenerative Hair Waves in Aging Mice and Extra-Follicular Modulators Follistatin, Dkk1, and Sfrp4," Journal of Investigative Dermatology, Aug. 2014, vol. 134, Issue 8, pp. 2086-2096.
Chemet & Levin, "Transmembrane voltage potential is an essential cellular parameter for the detection and control of tumor development in a Xenopus model," Dis. Models & Mech. 6, pp. 595-607 (2013); doi:10.1242/dmm.010835.
Chang et al. Effect of Pulse-Burst Electromagnetic Field Stimulation on Osteoblast Cell Activities; Bioelectromagnetics 25:457-465 (2004).
Chang et al. "Pulsed electromagnetic fields stimulation affects osteoclast formation by modulation of osteoprotegerin, RANK ligand and macrophage colony-stimulating factor", Journal of Orthopaedic Research, 23 (2005) 1308-1314.
Cerrada et al. "Hypoxia-Inducible Factor 1 Alpha Contributes to Cardiac Healing in Mesenchymal Stem Cells-Mediated Cardiac Repair," Stem Cells and Development, 22(3): 501-511 (2013).
Bradshaw et al. "Designer self-assembling hydrogel scaffolds can impact skin cell proliferation and migration" Nature Scientific Reports, vol. 4, Article No. 6903 (2014).
Blood Vessels Hold Key to Thicker Hair Growth, https://www.sciencedaily.com/releases/2001/02/010215074636.htm(Feb. 2001).
Bio-Leonhardt "Micro Stimulator" http://www.bioleonhardt.com/micro-stimulator/.
Barbault et al., Amplitude-modulated electromagnetic fields for the treatment of cancer: Discovery of tumor-specific frequencies and assessment of a novel therapeutic approach, Journal of Experimental & Clinical Cancer Research, Apr. 14, 2009, vol. 28, No. 51, doi:10.1186/1756-9966-28-51, 10 pages.
B. Borgobello "FDA approves the treatment of brain tumors with electrical fields," New Atlas, http://newatlas.com/treatment-of-brain-tumors-with-electrical-fields/21433/(Feb. 13, 2012), last visited Sep. 12, 2018.

Almpani et al., "Nonsurgical Methods for the Acceleration of the Orthodontic Tooth Movement", Tooth Movement. Fronl Oral Biol., vol. 18, pp. 80-91 (Karger, Basel, CH 2016) (DOI:10.1159/000382048), Published online: Nov. 24, 2015.
Alice Park, "Shrinking Stem Cells Are the Real Reason for Hair Loss" Time, (Feb. 5, 2016).
"FDA Approves Algovita Spinal Cord Stimulation System from Greatbatch," http://www.odtmag.com/contents/view_breaking-news/2015-12-02/fda-approves-algovita-spinal-cord-stimulation-jystem-from-greatbatch (Dec. 2, 2015).
"Electrical brain stimulation could support stroke recovery," sciencedaily.com/releases/2016/03/160316151108.htm (Mar. 16, 2016), last visited Sep. 12, 2018.
"Electric Tumor Treatment Fields," No. 0827 Policy, aetna.com/cpb/medical/data/800_899/0827.html (Nov. 18, 2016), last visited Sep. 12, 2018.
Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.org/10.1155/2013/105873.
Sandvik et al., "Direct Electric Current Treatment under Physiologic Saline Conditions Kills *Staphylococcus epidermidis* Biofilms via Electrolytic Generation of Hypochlorous Acid," PloS one, vol. 8, (Feb. 2013), e55118, 14 pages.
Schmidt-Malan et al., "Activity of Fixed Direct Electrical Current in Experimental *Staphylococcus aureus* Foreign-Body Osteomyelitis," Diagnostic Microbiology and Infectious Disease, vol. 93, (2019), pp. 92-95.
Scott Jeffrey, "How to Decalcify Your Pineal Gland (and Why It's Really Important for Higher Mental Performance)," (available at https://scottjeffrey.com/decalcify-your-pineal-gland/), Retrieved on May 23, 2019, 23 pages.
Shahid et al., "Rhinosinusitis in Children," ISRN Otolaryngology, vol. 2012, Article ID 851831, (Dec. 2012), 11 pages.
Sharon M Moe, "Klotho: A Master Regulator of Cardiovascular Disease?," Circulation, vol. 125, (2012), pp. 2181-2183.
Shirtliff et al., "Assessment of the Ability of the Bioelectric Effect to Eliminate Mixed-Species Biofilms," Applied and Environmental Microbiology, vol. 71, (2005), pp. 6379-6382.
Shoji-Matsunaga et al. "Osteocyte regulation of orthodontic force-mediated tooth movement via RANKL expression." Scientific Reports, 7: 8753, published online Aug. 18, 2017 DOI:10.1038/s41598-017-09326-7.
Somayaji et al., "In Vitro Scanning Electron Microscopic Study on the Effect of Doxycycline and Vancomycin on Enterococcal Induced Biofilm," Iranian Endodontic Journal, vol. 5, (2010), pp. 53-58.
Souli et al., "Effects of Slime Produced by Clinical Isolates of Coagulase-Negative *Staphylococci* on Activities of Various Antimicrobial Agents," Antimicrobial Agents and Chemotherapy, vol. 42, (Apr. 1998), pp. 939-941.
Stewart et al., "Electrolytic Generation of Oxygen Partially Explains Electrical Enhancement of Tobramycin Efficacy Against Pseudomonas Aeruginosa Biofilm," Antimicrobial Agents and Chemotherapy, vol. 43, (1999), pp. 292-296.
Stoodley et al., "Influence of Electric Fields and pH on Biofilm Structure as Related to the Bioelectric Effect," Antimicrobial Agents and Chemotherapy, vol. 41, (1997), pp. 1876-1879.
Sultana et al., "Electrochemical Biofilm Control: A Review," Biofouling, vol. 31, (2015), pp. 745-758.
Szkotak et al., "Differential Gene Expression to Investigate the Effects of Low-Level Electrochemical Currents on Bacillus subtilis," AMB Express, vol. 1, (Nov. 2011), 12 pages.
Vinod Krishnan, Ze'ev Davidovitch (eds.), Biological Mechanisms of Tooth Movement, (John Wiley & Sons 2015 (10 Pages)).
Wang et al., "Controlling *Streptococcus* Mutans and *Staphylococcus aureus* Biofilms With Direct Current and Chlorhexidine," AMB Express, vol. 7, (Nov. 2017), 9 pages.
Wellman et al., "Bacterial Biofilms and the Bioelectric Effect," Antimicrobial Agents and Chemotherapy, vol. 40, (1996), pp. 2012-2014.
Wong et al., "Dual Functional Polyelectrolyte Multilayer Coatings for Implants: Permanent Microbicidal Base With Controlled Release

(56) References Cited

OTHER PUBLICATIONS of Therapeutic Agents," Journal of the American Chemical Society, vol. 132, (2010), pp. 17840-17848.

Wu et al., "Vascular Calcification: an Update on Mechanisms and Challenges in Treatment," Calcified Tissue International, vol. 93, (Oct. 2013), pp. 365-373.

Yang Lei, "Mechanisms and Reversal of Elastin Specific Medial Arterial Calcification" (2014). All Dissertations, Paper 1307, (available at https://tigerprints.clemson.edu/all_dissertations/1307), 214 pages.

Yarbrough et al., "Specific Binding and Mineralization of Calcified Surfaces by Small Peptides," Calcified Tissue International, vol. 86, (2010), pp. 58-66.

Zalavras, Charalampos G. "CORR Insights(Registered): Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), pp. 1676-1678.

Zhang et al., "Highly Stable and Reusable Imprinted Artificial Antibody Used for in Situ Detection and Disinfection of Pathogens," Chemical Science, vol. 6, (2015), pp. 2822-2826.

Wagenseil et al., "Elastin in large artery stiffness and hypertension," Journal of Cardiovascular Translational Research, vol. 5, No. 3, 2012, pp. 264-273, Available online at < https://www.ncbi.nlm.nih.gov/pmc/articles/PMC3383658/ >, 21, pages.

Stein et al., "The effect of transcutaneous electrical nerve stimulation on blood pressure," Blood Pressure, vol. 22, Issue 3, 2013, available online at < https://www.tandfonline.com/doi/full/10.3109/08037051.2012.722271 >, 5 pages.

Schardong et al., "Intradialytic neuromuscular electrical stimulation reduces DNA damage in chronic kidney failure patients: a randomized controlled trial," Biomarkers, vol. 23, Issue 5, 2018, pp. 1-11.

Niiranen et al., "Relative Contributions of Arterial Stiffness and Hypertension to Cardiovascular Disease: The Framingham Heart Study," Journal of the American Heart Association, vol. 5, No. 11, 2016, 8 pages.

Leonhardt's Launchpads Announces Filing of Patent for Bioelectric Stimulation Controlled Klotho Expression—Powerful Anti-aging and Regeneration Promoting Protein, by API Podder, Published: Mar. 13, 2019, available online at < https://mysocialgoodnews.com/leonhardts-launchpads-announces-filing-of-patent-for-bioelectric-stimulation-controlled-klotho-expression-powerful-anti-aging-and-regeneration-promoting-protein/.

Abstract of Zhang et al., "Comparison of arterial stiffness in non-hypertensive and hypertensive population of various age groups," Jan. 24, 2018, 2 pages.

Abstract of Sabino-Carvalho et al., "Non-invasive Vagus Nerve Stimulation Acutely Improves Blood Pressure Control in a Placebo Controlled Study," The FASEB Journal, vol. 31, 2017, available online at < https://www.fasebj.org/doi/abs/10.1096/fasebj.31.1_supplement.848.8 >, 2 pages.

Abstract of Collette et al., "Measurement of the local aortic stiffness by a non-invasive bioelectrical impedance technique," in Medical & Biological Engineering, vol. 49, No. 4, Feb. 2011, pp. 431-439, Available online at < https://www.ncbi.nlm.nih.gov/pubmed/21286830 >, 1 page.

Alghatrif et al. "The Conundrum of Arterial Stiffness, Elevated blood pressure, and Aging" Curr Hypertens Rep. Feb. 2015; 17(2): 12. doi: 10.1007/s11906-014-0523-z.

Andersson et al. "Drinking, antidiuresis and milk ejection from electrical stimulation within the hypothalamus of the goat," Acta Physiol Scand. Dec. 31, 1955; 35(2):191-201; DOI: 10.1111/j.1748-1716.1955.tb01277.x.

Ando et al. "RANKL/RANK/OPG; key therapeutic target in bone oncology" Curr Drug Discov Technol. Sep. 2008; 5(3): 263-268.

Aronowitz et al. "Mechanical versus enzymatic isolation of stromal vascular fraction cells from adipose tissue" SpringerPlus (2015) 4:713 DOI 10.1186/s40064-015-1509-2.

Atkinson et al. "Bioelectric Properties of the Tooth" 1969 vol. 48 issue: 5, pp. 789-794.

Aubert et al. "A new ultrasonic process for a renewal of aortic valve decalcification" Cardiovascular Ultrasound 2006, 4:2 doi:10.1186/1476-7120-4-2.

Back et al. "Endogenous Calcification Inhibitors in the Prevention of Vascular Calcification: A Consensus Statement From the COST Action EuroSoftCalcNet" Frontiers in Cardiovascular Medicine | www.frontiersin.org, Jan. 2019 | vol. 5 | Article 196.

Bang et al., "Attenuation of Hypertension by C-Fiber Stimulation of the Human Median Nerve and the Concept-Based Novel Device," Scientific Reports, vol. 8, (2018), 12 pages.

Beitelshees et al. "CXCL5 polymorphisms are associated with variable blood pressure in cardiovascular disease-free adults" Hum Genomics. 2012; 6(1): 9.

Berman "Suzanne Somers' Experimental Breast Reconstruction" Medpage Today, Feb. 7, 2012, www.medpagetoday.com > blogs > celebritydiagnosis.

Bi et al. "Key Triggers of Osteoclast-Related Diseases and Available Strategies for Targeted Therapies: A Review" Front Med (Lausanne). 2017; 4: 234. doi: 0.3389/fmed.2017.00234.

Boyle "Wound-Treating Jelly Regenerates Fresh, Scar-Free Skin", Popular Science, (Dec. 15, 2011), "New material developed for accelerated skin regeneration in major wounds", Science Highlight, (National Institute of Biomedical 11Imaging and Bioengineering, Dec. 17, 2015).

Brooks et al. "Bioelectric impedance predicts total body water, blood pressure, and heart rate during hemodialysis in children and adolescents" J. Ren Nutr., 18(3):304-311 (May 2008); doi: 10.1053/j.jrn.2007.11.008.

Buckle et al. "Soluble Rank Ligand Produced by Myeloma Cells Causes Generalised Bone Loss in Multiple Myeloma" PLoS One. 2012; 7(8): e41127. doi: 10.1371/journal.pone.0041127 PMCID: PMC3430669.

CalXStars Business Accelerator, Inc.—Website—Justia Patents—Mar. 15, 2017—US Patent Application for Stimulator, Pump & Composition Patent Application (Application #20170266371) https://protect-us.mimecast.com/s/tSaBCxkVIwuDr61CvMWbF?domain=patents.justia.com.

Chen et al. "Secreted Klotho Attenuates Inflammation-Associated Aortic Valve Fibrosis in Senescence-Accelerated Mice P1" Hypertension. 2018;71:877-885. DOI: 10.1161/HYPERTENSIONAHA. 117.10560.) Downloaded from http://ahajournals.org by on Apr. 24, 2020 (9 pages).

Chen et al., Efficacy and Safety of Acupuncture for Essential Hypertension: A Meta-Analysis, Medical Science Monitor, vol. 24, (2018), pp. 2946-2969.

Christouls et al. "Pathogenesis and Management of Myeloma Bone Disease" Expert Rev Hematol. 2009; 2(4):385-398.

Collins "Bioelectric Signals Can Be Used to Detect Early Cancer," Tufts News, http://now.tufts.edu/news-releases/bioelectric-signals-used-detect-early-cancer (Feb. 1, 2013).

Cowburn et al. "HIF isoforms in the skin differentially regulate systemic arterial pressure" Proc Natl Acad Sci U S A. Oct. 22, 2013; 110(43): 17570-17575.

Cross et al. "Milk Ejection following Electrical Stimulation of the Pituitary Stalk in Rabbits," Nature 166, 994-995 (Dec. 9, 1950); doi:10.1038/166994b0 (Abstract Only).

Dietrich et al. "Decalcification of the mitral annulus: surgical experience in 81 patients" Thorac Cardiovasc Surg. Oct. 2006;54(7):464-7 (Abstract Only).

El-Bialy et al. "Effect of Low Intensity Pulsed Ultrasound (LIPUS) on Tooth Movement and Root Resorption: A Prospective Multi-Center Randomized Controlled Trial" J. Clin. Med. 2020, 9, 804; doi:10.3390/jcm9030804.

Eurekalert, UCI Study Finds Acupuncture Lowers Hypertension by Activating Natural Opioids, Available Online at < https://www.eurekalert.org/pub_releases/2016-10/uoc-usf103116.php >, (2016), 2 pages.

Fan et al., "A Review on the Nonpharmacological Therapy of Traditional Chinese Medicine with Antihypertensive Effects," Evidence-Based Complementary and Alternative Medicine, vol. 2019, (2019), Article ID 1317842, 7 pages.

(56) References Cited

OTHER PUBLICATIONS

Fatemi et al. "Imaging elastic properties of biological tissues by low-frequency harmonic vibration" Proceedings of the IEEE, 91(10):1503-1519 (Oct. 2003).
Ferrucci, D. A. "Introduction to This is Watson'," in IBM Journal of Research and Development, vol. 56, No. 3.4, pp. 1:1-1:15, May-Jun. 2012. DOI: 10.1147/JRD.2012.2184356.
Fili et al. "Therapeutic implications of osteoprotegerin" Cancer Cell International vol. 9, Article No. 26 (2009).
Flachskampf et al., "Randomized Trial of Acupuncture to Lower Blood Pressure," Circulation, vol. 115, (2007), pp. 3121-3129.
Fonseca et al. "Electrical stimulation: Complementary therapy to improve the performance of grafts in bone defects?" Journal of Biomedical Materials Research Part B: Applied Biomaterials 2018 vol. 000b, Issue 0.
Goranov et al. "Bone Lesions in Multiple Myeloma—The OPG/RANK-ligand System" Folia Med (Plovdiv). 2004; 46(3): 5-11 (Abstract Only).
Goswami et al. "Osteoprotegerin rich tumor microenvironment: implications in breast cancer" Oncotarget. Jul. 5, 2016; 7(27): 42777-42791.
Greenwald "Pulse pressure and arterial elasticity" QJM: An International Journal of Medicine, vol. 95, Issue 2, 2002, pp. 107-112.
Guimarães-Camboa et al. "Redox Paradox: Can Hypoxia Heal Ischemic Hearts?" Cell, 39(4):392-394, (Nov. 21, 2016) DOI: http://dx.doi.org/10.1016/j.devcel.2016.11.007.
Gurbax et al. "Accelerated Orthodontic Tooth Movement: A Review" mod Res Dent. 1(2). MRD.000508. 2017. DOI: 10.31031/MRD.2017.01.000508.
HealthCMI, "Acupuncture Combats Hypertension in University of California Research," Available online at < https://www.healthcmi.com/Acupuncture-Continuing-Education-News/1688-acupuncture-c . . . >, (2016), 9 pages.
HealthCMI, "Acupuncture Controls Hypertension in Groundbreaking Trial," Available online at < https://www.healthcmi.com/Acupuncture-Continuing-Education-News/1804-acupuncture-c . . . >, (2017), 9 pages.
HealthCMI, "UC Irvine—Acupuncture Reduces Hypertension Confirmed," Available Online at < https://www.healthcmi.com/Acupuncture-Continuing-Education-News/1792-uc-irvine-acup . . . >, (2017), 6 pages.
Heart Valve Calcifications-Focused Ultrasound TherapyFocused Ultrasound Therapy; Research Paper Last Updated: Jan. 28, 2020, The Focused Ultrasound Foundation Newsletter (5 pages).
Holen et al. "Role of Osteoprotegerin (OPG) in Cancer" Clin Sci (Lond). Mar. 2006; 110(3):279-91. doi: 10.1042/CS20050175.
Hu et al. "Klotho Deficiency Causes Vascular Calcification in Chronic Kidney Disease" J Am Soc Nephrol. Jan. 2011; 22(1): 124-136.
Hu et al. "Exosomes derived from human adipose mesenchymal stem cells accelerates cutaneous wound healing via optimizing the characteristics of fibroblasts", Nature Scientific Reports, vol. 6, Article No. 32993 (2016).
Huang et al. "Myocardial transfection of hypoxia-inducible factor-1a and co-transplantation of mesenchymal stem cells enhance cardiac repair in rats with experimental myocardial infarction", Stem Cell Research & Therapy 5:22 (2014) DOI: 10.1186/scrt410.
Hudson et al. "Local delivery of recombinant osteoprotegerin enhances postorthodontic tooth stability" Calcif Tissue Int. Apr. 2012; 90(4):330-42. doi: 10.1007/s00223-012-9579-4.
Iglesias-Linares et al. "The use of gene therapy vs. corticotomy surgery in accelerating orthodontic tooth movement." Orthod Craniofac Res. Aug. 2011; 14(3):138-48. doi: 10.1111/j.1601-6343.2011.01519.x.
Infante et al. "RANKL/RANK/OPG system beyond bone remodeling: involvement in breast cancer and clinical perspectives" Journal of Experimental & Clinical Cancer Research (2019) 38:12. https://doi.org/10.1186/s13046-018-1001-2.
International Search Report for International Application No. PCT/US19/52288, dated Jan. 10, 2020, 11 pages.
International Search Report for International Application No. PCT/US2019/025177, dated Sep. 3, 2019, 3 pages.
International Written Opinion for International Application No. PCT/US19/52288, dated Jan. 10, 2020, 07 pages.
International Written Opinion for International Application No. PCT/US2019/025177, dated Sep. 3, 2019, 5 pages.
Beebe et al. "Bioelectric Applications for Treatment of Melanoma," Cancers (Basel). Sep. 2010; 2(3): 1731-1770, published online Sep. 27, 2010; doi: 10.3390/cancers20317.
Blum "Role of cytokines in heart failure," American Heart Journal, vol. 135, Issue 2, Feb. 1998, pp. 181-186; doi.org/10.1016/S0002-8703(98)70080-8.
Campbell et ali. "Electrical stimulation to optimize cardioprotective exosomes from cardiac stem cells" Med Hypotheses. Mar. 2016; 88:6-9. doi: 10.1016/j.mehy.2015.12.022. Epub Jan. 11, 2016.
Cervera "The interplay between genetic and bioelectrical signaling permits a spatial regionalisation of membrane potentials in model multicellular ensembles," Nature, Scientific Reports, Oct. 12, 2016 vol. 6, Article No. 35201 (2016).
Chernet et al. "Transmembrane voltage potential is an essential cellular parameter for the detection and control of the cancer tumor development in a Xenopus model," Dis. Models and Mech. 6, pp. 595-607 (2013); Doi:10.1242/dmm.010835.
Ciria et al., Antitumor effectiveness of different amounts of electrical charge in Ehrlich and fibrosarcoma Sa-37 tumors, BMC Cancer, Nov. 26, 2004, 10 pages, vol. 4, No. 87.
Corrigan et al. "Neurogenic inflammation after traumatic brain injury and its potentiation of classical inflammation", Journal of Neuroinflammation, 2016, 13:264; doi://doi.org/10.1186/s12974-016-0738-9.
Dai et al. "Nanosecond Pulsed Electric Fields Enhance the Antitumour Effects of the mTOR Inhibitor Everolimus against Melanoma," Scientific Reports vol. 7, Article No. 39597 (2017).
Deswal et al. "Cytokines and Cytokine Receptors in Advanced Heart Failure An Analysis of the Cytokine Database from the Vesnarinone Trial (VEST)," Circulation. 2001;103:2055-2059; ://doi.org/10.1161/01.CIR.103.16.2055.
Gavira et al. "Repeated implantation of skeletal myoblast in a swine model of chronic myocardial infarction," Eur. Heart J., 31(8): 1013-1021. doi: 10.1093/eurheartj/ehp342 (2010).
Gullestad et al. "Inflammatory cytokines in heart failure: mediators and markers," Cardiology. 2012;122(1):23-35. doi: 10.1159/000338166. Epub Jun. 12, 2012.
Hamzelou et al. "Cancer reversed in frogs by hacking cells' electricity with light," New Scientist This Week, Mar. 16, 2016.
Jing-Hong et al. "Electrochemical Therapy of Tumors" Hindawi Publishing Corporation, Conference Papers in Medicine, vol. 2013, Article ID 858319, 13 pages, http://dx.doi.org/10.1155/2013/858319.
Keunen et al. "Anti-VEGF treatment reduces blood supply and increases tumor cell invasion in glioblastoma," Proc. Natl. Acad. Sci. U. S. A. Mar. 1, 2011; 108(9): 3749-3754, published online Feb. 14, 2011; doi: 10.1073/pnas.1014480108.
Lanzetto et al. "Fundamental principles of an anti-VEGF treatment regimen: optimal application of intravitreal anti-vascular endothelial growth factor therapy of macular diseases," Graefes Arch. Clin. Exp. Ophthalmol. 2017; 255(7): 1259-1273 (published online May 19, 2017); doi: 10.1007/s00417-017-3647-4.
Liesz et al. "Editorial: Mechanisms of neuroinflammation and inflammatory neurodegeneration in acute brain injury" Front. Cell. Neurosci., 2015. doi://doi.org/10.3389/fncel.2015.00300.
Lobo-Silva et al. "Balancing the immune response in the brain: IL-10 and its regulation," Journal of Neuroinflammation, 13:297 (2016); doi.org/10.1186/s12974-016-0763-8.
Mann, "Innate Immunity and the Failing Heart: The Cytokine Hypothesis Revisited," Circ. Res. Mar. 27, 2015; 116(7): 1254-1268.
Matsumori, "Cytokines and Heart Failure: Pathophysiological Roles and Therapeutic Implications," Heart Failure, Springer, Tokyo; doi.org/10.1007/978-4-431-68331-5_3.
Meadows et al. "Anti-VEGF Therapies in the Clinic," Cold Spring Harb. Perspect. Med. Oct. 2012; 2(10): a006577: doi: 10.1101/cshperspect.a006577.

(56) References Cited

OTHER PUBLICATIONS

Mishra "Angiogenic neovessels promote tissue hypoxia," Proc. Natl. Acad. Sci. U. S. A. Sep. 20, 2016; 113(38): 10458-10460, published online Sep. 13, 2016; doi: 10.1073/pnas.1612427113.
Paulus "Cytokines and heart failure," Heart Fail. Monit. 2000; 1(2):50-6.
Pupo et al., Electrotherapy on Cancer: Experiment and Mathematical Modeling, Current Cancer Treatment—Novel Beyond Conventional Approaches, Prof. Oner Ozdemir (Ed.) ISBN: 978-953-307-397-2, InTech, Available from: http://www.intechopen.com/books/current-cancer-treatment-novel-beyond-conventional-approaches/electrotherapy-on-cancer-experiment-and-mathematical-modeling, 2011.
Puro et al "Bioelectric impact of pathological angiogenesis on vascular function," PNAS Aug. 30, 2016 113 (35) 9934-9939; published ahead of print Aug. 22, 2016 https://doi.org/10.1073/pnas.1604757113.
RFA (radiofrequency ablation), Swedish Medical Imaging, 2 pages, author unknown, undated.
Schimmel et al. "Neuroinflammation in traumatic brain injury: A chronic response to an acute injury" Brain Circ, 2017, 3(3):135-142.
Silvers et al. "The Bioelectric Code: Reprogramming Cancer and Aging from the Interface of Mechanical and Chemical Microenvironments," Front. Cell Dev. Biol., Mar. 6, 2018; doi.org/10.3389/fcell.2018.00021.
Ueland et al. "Inflammatory cytokines as biomarkers in heart failure," Clinica Chimica Acta, vol. 443, Mar. 30, 2015, pp. 71-77; doi.org/10.1016/j.cca.2014.09.001.
Xiong et al. "Current understanding of neuroinflammation after traumatic brain injury and cell-based therapeutic opportunities" Chin J Traumatol. Jun. 2018; 21(3): 137-151. doi: 10.1016/j.cjtee.2018.02.003.
Warner "Inflammation Adds to Blood Pressure Risks, High Blood Pressure and C-Reactive Protein May Trigger Heart Attack, Stroke" Art WebMD Health News (2003) 2 pages.
Welch "RGS2 Proteins Regulate Blood Pressure" JASN Nov. 2010, 21 (11) 1809-1810.
Yang "Effect RANKL Produced by Periodontal Ligament Cells on Orthodontic Tooth Movement" (2016) Dental Theses. Paper 13.
Yang et al., "Acupuncture for hypertension," Cochrane Database of Systematic Reviews, Available Online at <https://www.cochranelibrary.com/cdsr/doi/10.1002/14651858.CD008821.pub2/full>, (2018), 4 pages.
Yu et al. "Association between inflammation and systolic blood pressure in RA compared to patients without RA" Arthritis Research & Therapy vol. 20, Article No. 107 (2018).
Zaniboni et al. "Do electrical current and laser therapies improve bone remodeling during an orthodontic treatment with corticotomy?" Clin Oral Invest 23, 4083-4097 (2019). https://doi.org/10.1007/s00784-019-02845-9.
Zdzisinska et al. "RANK/RANKL i OPG w szpiczaku plazmocytowym [The role of RANK/RANKL and OPG in multiple myeloma]" Postepy Hig Med Dosw (Online). 2006; 60:471-482 (Abstract Only).
Zhao et al. "Local osteoprotegerin gene transfer inhibits relapse of orthodontic tooth movement." Am J Orthod Dentofacial Orthop. Jan. 2012; 141(1):30-40. doi: 10.1016/j.ajodo.2011.06.035.
Jouybar et al. "Enhanced Skin Regeneration by Herbal Extract-Coated Poly-L-Lactic Acid Nanofibrous Scaffold" Artif Organs. Nov. 2017; 41(11):E296-E307. doi: 10.1111/aor.12926 (Abstract Only).
Jung et al. "Prospective 1-Year Follow-Up Study of Breast Augmentation by Cell-Assisted Lipotransfer" Aesthetic Surgery Journal 2016, vol. 36(2) 179-190 © 2015 The American Society for Aesthetic Plastic Surgery, Inc.
Kido et al. "Hypoxia-Inducible Factor 1-Alpha Reduces Infarction and Attenuates Progression of Cardiac Dysfunction After Myocardial Infarction in the Mouse" JACC, vol. 46, Issue 11, Dec. 6, 2005, pp. 2116-2124. https://doi.org/10.1016/j.jacc.2005.08.045.

King et al. "Mechanical Decalcification of the Aortic Valve" 272 The Annals of Thoracic Surgery vol. 42 No. 3 Sep. 1986 (pp. 269-272).
Kondo et al. "Types of tooth movement, bodily or tipping, do not affect the displacement of the tooth's center of resistance but do affect the alveolar bone resorption" Angle Orthod Jul. 2017; 87(4):563-569.
Kose et al. "Citric acid as a decalcifying agent for the excised calcified human heart valves" Anadolu Kardiyol Derg 2008; 8: 94-8 (Eng Abstract).
Lamoureux et al. "Therapeutic Relevance of Osteoprotegerin Gene Therapy in Osteosarcoma: Blockade of the Vicious Cycle between Tumor Cell Proliferation and Bone Resorption" Cancer Res 1 2007 67(15):7308-7318; DOI: 10.1158/0008-5472.CAN-06-4130.
Landau et al. "Review: Proposed Methods to Improve the Survival of Adipose Tissue in Autologous Fat Grafting" Plast Reconstr Surg Glob Open. 2018;6(8):e1870. Published Aug. 3, 2018. doi:10.1097/GOX.0000000000001870.
Lei "Mechanisms and Reversal of Elastin Specific Medial Arterial Calcification" (2014). All Dissertations, Papei 1307, (available at https://tigerprints.clemson.edu/all_dissertations/1307), 214 pages.
Leonhardt "Leonhardt Adds HIF-1 Alpha to Estate of Bioelectric Controlled Release Regenerative Proteins" Press Release, Published Jun. 13, 2017.
Leonhardt, Leonhardt Announces Vibrational Energy Device for Preventing Blood Clots Provisional Patent Application and License Agreements, (available at https://leonhardtventures.com/leonhardt-announces-vibrational-energy-device-preventing-blood-clots-provisional-)atent-application-license-agreements/), (Jul. 5, 2017), 5 pages.
Li "Regulation of Renal Oxygenation and Blood Pressure" Art. Virginia Commonwealth University, Richmond, VA, United States (Abstract).
Li et al., "Long-Lasting Reduction of Blood Pressure by Electroacupuncture in Patients with Hypertension: Randomized Controlled Trial," Medical Acupuncture, vol. 27, No. 4, (2015), pp. 253-266.
Li et al., "Repetitive Electroacupuncture Attenuates Cold-Induced Hypertension through Enkephalin in the Rostral Ventral Lateral Medulla," Scientific Reports, vol. 6, (2016), 10 pages.
Li et al., "The Mechanism of Acupuncture in Treating Essential Hypertension: A Narrative Review," International Journal of Hypertension, vol. 2019, (2019), Article ID 8676490, 10 pages.
Liang et al. "Therapeutic effect of low-intensity pulsed ultrasound on temporomandibular joint injury induced by chronic sleep deprivation in rats" Am J Transl Res. 2019; 11(6): 3328-3340.
Longhurst et al. "Evidence-based blood pressure reducing actions of electroacupuncture: mechanisms and clinical application" Sheng Li Xue Bao. Oct. 25, 2017; 69(5): 587-597.
Malakhov et al. "Assessment of Efficacy of Non-Invasive Peripheral Transcutaneous Electrical Nerve Stimulation for Correction of Blood Pressure in Patients With Arterial Hypertension" Journal of Hypertension: Jul. 2019—vol. 37—Issue—p. e88-e89 doi: 10.1097/01.hjh.0000570296.70620.44.
Martin "Historically significant events in the discovery of RANK/RANKL/OPG" World J Orthop. Oct. 18, 2013; 4(4): 186-197. doi: 10.5312/wjo.v4.i4.186.
McBride et al. "Aortic valve decalcification" J Thorac Cardiovasc Surg. Jul. 1990;100(1):36-42; discussion 42-3 (Abstract Only).
McGrath "OPG/RANKL/RANK Pathway as a Therapeutic Target in Cancer" Journal of Thoracic Oncology, Sep. 2011 6(9): 1468-1473.
Nordstorm "Electrical Stimulation Blood Pressure Treatment Devices Market to Set Astonishing Growth by 2026" Art. Apr. 4, 2019 Gator Ledger.
Norton et al. "Bioelectric Perturbations of Bone: Research Directions and Clinical Applications" Angle Orthod (1984) 54 (1): 73-87.
Novack "Inflammatory osteoclasts, a different breed of bone eaters?" Arthritis Rheumatol. Dec. 2016; 68(12): 2834-2836. doi: 10.1002/art.39835.
Oranger et al. "Cellular Mechanisms of Multiple Myeloma Bone Disease" Clinical and Developmental Immunology vol. 2013, Article ID 289458, 11 pages http://dx.doi.org/10.1155/2013/289458.

(56) References Cited

OTHER PUBLICATIONS

Oyajobi "Multiple myeloma/hypercalcemia" Arthritis Research & Therapy vol. 9, Article No. S4 (2007).

Pierce et al. "Collection and characterization of amniotic fluid from scheduled C-section deliveries," Cell Tissue Bank, DOI 10.1007/s10561-016-9572-7 (Springer, 2012) and is available from Irvine Scientific.

Plumbing Today, "How to Remove Hard, White Mineral Deposits from Faucets/Showerheads," (available at https://plumbingtoday.biz/blog/how-to-remove-hard-white-mineral-deposits-from-faucets-showerheads), (Jul. 11, 2016), 4 pages.

Price et al. "Mitral Valve Repair is Feasible Following Extensive Decalcification and Reconstruction of the Atrioventricular Groove" J Heart Valve Dis. Jan. 2015;24(1):46-52 (Abstract Only).

Rachner et al. "Prognostic Value of RANKL/OPG Serum Levels and Disseminated Tumor Cells in Nonmetastatic Breast Cancer" Clin Cancer Res Feb. 15, 2019 (25) (4) 1369-1378; DOI: 10.1158/1078-0432.CCR-18-2482.

Raje et al. "Role of the RANK/RANKL Pathway in Multiple Myeloma" Clin Cancer Res 2019 25(1):12-20; DOI: 10.1158/1078-0432.CCR-18-1537.

Sahmeddini et al., "Electro-Acupuncture Stimulation at Acupoints Reduced the Severity of Hypotension During Anesthesia in Patients Undergoing Liver Transplantation," Journal of Acupuncture and Meridian Studies, vol. 5, Issue 1, (2012), pp. 11-14.

Sethi et al. "Aortic stiffness: pathophysiology, clinical implications, and approach to treatment" Integr Blood Press Control. 2014; 7: 29-34.

Showkatbakhsh et al. "Effect of Intra-Canal Direct Current Electric Stimulation on Orthodontic Tooth Movement: An Experimental Study in Canines" Journal of Dental School 2016; 34(3): 157-67.

Showkatbakhsh et al. "The effect of pulsed electromagnetic fields on the acceleration of tooth movement." World J Orthod. 2010 Winter;11(4):e52-6.

Sisay et al. "The RANK/RANKL/OPG system in tumorigenesis and metastasis of cancer stem cell: potential targets for anticancer therapy" Onco Targets Ther. 2017; 10: 3801-3810.

Spiridonov et al. "Effect of Transcutaneous Electrical Stimulation of Nerves on Blood Pressure and Blood Content of Neuropeptide CGRP and Nitric Oxide in Hypertensive Rats with Metabolic Disturbances" Bull Exp Biol Med (Feb. 2019) 166: 436-437.

Sutherland et al. "Prolonged electrical stimulation of the nipples evokes intermittent milk ejection in the anaesthetised lactating rat," Exp Brain Res. 1987;66(1):29-34.

Tajima et al. "HIF-1alpha is necessary to support gluconeogenesis during liver regeneration" Biochem Biophys Res Commun. Oct. 2, 2009; 387(4):789-94. doi: 10.1016/j.bbrc.2009.07.115. Epub Jul. 28, 2009.

Tan et al. "Bioelectric Perturbations in Orthodontic tooth movement" 2010 Journal of Dental Sciences & Research 1:1: pp. 41-49.

Tan et al., "Acupuncture Therapy for Essential Hypertension: a Network Meta-Analysis," Annals of Translational Medicine, vol. 7, (2019), pp. 1-12.

Tavlasoglu et al. "Is partial decalcification of posterior mitral annular bed logical in all mitral valve replacement procedures?" European Journal of Cardio-Thoracic Surgery 43 (2013) 449-450.

Tokyo Medical and Dental University "RANKL expressed by osteocytes has an important role in orthodontic tooth movement" Science Daily Oct. 20, 2017.

Totsugawa, et al. "Ultrasonic annular debridement in minimally invasive aortic valve replacement" Gen Thorac Cardiovasc Surg. Jan. 2020;68(1):81-83. doi: 10.1007/s11748-019-01158-8. Epub Jun. 15, 2019. (Abstract Only).

Ucirvine, "Electroacupuncture for Hypertension in Women: The Susan Samueli Center for Integrative Medicine at UC Irvine is Recruiting Patients for a Study", Principle Investigators: Dr. Stephanie Tjen-a-Looi and Dr. Shaista Malik, MOD# 20266, HS# 1999-2222, (2017), 1 page.

Valvublator Heart Valve Regeneration, accessed Apr. 24, 2020 https://valvublator.com (6 pages).

Van Dam et al. "RANK/RANKL signaling inhibition may improve the effectiveness of checkpoint blockade in cancer treatment" Critical Reviews in Oncology/Hematology vol. 133, Jan. 2019, pp. 85-91.

Verna et al. "The rate and the type of orthodontic tooth movement is influenced by bone turnover in a rat model" European Journal of Orthodontics 22 (2000) 343-352.

Vilela-Martin et al., "Effects of Transcutaneous Electrical Nerve Stimulation (TENS) on Arterial Stiffness and Blood Pressure in Resistant Hypertensive Individuals: Study Protocol for a Randomized Controlled Trial," Trials, vol. 17, (2016), pp. 1-13.

Wang et al. "Local and sustained miRNA delivery from an injectable hydrogel promotes cardiomyocyte proliferation and functional regeneration after ischemic injury", Nat Biomed Eng. 2017; 1: 983-992, doi: 10.1038/s41551-017-0157-y.

Abdel-Rehim "Change of serum klotho protein and its relationship with endothelial dysfunction, oxidative stress and arterial aging in essential hypertensive patients" J Kidney 2018, vol. 4 (Dec. 2018).

Ahrens et al. "Klotho expression is a prerequisite for proper muscle stem cell function and regeneration of skeletal muscle" Ahrens et al. Skeletal Muscle (Jul. 2018) 8:20 pp. 1-14.

Akbari ei al. "Association of Klotho gene polymorphism with hypertension and coronary artery disease in an Iranian population" BMC Cardiovascular Disorders (Dec. 2018) 18:237.

Carboni ei al. "An initial study on the effect of functional electrical stimulation in erectile dysfunction: a randomized controlled trial" IJIR: Your Sexual Medicine Journal (May 2018) 30:97-101.

Chaikin et al. "Microcurrent stimulation in the treatment of dry and wet macular degeneration" Clinical Ophthalmology 2015:9 2345-2353 (Dec. 2015).

Jamal et al. "Klotho, Hypertension and Arterial Stiffness: A Review" Austin J Nephrol Hypertens.(Jul. 2019) 6(2) 1082.

JCCR "Emerging roles of klotho in cardiovascular diseases%5D" Accessed Jun. 2, 2021 https://medcraveonline.com/JCCR/emerging-roles-of-klotho-in-cardiovascular-diseases.html%5D.

Kawagishi et al. S"onic hedgehog signaling regulates the mammalian cardiac regenerative response" Journal of Molecular and Cellular Cardiology; vol. 123, P180-184 (Oct. 2018).

Leonhardt "PressureStim Blood Pressure Control" accessed Jun. 2, 2021, https://pressurestim.com.

Leonhardt "PressureStim Receives IRB Approval to Launch Bioelectric Hypertension Treatment Clinical Study" Accessed Jun. 2, 2021, https://www.prdistribution.com/news/pressurestim-receives-irb-approval-to-launch-bioelectric-hypertension-treatment-clinical-study-2.html?fbclid=IWAR28Dh97RAKXXHrfgUONKW1pk-MWyeF_ibUlpQc_2XEN32C6sS%E2%80%A6.

Maltese et al. "The Putative Role of the Antiageing Protein Klotho in Cardiovascular and Renal Disease" Hindawi Publishing Corporation International Journal of Hypertension, (Sep. 2011) vol. 2012, Article ID 757469, 5 pages.

McMillan "Longevity Protein' Enables Muscle Regeneration In Old Mice" accesses Jun. 2, 2021 https://www.forbes.com/sites/fionamcmillan/2018/11/25/longevity-protein-enables-muscle-regeneration-in-old-mice/? sh=51709d57392a.

Ronchetti et al. "Dermal alterations in patients with Wilson's disease treated with D-penicillamine" J Submicrosc Cytol Pathol (Jan. 1989)21(1 ):131-9.

Santos et al. "Interferential electrical stimulation improves peripheral vasodilatation in healthy individuals" Braz J Phys Ther. May-Jun. 2013. 17(3):281-288.

Sartori et al. "Effects of Transcutaneous Electrical Nerve Stimulation in Autonomic Nervous System of Hypertensive Patients: A Randomized Controlled Trial" Current Hypertension Reviews, Apr. 2018, 14, 66-71.

Su et al. "Klotho protein lowered in elderly hypertension" Int J Clin Exp Med (Aug. 2014) 7(8):2347-2350.

Sun "Regulation of Blood Pressure by Klotho" University of Oklahoma Health Sciences Center, Oklahoma City, OK, United States; accessed Jun. 2, 2021; https://grantome.com/grant/NIH/R01-HL102074-01A1.

Takenaka et al. "Klotho Supplementation Attenuatesblood Pressure and Cyst Growth Inmouse Polycystic Kidney Disease" Journal of Hypertension: vol. 36—Issue—p. e76 (Jun. 2018).

(56) References Cited

OTHER PUBLICATIONS

Zhou et al. "Klotho Ameliorates Kidney Injury and Fibrosis and Normalizes Blood Pressure by Targeting the Renin-Angiotensin System" The American Journal of Pathology, vol. 185, No. 12, Dec. 2015.

Zhou et al. "Klotho Gene Deficiency Causes Salt-Sensitive Hypertension via Monocyte Chemotactic Protein-1/CC Chemokine Receptor 2-Mediated inflammation" J Am Soc Nephrol 26:121-132, 2015 (Accepted Apr. 2014).

Chen et al. "Beyond anti-VEGF: dual-targeting antiangiogenic and antiproliferative therapy" Am J Transl Res. 2013;5(4):393-403 Published May 24, 2013.

Chen et al. "Nanosecond Pulsed Electric Field (nsPEF) Ablation as an Alternative or Adjunct to Surgery for Treatment of Cancer" Chen et al., Surgery Curr Res 2013, S12 Doi: 10 4172/2161-1076.S12-005.

Costa et al. "Selecting patients for cytotoxic therapies in gastroenteropancreatic neuroendocrine tumours" Best Pract Res Clin Gastroenterol Dec. 2012;26(6):843-54. doi: 10.1016/j.bpg 2012 12.001 PMID: 23582923.

Costa et al. "Treatment of advanced hepatocellular carcinoma with very low levels of amplitude-modulated electromagnetic fields" Br J Cancer. Aug. 2, 20113;105(5):640-8. doi: 10.1038/bjc.2011.292. Epub Aug. 9, 2011. PMID 21829195; PMCID: PMC3188936.

Itatani et al. "Resistance to Anti-Angiogenic Therapy in Cancer-Alterations to Anti-VEGF Pathway" Int J Mol Sci. Apr. 18, 2018;19(4):1232. doi: 10.3390/ijms19041232. PMID: 29670046; PMCID: PMC5979390.

Ledzewicz et al. "Analysis of optimal controls for a mathematical model of tumor anti-angiogenesis" Optim. Control Appl. Meth. 2006; 00:1-16.

Loizzi et al. "Biological Pathways Involved in Tumor Angiogenesis and Bevacizumab Based Anti-Angiogenic Therapy with Special References to Ovarian Cancer" International Journal of Molecular Sciences. (Sep. 2017) 18(9): 1967. https://doi.org/10.3390/ijms18091967.

Lopes-Bastos et al. "Tumour-Endothelial Cell Communications: Important and Indispensable Mediators of Tumour Angiogenesis" Anticancer Research Mar. 2016, 36 (3) 1119-1126.

Muratori et al. "The cytotoxic synergy of nanosecond electric pulses and low temperature leads to apoptosis" Sci Rep 6, 36835 (2016). https://doi.org/10.1038/srep36835.

Odell et al. "Anti-inflammatory Effects of Electronic Signal Treatment" Pain physician. 11.891-907 (2008). 10 36076/ppj.2008/11/891.

Payne et al. "Bioelectric Control of Metastasis in Solid Tumors" BioelectricityVol. 1, No. 3, (Sep. 16, 2019) https://doi.org/10.1089/bioe.2019.0013.

Rocha et al. "Ultrasensitive System for Electrophysiology of Cancer Cell Populations: A Review" BioelectricityVol. 1, No. 3 (Published Online:Sep. 16, 2019) https://doi.org/10.1089/bioe.2019.0020.

Yuan et al. "Electrical stimulation enhances cell migration and integrative repair in the meniscus" Sci Rep 4, 3674 K2014). https://doi.0rg/10.1038/srep03674.

Zhong et al. "TKI-31 inhibits angiogenesis by combined suppression signaling pathway of VEGFR2 and PDGFRbeta" Cancer Biology & Therapy 5:3, 323-330, Mar. 2006.

Zimmerman et al. "Cancer cell proliferation is inhibited by specific modulation frequencies" Br J Cancer. Jan. 1, 20127;106(2):307-13. doi: 10.1038/bjc 2011.523. Epub 2011 Deci. PMID: 22134506; Pmcid: PMC3261663.

Zimmerman et al. "Targeted treatment of cancer with radiofrequency electromagnetic fields amplitude-modulated at tumor-specific frequencies" Chin J Cancer. Nov. 2013;32(11):573-81. doi: 10.5732/cjc.013.10177. PMID: 24206915 Pmcid: PMC3845545.

TUMOR THERAPY

CROSS-REFERENCE TO RELATED APPLICATIONS

This application is a continuation-in-part of U.S. patent application Ser. No. 15/460,129, filed on Mar. 15, 2017 (U.S. 2017/0266371A1, Sep. 21, 2017), now U.S. Pat. No. 10,646,644 B2 (May 12, 2020), which itself claims the benefit under 35 USC § 119 of:

U.S. Provisional Patent Application Ser. No. 62/308,702, filed Mar. 15, 2016;

U.S. Provisional Patent Application Ser. No. 62/363,012, filed Jul. 15, 2016;

U.S. Provisional Patent Application Ser. No. 62/364,472, filed Jul. 20, 2016;

U.S. Provisional Patent Application Ser. No. 62/375,271, filed Aug. 15, 2016;

U.S. Provisional Patent Application Ser. No. 62/385,124, filed Sep. 8, 2016;

U.S. Provisional Patent Application Ser. No. 62/454,521, filed Feb. 3, 2017; and U.S. Provisional Patent Application Ser. No. 62/352,930, filed Jun. 21, 2016, the disclosure of each of which is incorporated herein in its entirety by this reference.

TECHNICAL FIELD

The application relates generally to the field of medical devices and associated treatments, and to precise bioelectrical stimulation of a subject's tissue, potentially augmented with the administration of a composition comprising, among other things, stem cells and nutrients, useful to stimulate and treat the subject, the subject's tissue(s), the subject's organ(s), and/or the subject's cells. More specifically described is a personalized bioelectric cancer tumor eradication therapy. Also described is a multi-modality bioelectric therapy protocol for cancer tumor treatment.

BACKGROUND

With current cancer therapies, the number of cancer deaths are on pace to exceed 13 million people annually worldwide. The number of cancer sufferers overall is thus expected to exceed 22 million people by 2030.

Current therapies suffer from various drawbacks. For example, besides being relatively non-specific, chemotherapy can be toxic. Likewise for radiation therapy, which can be toxic and non-specific.

Bioelectric therapies are described in, e.g., U.S. Pat. No. 7,136,699 to Palti, the contents of which are incorporated herein by this reference, which describes an apparatus for selectively destroying dividing cells in living tissue formed of dividing cells and non-dividing cells. See also, U.S. Pat. No. 8,465,533 to Palti (Jun. 18, 2013), the contents of which are incorporated herein by this reference, which describes treating cancer using electromagnetic fields in combination with photodynamic therapy.

Existing bioelectric therapies (e.g., NovoCure™) tend to be non-specific and not customized.

BRIEF SUMMARY

Described are a system and method that "reads" cancer tumors real time and custom delivers individualized bioelectric therapy to the patient. For example, the system reads a cancer tumor, and based upon this read, delivers to the subject "a confounding signal" to jam communication within that tumor. A cancer tumor may change its communication patterns and the therapy is designed to change with these patterns, attempting to always jam the relevant communication signaling pathway. For example, if a cancer tumor is communicating on channel 3 Hz with 0.1 my and 0.1 micro amps, the system jams that channel with that signal. A cancer tumor may change its communication pathways once a day, which is one reason that it can be hard to stop.

The described system includes parameters not tied to communication jamming, which should also be customized to induce apoptosis to the cancer tumor. Such parameters include signals for starving a cancer tumor of blood supply (anti-VEGF) and signals for changing the cancer tumor's surface proteins and/or charge so that the immune system attacks the cancer tumor ("immunotherapy").

Changing the cancer tumor's surface proteins and/or charge is also preferably customized since each tumor will have different surface protein signature(s) that need to be modified. A cancer tumor may "cloak" itself much the same way a fetus has protein cloaks so that the mother's immune system does not attack the fetus in utero. When the system and methods modify a cancer tumor to start an immunotherapy response, the cancer tumor may quickly modify it further to establish a new cloak to avoid attack and for survival. The only effective treatment is one that modifies constantly as the cancer tumor modifies itself trying to survive.

The described system(s) and method(s) utilize bioelectric signals to stop tumor growth by, e.g., halting cell division and starving blood supply to the cancer tumor. The system and method utilize a computer data base that knows the bioelectric signal read profile of healthy organs and distinguishes when an organ is affected by cancer as being different than healthy normal.

In certain embodiments, a relatively non-toxic treatment method as described herein includes first "reading" (or "neural code reading") of a particular cancer tumor and otherwise analyzing the cancer tumor (or "neural code analyzing"), and preparing and delivering a personalized bioelectric reprogramming of the cancer tumor (or "neural code delivery"). As used herein, the "reading" of the cancer tumor involves determining how the cancer tumor communicates with itself and jamming the determined signals. Preferably as many signals as possible from the cancer tumor are read and analyzed. Customized bioelectric signaling is then designed to "jam" the ability of the cancer tumor to communicate.

In order to "read" the cancer tumor and organ, the system preferably utilizes an implantable and/or wireless external, chronic, closed-loop neuromodulation device with concurrent sensing and stimulation.

In certain embodiments, described is a bioelectric therapy protocol comprising: reading a cancer tumor with real time bioelectric and surface protein sensing. Based upon this real time read, customized personalized bioelectric signals are delivered to the cancer tumor to do the following: (a) interfere with the cancer tumor's ability to communicate internally, (b) alter the cancer tumor's surface proteins so that the person's own immune system attacks the cancer tumor ("immunotherapy"), (c) alter the surface electrical charge of the cancer tumor, again so that the person's own immune system attacks it—immunotherapy, (d) deliver anti-angiogenic proteins to starve the cancer tumor of blood supply, (e) stop cell division in the cancer tumor, and/or manage and modulate inflammation about the cancer tumor.

After the cancer tumor has been eradicated (or tumor growth has subsided) the bioelectric stimulator then can deliver bioelectric signals to: (a) recruit regenerative stem cells to the damaged organ with a homing signal, (b) proliferate recruited stem cells to a greater quantity, (c) direct differentiation of such stem cells to useful tissue, (d) express and/or release proteins to stimulate healthy new blood vessel growth, (e) deliver 15+ regeneration promoting proteins including IGF1, and (f) express and/or release proteins to manage and modulate inflammation.

In certain embodiments, the described multi-stage bioelectric therapy comprises: custom reading of the cancer tumor(s), applying customized communication jamming signals to the cancer tumor, applying bioelectric signals to reduce blood supply to the cancer tumor to starve the cancer tumor, applying bioelectric signals to change surface proteins and/or surface electrical charge of a cancer tumor to help the immune system attack it, applying bioelectric signals to the cancer tumor to decrease cell division, applying bioelectric signals to manage inflammation, applying bioelectric signals to re-program cells of the cancer tumor to be non-cancerous, and applying bioelectric regeneration promoting signals to the affected tissue.

In certain embodiments, the described cancer treatment includes: scanning a subject's immune system with bioelectric scanning to identify and detect a cancer tumor or tumors; reading and analyzing electrical communication within a cancer tumor, delivering precise communication jamming signals to stop the cancer tumor from communicating; applying bioelectric signal(s) to reduce or stop cell division in the cancer tumor, applying bioelectric signal to the cancer tumor to reduce blood supply to the cancer tumor; reading and analyzing surface protein expressions of the cancer tumor; custom delivery of precise protein expression signals to change surface protein expression of the cancer tumor so that the immune system can detect and attack the cancer tumor as "enemy" via the subject's immune system; and applying a bioelectric signal to encourage organ regeneration (preferably to recover the organ back to full health).

In certain embodiments, a method for treatment as described herein includes: reading the cancer tumor with bioelectric means; applying customized bioelectric signals to jam tumor communication(s); applying customized bioelectric signals to starve the cancer tumor of blood supply (anti-VEGF); applying customized bioelectric signals to change surface proteins or surface charge of the cancer tumor so that the patient's immune system attacks the cancer tumor (immunotherapy); applying customized bioelectric signals to the cancer tumor to stop cell division; applying customized bioelectric signals to ZAP the cancer tumor (ablation); applying signals to resonate cancer tumor cells to point of burst; applying customized bioelectric signals to reprogram cancer cells including bioelectric gene editing; applying customized bioelectric signals to regenerate healthy tissue, and applying customized bioelectric signals to manage inflammation.

In certain embodiments, a method for treatment includes: scanning the subject's body for cancer with bioelectric scanning, reading and analyzing electrical communication within a cancer tumor, based upon the reading and analysis, custom delivering precise communication jamming signals to stop the cancer tumor from communicating, applying to the cancerous area a bioelectric signal that hinders cell division, applying to the cancerous area a bioelectric signal sequence for starving cancer tumor of blood supply, reading and analyzing surface protein expression of the cancer tumor, based upon the reading and analysis, custom delivery of precise protein expression signals to change surface protein expression of the cancer tumor so immune system attacks it as enemy. Such a method can further include immuno-response therapy, and applying to the cancer tumor area a bioelectric signal sequence for organ regeneration. A computer data base may be utilized that knows the bioelectric signal read profile of healthy organs and distinguishes when an organ is afflicted with cancer as being different than healthy normal.

In certain embodiments, a method for treatment includes: a custom read of the cancer tumor, application of customized communication jamming signals, applying bioelectric signals to starve the cancer tumor of blood supply, applying bioelectric signals to change the surface proteins and surface electrical charge of the cancer tumor to induce the immune system to attack the cancer tumor, applying bioelectric signals to stop cell division in and about the cancer tumor, applying bioelectric signals to manage inflammation in the subject, bioelectric re-programming of the cancer tumor cells to be non-cancerous, and applying bioelectric regeneration promoting signals.

In certain embodiments, a method for treatment includes: the bioelectric reading of the cancer tumor, the custom jamming of communication of the cancer tumor adjusted real time, changing surface proteins to encourage the patient's immune system to attack the cancer tumor via the immune system, changing the surface electrical charge of the cancer tumor to get the immune system to attack the cancer tumor via the immune system, applying bioelectric signals to stop cell division signals in and around the cancer tumor, reducing blood supply to the cancer tumor, modulating inflammation signals sequence and adjust real time based upon real time reads, applying organ regeneration signals sequence, and reaching resonant frequencies of cancer cells to get them to burst.

In certain embodiments, a method for treatment includes: reading the cancer tumor; custom delivering bioelectric signals to jam communication of the cancer tumor based on the read; delivering bioelectric signals to change the surface protein make up and electrical charge of the afflicted cells so that the body's immune system attacks the cancer tumor ("immunotherapy"); applying bioelectric signals to starve the cancer tumor of blood supply; applying bioelectric signals to stop cell division in and about the cancer tumor; applying bioelectric/sound resonance signals to rupture cancer cells; applying bioelectric signals to manage inflammation (a cancer trigger); applying bioelectric signals to reprogram the cancer tumor cells; and applying high energy electrical bursts to ablate the cancer tumor.

In certain embodiments, a described cancer tumor treatment includes: reading the bioelectric communication signals within the cancer tumor and delivering a customized jamming signal to stop tumor growth; a specific bioelectric signal for stopping cell division; a specific set of bioelectric signals for starving a cancer tumor of blood supply; a set of bioelectric signals to change the surface protein expression of a cancer tumor so that the immune system attacks it; and when needed a micro infusion pump and mixed cell based composition, to regenerate an organ damaged by cancer back to full function and health; bioelectric scanning for early detection of cancers followed by bioelectric treatment followed by organ regeneration; application of vibrational energy (e.g., resonance) for various treatments; and light and bioelectric energy combined for various treatments.

In certain embodiments, a described cancer tumor treatment includes: bioelectric detection of a cancer tumor, bioelectric reading of communication signals within a cancer tumor; bioelectric signals to jam communication ability of the cancer tumor; bioelectric signals to starve the tumor of blood supply; bioelectric signals to stop cell division; bioelectric signal to change surface protein expression of the cancer tumor so that the immune system attacks it—("immunotherapy"); combination bioelectric and light therapy for cancer tumor destruction; and, if appropriate, bioelectric signals to regenerate tissues damaged from the cancer tumor for recovery.

In certain embodiments, the described system and method include: bioelectric scanning to detect cancer; bioelectric reading to determine properties of cancer tumor; customized signals based on read to jam ability of cancer tumor to communicate; customized signals based on read to change surface protein expression on the tumor to trigger immune response (so immune system attacks it); bioelectric signals for stopping cell division; bioelectric signals sequence for starving the tumor of blood supply (anti-VEGF and others); and bioelectric signal sequence to regenerate the organ after the cancer tumor has been destroyed, this may be combined with micro infusion pump and repeat delivery of stem cell plus growth factors mixed composition.

In certain embodiments, the system and method include measuring bioelectrical electrical activity of an organ (or organs), which can occur by placing a bion coil reader and transmitter in contact with the organ(s), and then analyzing information with an associated computer. The computer has stored the bioelectrical read measurements of diseased organs and healthy organs, and conducts a comparative examination, classifying the organ into one category or another.

A whole body and/or individual organ scanning can utilize a combination of a 3D body scanning, quantum magnetic resonance scanning, biofeedback scanning, bioelectric scanning, Bion implant scanning, nervous system scanning, and/or light activated cell reaction reading. 3D body scanning can be accomplished with, e.g., an Ina'Chi scanner or a 3D Quantum Health Analyzer. Quantum magnetic resonance scanning can be done with a QMRA Whole Body Health Scanner (Essentials Health, Somersworth, N.H., US).

Also described is an organ regeneration stimulator pump and composition system.

Described is a bioelectric stimulator (e.g., FIG. 1) including: a power source (e.g., battery, capacitor, or other suitable source of electricity), and means for delivering an electrical signal to a subject's tissue (e.g., via electrode(s) or wirelessly). The bioelectric stimulator utilizes the electrical signal to precisely control protein expression in the tissue on demand.

Also described is a method of using the bioelectric stimulator to regenerate and/or recover an organ in a subject (e.g., FIG. 2), the method including: delivering selected electrical signals to the organ so as to precisely control protein expressions in the right sequence and volume for total or near total organ regeneration and recovery. Such a method can further include separately delivering to the subject a cocktail of regenerative agents including any combination of the following: stem cells, endothelial progenitor cells, selected exosomes, selected alkaloids, selected anti-inflammatory agents, nutrient hydrogel, organ specific matrix, selected growth factors, amniotic fluid, placenta fluid, cord blood, and embryonic sourced growth factors and cells.

Also described is a method of using the bioelectric stimulator in a subject to regenerate brain cells (e.g., FIG. 5), the method including: generating electrical signals from the bioelectric stimulator to control the release of a protein, wherein the protein is selected from the group consisting of SDF-1, IGF-1, HGF, GDF-10, GDF-11, activin A, activin B, eNOS, HIF 1 alpha, neurogenin 3, PDGF, tropoelastin, and any combination thereof. Such a method can further include: separately delivering to the subject stem cells and/or growth factors including any combination of GDF-10, GDF-11, SDF-1, IGF-1, HGH, activin A, activin B, eNOS, HIF 1 alpha, IL-6, PDGF, HGF, and tropoelastin.

Also described is a method of using the bioelectric stimulator in a subject to repair and grow muscle, the method including: generating electrical signals from the bioelectric stimulator to control the release of a protein, wherein the protein is selected from the group consisting of SDF-1, IGF-1, HGF, EGF, myoblast injections, cardiac muscle stem cell injections, immature myoblasts, PDGF, HGF, follistatin, tropoelastin, HGF, Human Growth Hormone (HGH), pyruvate, HIF 1 alpha, and any combination thereof.

Also described is a method of using the bioelectric stimulator in a subject to repair DNA, the method including: generating electrical signals from the bioelectric stimulator to control the release of IGF-1.

Also described is a method of using the bioelectric stimulator to achieve a desired result in a subject, wherein the desired result is selected from the group consisting of brain regeneration, hair regeneration, eye regeneration, ear hearing regeneration, skin regeneration, tooth regeneration, dental gum regeneration, tooth root canal regeneration, sub-mucosa regeneration, breast tissue generation, aorta regeneration, limb regeneration, artery regeneration, heart regeneration, heart valve regeneration, kidney regeneration, pancreas regeneration, bladder regeneration, liver regeneration, joint regeneration, bone regeneration, and any combination thereof.

Also described is a bioelectric stimulator including: a power source (e.g., battery, capacitor, or other suitable source of electricity), and means for delivering an electrical signal to a subject's tissue (e.g., via electrode(s) or wirelessly), wherein the bioelectric stimulator utilizes the electrical signal to precisely control stem cell homing, proliferation and differentiation in the tissue on demand. Such a bioelectric stimulator preferably utilizes the electrical signal to precisely control protein expression. Also described is a method of using such a bioelectric stimulator to regenerate and/or recover an organ in a subject, the method including delivering an electrical signal to the organ with the bioelectric stimulator.

A preferred system includes:

1. A bioelectric stimulator that controls/stimulates the release/production of, for example, SDF1, IGF1, EGF, HGF, PDGF, eNOS, VEGF, Activin A and B, RANKL/OPG/TNF A, Follistatin, IL-6, HIF-1 Alpha, and tropoelastin. In certain embodiments, it also releases/stimulates GDF-10, GDF-11, Relaxin, FGF, TGF, and/or neurogenin-3.

2. A micro infusion pump (e.g., a FluidSync™ micropump available from Fluidsynchrony of Pasadena, Calif., US), which is programmable and re-fillable and preferably has a low cell damage design. Such a pump preferably includes a refilling silicon septum port or ports and reservoir chambers.

3. A multi-component organ regeneration composition that includes (depending on the application) adipose-derived stem cells, muscle-derived stem cells (when needed for muscle), exosomes, Micro RNAs, nutrient hydrogel, growth factor cocktail, organ specific matrix, selected alkaloids, and/or selected anti-inflammatory agents.

The pump and stimulator may be associated with (e.g., connected to) the organ to be treated/regenerated with a pacing infusion lead (available from Nanoscribe of Eggenstein-Leopoldshafen, Germany). The interface with the organ varies by organ, e.g., a conductive soft wrap can be used for certain applications.

The stimulator can be designed to externally deliver all regeneration promoting signals wirelessly to the subject's organ(s), tissue(s), and/or cells.

In certain embodiments, described is a preferred device for regenerating organs by controlled release of organ regenerating promoting proteins by a bioelectric stimulator. Such a device may utilize bioelectric signals delivered wirelessly to the organ(s), tissue(s), and/or cell(s) being treated. Such a device may utilize bioelectric organ regeneration signals delivered via the nervous system of the subject being treated.

In certain embodiments, described is a device for regenerating organs by controlled release of stem cell homing signals (SDF-1 and PDGF), stem cell differentiation signals, blood vessel growth signals, and organ specific tissue building signals.

In certain embodiments, described is a system for regenerating organs, the system comprising: an optional bioelectric stimulator that controls release of organ regeneration promoting proteins; a re-fillable micro infusion pump; a mixed organ regeneration composition of stem cells and growth factors; and electrical pacing and infusion lead(s) directed to with tip inserted into the organ(s) to be treated. Such a device may include a mixed composition including any or all of the following components: SDF-1, IGF-1, PDGF, IL-6, HIF-1 Alpha, follistatin, tropoelastin, relaxin, GDF-10, GDG-11, HGF, EGF, eNOS, VEGF, adipose derived stem cells, iPS cells, cardiac derived stem cells, skeletal muscle derived muscle progenitor cells, endothelial cells, stromal fraction, selected exosomes, selected Micro RNAs, selected alkaloids, selected anti-inflammatory agents, organ specific matrix, and/or nutrient hydrogel.

The described systems and methods also have utility for treating (e.g., shrinking or eliminating) polyps, fibroids, and/or cysts in the colon, rectum, throat, eye, uterus, ear canal, or submucosa, which can advance to cancer (about 7%). The bioelectric stimulation and scanning lead are directed to the location of the growth to be treated via standard endoscopes normally use for biopsies or minimally invasive surgical removal. The system and/or method scans, reads and analyzes polyps, cysts and fibroids to determine if cancerous or not without a biopsy and to determine communication method signals. It then customizes a bioelectric treatment sequence designed to (1) jam communication, (2) stop cell division, (3) shrink and/or eliminate growth, (4) change surface proteins so the person's body attacks growth—immunotherapy, (4) change surface electrical charge, (5) starves growth of blood supply—anti-angiogenic proteins, (6) heal and regenerates tissues post growth shrinkage or eradication, and (7) manage and modulate inflammation. If polyp, cyst or fibroids are removed with standard minimally invasive surgery methods, the bioelectric stimulation sequences are designed to accelerate healing, reduce bleeding and provide pain relief. Bioelectric stimulation lead may also deliver harmonic resonant vibration signals designed to burst growth cells like an opera singer shatters a wine glass, if desired. The pacing infusion lead may also be used to deliver a proprietary PS-15 cocktail comprised of stem cells, growth factors, amniotic fluid, PRF, selected exosomes, selected alkaloids, selected Micro RNAs, engineered hydrogel, mucosa matrix and oxygenated nano particles as a secondary treatment methodology in difficult cases.

DETAILED DESCRIPTION

Figure 1:
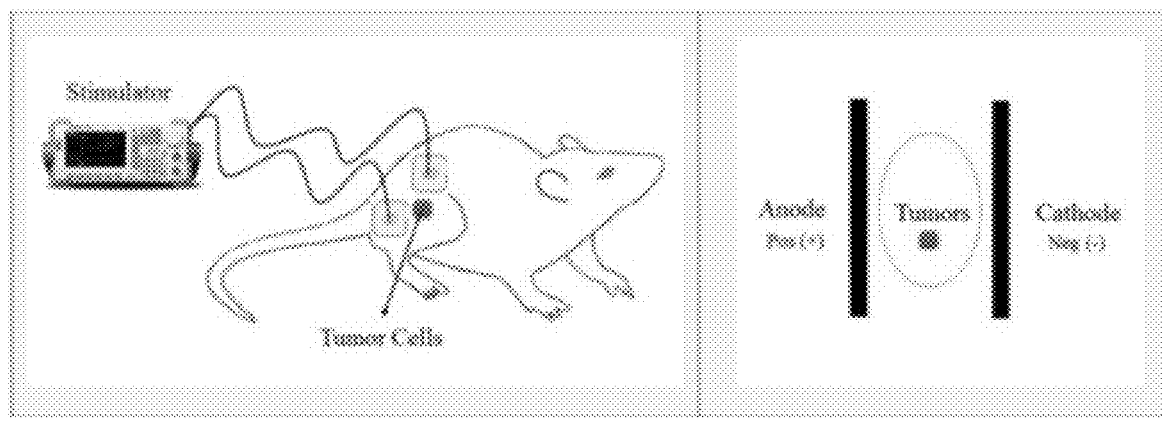
FIG. 1 depicts a programmed bioelectric stimulator for delivery to tumor cells of a subject via two electrodes. The anode wire/electrode may be placed directly into the tumor or adjacent to the tumor.

In certain embodiments, the system includes reading the communications within the cancer tumor, and based upon this reading, custom delivering bioelectric signals to the cancer tumor, especially signals that jam or interfere with communication signals within the cancer tumor. Preferably, besides jamming communications, included in the treatment are electrically zapping the cancer tumor ("ZAP Ablation"), changing surface-immunotherapy, starving blood supply, resonant rupturing, and cancer reprogramming, followed by applying healthy signals for regeneration of health including inflammation management. All components of treatment work together in balance.

In certain embodiments, the sequence to confound electrical signaling is applied with a voltage of greater than 0.1 volts, but less than about 2 volts.

In certain embodiments, the sequence to confound electrical signaling is applied with a current greater than 2 micro amps, but less than about 70 micro amps.

In certain embodiments, the application of treatment signals for confounding tumor communication is applied for a duration of about 4 minutes.

In certain embodiments, the sequence to jam tumor communications are two frequencies in succession. The first frequency is 200 kHz±10% and the second frequency is 300 kHz±10% alternating in bursts back and forth. The amplitude is at least 0.6 V/cm RMS for 4 minutes.

These bioelectric signals may be combined with protein expression and/or release signals, which can be used to, e.g., cut off the blood supply to the cancer tumor. For example, bioelectric signaling can lead to preferably the enhanced expression and/or release of thirteen or more selected proteins (e.g., ones useful for organ regeneration, stopping cell division, enhancing the patient's immunological response, and inhibiting blood supply to the cancer tumor and surrounding tissues).

In ZAP ablation, a needle has an electrically insulated shaft, a length of 50 mm or 80 mm and an outer diameter of 0.7 mm. The bare tip, including the bevel section has a length of approximately 6 mm. Energy is delivered via a computer-controlled regime (voltage/current controlled) and triggered by the operator's needle movements by means of a miniaturized accelerometer. The applied symmetrical burst pulses have a 55 ms linear ramp, a duration of 200 ms and a radiofrequency (RF) period of 3.3 µs. Every burst pulse incorporates around 60,000 periods and delivers an energy of approximately 6 J. Consecutive burst pulses are separated by a minimum time interval. Additionally, pulses are blocked if the velocity of the needle is too low in order to ensure sufficient heat conduction. The system preferably conforms to the international safety norm EN 60601-1, and meets the insulation demands of cardiac floating regarding patient applied parts, that is, a frequency weighted patient leakage current of less or equal to 10 µA, which is lower than that required to disturb the cardiac activity even in direct contact.

If communication jamming alone is used in the therapy, results will typically be less than desired (e.g., only about 30% of patients having good results). If "blood starving" alone is used, you also get less than desired results. With immunotherapy alone, you also get less than desired results. Only in combination can one improve upon these mediocre results to achieve results of >70% efficacy. Preferably, the system delivers healthy inflammation management and healthy regeneration proteins for the organ after all the harsh signals designed to eradicate the cancer tumor.

One Inflammation Management Signals Sequence is application of a direct microcurrent of 0.35 µA for 8.5 hours daily during the inflammation management phase of the therapy in an anti-inflammatory frequency range of 139-147 Hz+3 V/cm, 10 Hz, 0.2 ms pulse duration for 4 hours.

In one embodiment, instead of reading the cancer tumor and custom jamming its communication signals, communication jamming signals that are likely to interfere with the cancer tumor's communications are sent. Such signals are typically combined with signals that change surface proteins on the cancer tumor and apply a charge to the cancer tumor to elicit an immune response against the cancer tumor. Further signals are applied that starve the cancer tumor of blood supply via the expression of anti-angiogenesis proteins.

In certain embodiments, the bioelectric therapy signal applied to the cancer tumor to change surface protein(s) and the surface charge so as to stimulate the immunotherapy response (e.g., so that the patient's own immune system attacks the cancer tumor) is, first, 300 ns, 1.8-7 kV/cm, 50-700 pulses and, second, 300 ns pulses with a threshold of greater than 20 kV/cm and an effective electric field of 40 kV/cm.

For starving the cancer tumor's blood supply, anti-VEGF (vascular endothelial cell growth factor) antibodies are injected and an anti-TGF beta signal sent (e.g., a signal of 10 V, 5 ms, 1 Hz 24 hours, and 9.1 times with 20 V, 5 ms, 1 Hz, 24 hours) together with the following signal: pulse duration fixed at 100 ns, and the intensity of electric fields varied from 5 to 40 kV/cm; 25 pulses at electric fields between 10 kV/cm to 30 kV/cm. The inhibition of TGF beta 1 receptor was three times in rhabdomyosarcoma when applied 10 V, 5 ms, 1 Hz 24 hours, and 9.1 times with 20 V, 5 ms, 1 Hz, 24 hours. A longer or more intense signal reduced the effect. In human colon carcinoma cells, the reduction doubled (significant result).

U.S. Pat. No. 4,622,952 to Gordon (Nov. 18, 1986), the contents of which are incorporated herein by the reference, describes a process for treating cancer by applying external electromagnetic energy able to achieve biophysical alterations in the intracellular structure of cancer cells in living tissue, including stimulation of intracellular production of interferon. The process tunes an external electromagnetic energy to the resonant energy absorption frequencies of the intracellular structure of the selected cells and then exposing the subject to this tuned electromagnetic energy field. Alternatively, the field can be tuned to the frequency that has been calculated to be closest to the resonant frequency of the cancer cells and furthest from the resonant frequency of the normal cells. The process may be further enhanced by the intracellular absorption of selected materials designed to alter the magnetic susceptibility and therefore the resonant energy absorption frequency of the intracellular structure. See, also, U.S. Pat. No. 5,211,622 to Liboff et al. (May 18, 1993), the contents of which are incorporated herein by the reference.

In certain embodiments, a signal generator coupled with a voltage amplifier is set to apply electrical stimulation as described herein via needle electrode pair to tumors.

In certain embodiments, a system for use herein comprises: a probe for determining a resident electrical signal found in a species of cancer, a computer system comprising a processor for modifying each resident electrical signal to form at least one confounding electrical signal unique to each resident electrical signal, and a data storage for all confounding electrical signals, and a probe for applying a selected one of the confounding electrical signals to the cancer Confounding electrical signals may be applied with a voltage greater than 0.1 volts, but less than 2 volts. Further confounding electrical signal may be applied with a current greater than 2 micro amps but less than 70 micro amps. Application of treatment signals for confounding tumor communication may be applied for a duration of, for example, 4 minutes.

In one embodiment, one high frequency and one low frequency are utilized. The high frequency had to be exactly eleven times higher than the low, which in music is known as the 11th harmonic. At this 11th harmonic, microorganisms begin to shatter like crystal glass.

Pancreatic cancer cells are specifically vulnerable between 100,000-300,000 Hz. See, e.g., "Could Resonant Frequency Lead to a Less Intrusive Cancer Treatment?" futurism.com Jan. 27, 2016, "Shattering Cancer With Resonant Frequencies" (Oct. 21, 2015) (the frequencies, known as oscillating pulsed electric field (OPEF) technology, destroyed an average of 25 percent to 42 percent of leukemia cells (up to 60 percent), and slowed the growth of cancer cells by up to 60 percent. Ovarian cancer cells also succumbed to OPEF, as did antibiotic-resistant bacteria (including methicillin-resistant *Staphylococcus aureus* (MRSA)). The electronic signals not only rendered MRSA vulnerable to antibiotics, but also slowed growth.), and C. Sarich "The Science of Curing Cancer and Other Diseases with Sound and Resonant Frequencies" *Waking Times*, Jul. 8, 2017.

For example, the use of high intensity focused ultrasound (HIFU) to rapidly heat and kill tumors of the liver or kidney. In certain embodiments, an ultrasound hyperthermia system is utilized to heat tissue. With this form of cancer therapy, the dose of X-rays or drugs can be reduced when tissue is heated by 6-10° C., and still achieve the required therapeutic effect.

In High Intensity Focused Ultrasound (HIFU), cells in a selected target volume are rapidly heated to a temperature at which they are killed instantly. This has the potential to treat tumors of, e.g., the liver or kidney non-invasively, without the need for conventional surgery.

The most effective signal for stopping cell division is 10 to 20 V, 5 ms, 1 Hz for 3 to 24 hours. This effect showed to be dose-dependent and increases three days post treatment. These signals modulate genes encoding proteins that act in different processes than cell division to granule-induced cell death by cytotoxic lymphocytes. In the opposite, the halt blood signals are lower voltage signals: 2 to 5 V. The lower voltage signals affect the expression of a variety of genes, which clue for angiogenesis in tumor and stem cells. An alternate application of using both signals, starting with the high voltage, appears as an interesting strategy. Intermittent use of the signal, especially in solid tumors is also reasonable.

The use of anti-VEGF antibodies for the treatment of cancer is described in EP 0666868 B1, the contents of which are incorporated herein by this reference.

In a preferred embodiment, the organ regeneration composition hereof comprises adipose-derived stem cells, bone marrow-derived stem cells, muscle-derived stem cells (e.g., when needed for muscle), exosomes, MicroRNAs, nutrient hydrogel, growth factor cocktail, organ specific matrix, selected alkaloids, and/or selected anti-inflammatory agents.

Figure 2:
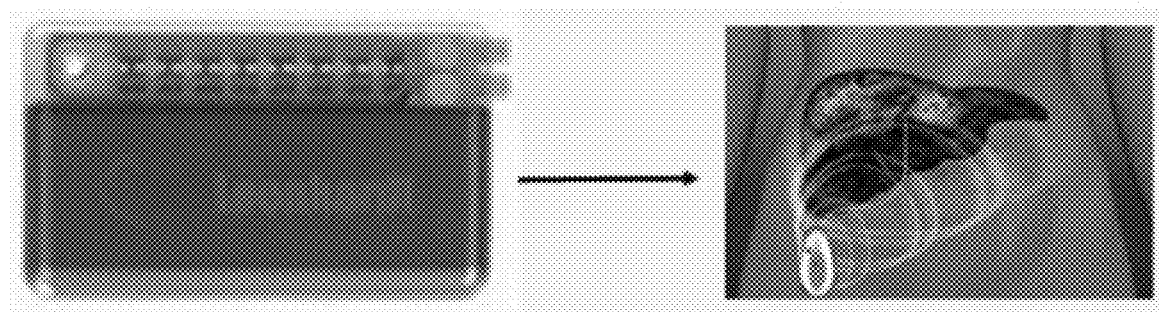
FIG. 2 depicts an implantable lead with simulated therapy for liver cancer.

Referring now to FIG. 1, depicted is a stimulator for use with treatment of, e.g., a cancer tumor. Preferably, such a device is about the size of two quarters (available from QIG Greatbatch/Greatbatch, Inc. of Frisco, Tex., US) (FIG. 2).

The microinfusion pump for continuous or repeat delivery of a liquid composition, which microinfusion pump includes silicon septum ports and associated reservoir chambers connected to the bioelectric stimulator microinfusion pump to the tissue with a pacing infusion lead. The pump is preferably programmable and re-fillable with low cell damage design. Refilling may be by silicon septum ports and reservoir chambers The organ specific matrix is a composition comprising cells of an organ which is to be treated. The organ specific matrix is believed to aid in stem cell differentiation, but in any event is found to be useful in the composition. It has been found that for the multicomponent composition, cells plus selected growth factors are better than just cells alone. See, e.g., Prochazka et al. "Therapeutic Potential of Adipose-Derived Therapeutic Factor Concentrate for Treating Critical Limb Ischemia," *Cell Transplantation*, 25(9), pp. 1623-1633(11) (2016) and "Cocktail of Factors from Fat-derived Stem Cells Shows Promise for Critical Limb Ischemia," world wide web at sciencenewsline.com/news/2016012204520017.html (Jan. 22, 2016), the contents of each of which are incorporated herein by this reference.

Figure 3:
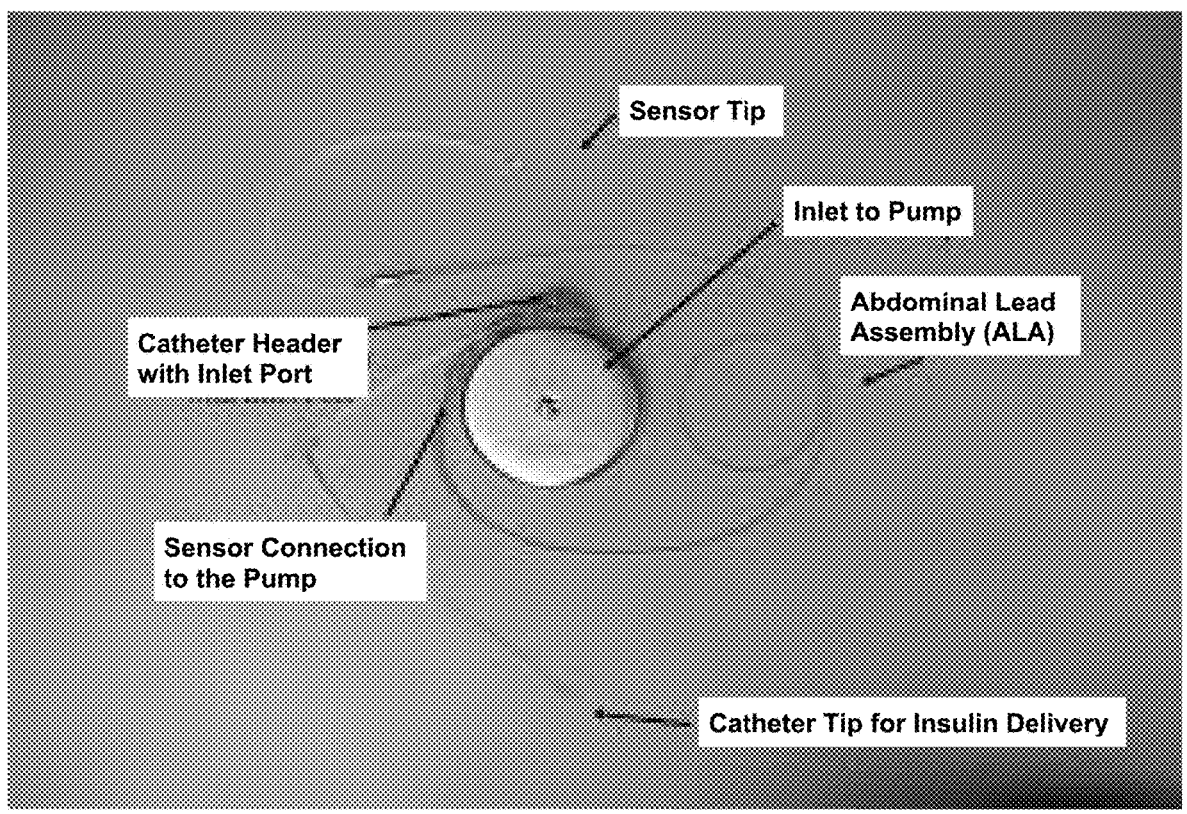
FIG. 3 depicts an interface for use with the system.
Figure 4:
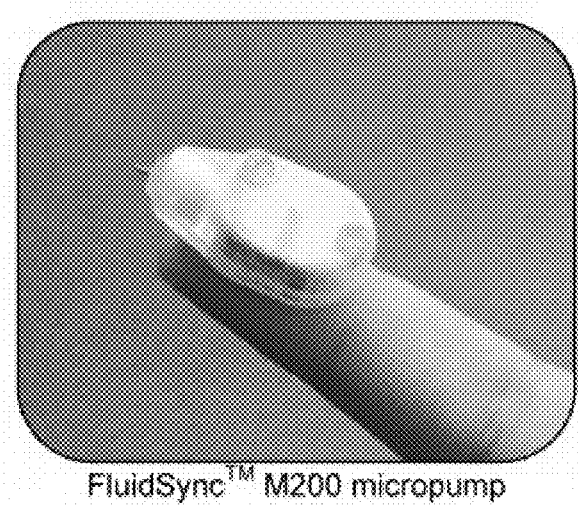
FIG. 4 depicts a micropump for use with the system.
Figure 5:
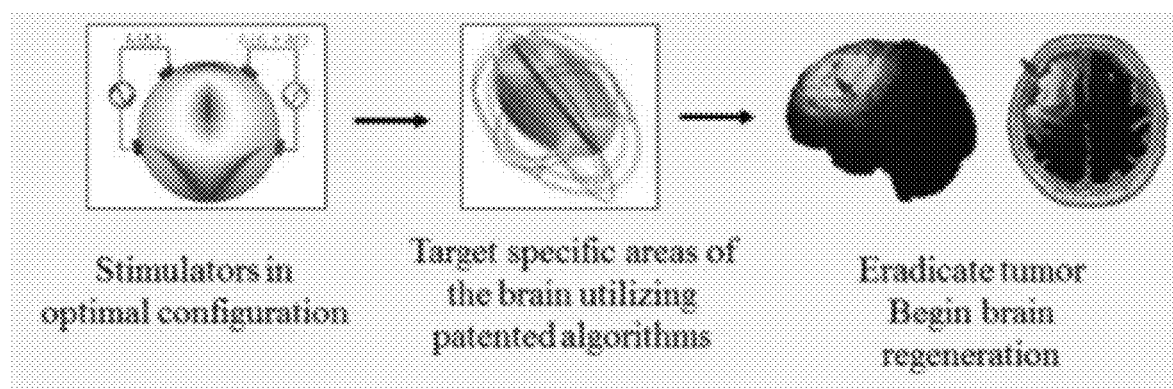
FIG. 5 depicts a system for targeting glioblastoma using algorithms.

In case of an advanced disease state, a micro infusion pump (e.g., FIGS. 3 and 4) is used for daily delivery of, e.g., 2 ml of organ regeneration composition (comprised of adipose-derived cells or bone marrow-derived mesenchymal stem cells plus cocktail of growth factors (usually derived from amniotic fluid or placenta), selected Micro RNAs, selected alkaloids, selected anti-inflammatory agents, nutrient hydrogel, organ specific matrix, selected exosomes). For muscle regeneration, immature myoblasts are included in the composition.

Exosomes represent a specific subset of secreted membrane vesicles, which are relatively homogeneous in size (30-100 nm). Exosomes have been proposed to differ from other membrane vesicles by its size, density, and specific composition of lipids, proteins, and nucleic acids, which reflect its endocytic origin. See Campbell et al. "Electrical stimulation to optimize cardioprotective exosomes from cardiac stem cells" *Med Hypotheses*. 2016 March; 88:6-9. doi: 10.1016/j.mehy.2015.12.022. Epub 2016 Jan. 11.

Exosomes are formed in endosomal vesicles called multivesicular endosomes (MVEs) or multivesicular bodies, which originate by direct budding of the plasma membrane into early endosomes. The generation of exosomes to form MVEs involves the lateral segregation of cargo at the delimiting membrane of an endosome and inward budding and pinching of vesicles into the endosomal lumen. Because exosomes originate by two successive invaginations from the plasma membrane, its membrane orientation is similar to the plasma membrane. Exosomes from many cell types may contain similar surface proteins as the cell from which it is derived. Membrane proteins that are known to cluster into microdomains at the plasma membrane or at endosomes, such as tetraspanins (CD63, CD81, CD82), often are also enriched in EVs. It is also thought that endosomal sorting complex responsible for transport system and tetraspanins, which are highly enriched in MVEs, play a role in exosome production. How cytosolic constituents are recruited into exosomes is unclear but may involve the association of exosomal membrane proteins with chaperones, such as HSC70, that are found in exosomes from most cell types. MVEs are also sites of miRNA-loaded RNA-induced silencing complex accumulation, and the fact that exosome-like vesicles are considerably enriched in GW182 and AGO2 implicates the functional roles of these proteins in RNA sorting to exosomes. Exosomes are released to the extracellular fluid by fusion of MVE to the plasma membrane of a cell, resulting in bursts of exosome secretion. Several Rab GTPases such as Rab 27a and Rab27b, Rab11 and Rab35, all seem to be involved in exosomes release.

Repeat doses of the composition are also preferred. See, e.g., Gavira et al. "Repeated implantation of skeletal myoblast in a swine model of chronic myocardial infarction," *Eur. Heart J.* 31(8): 1013-1021. doi: 10.1093/eurheartj/ehp342 (2010), the contents of which are incorporated herein by this reference.

SDF-1 is generally for recruiting stem cells and maturing blood vessels. IGF-1 is for DNA repair. HGF is for tissue regeneration and reduces arrhythmias in the case of heart. EGF grows tissue. VEGF grows blood vessels. PDGF is a second stem cell homing factor and helps tissue regeneration especially heart. eNOS dilates blood vessels. Follistatin promotes muscle growth. Activin A and B regenerates nerve cells and neurons. Tropoelastin increases elasticity of all tissues especially arteries, skin, heart, aorta. GDF-10 and GDF-11 promote regeneration especially of nerve cells and neurons. Neurogenin-3 is especially helpful in brain and pancreas regeneration. Relaxin helps heart regeneration.

The micro voltage signal generator may be produced utilizing the same techniques to produce a standard heart pacemaker well known to a person of ordinary skill in the art. An exemplary microvoltage generator is available (for experimental purposes from Cal-X Stars Business Accelerator, Inc. DBA Leonhardt's Launchpads or Leonhardt Vineyards LLC DBA Leonhardt Ventures of Salt Lake City, Utah, US). The primary difference is the special electrical stimulation signals needed to control, e.g., precise follistatin release on demand (which signals are described later herein). The leading pacemaker manufacturers are Medtronic, Boston Scientific Guidant, Abbott St. Jude, BioTronik and Sorin Biomedica.

Construction of the electric signal generators and pacemakers, are known in the art and can be obtained from OEM suppliers as well as their accompanying chargers and programmers. The electric signal generators are programmed to produce specific signals to lead to specific protein expressions at precisely the right time for, e.g., optimal organ treatment or regeneration.

The pacing infusion lead may be constructed or purchased from the same suppliers that build standard heart pacemaker leads. Pacing infusion leads may be purchased from a variety of OEM vendors. The pacing infusion lead may, for example, be a standard one currently used in heart failure pacing studies in combination with drug delivery.

An infusion and electrode wide area pitch may be constructed by cutting conduction polymer to shape and forming plastic into a flat bag with outlet ports in strategic locations.

Micro stimulators may be purchased or constructed in the same manner heart pacemakers have been made since the 1960's. Micro infusion pumps can be purchased or produced similar to how they have been produced for drug, insulin, and pain medication delivery since the 1970's. The programming computer can be standard laptop computer. The programming wand customary to wireless programming wands may be used to program heart pacers.

Any one of the protein expression signals work well on their own for organ regeneration, but they work better together. SDF-1 is the most powerful regeneration protein followed by IGF-1.

Wireless, single lumen infusion pacing lead or infusion conduction wide array patch may all be used to deliver the regeneration signals and substances to the organ of interest to be treated or they may be used in combination.

A re-charging wand for use herein is preferably similar to the pacemaker re-charging wand developed by Alfred Mann in the early 1970's for recharging externally implantable pacemakers.

Figure 21:
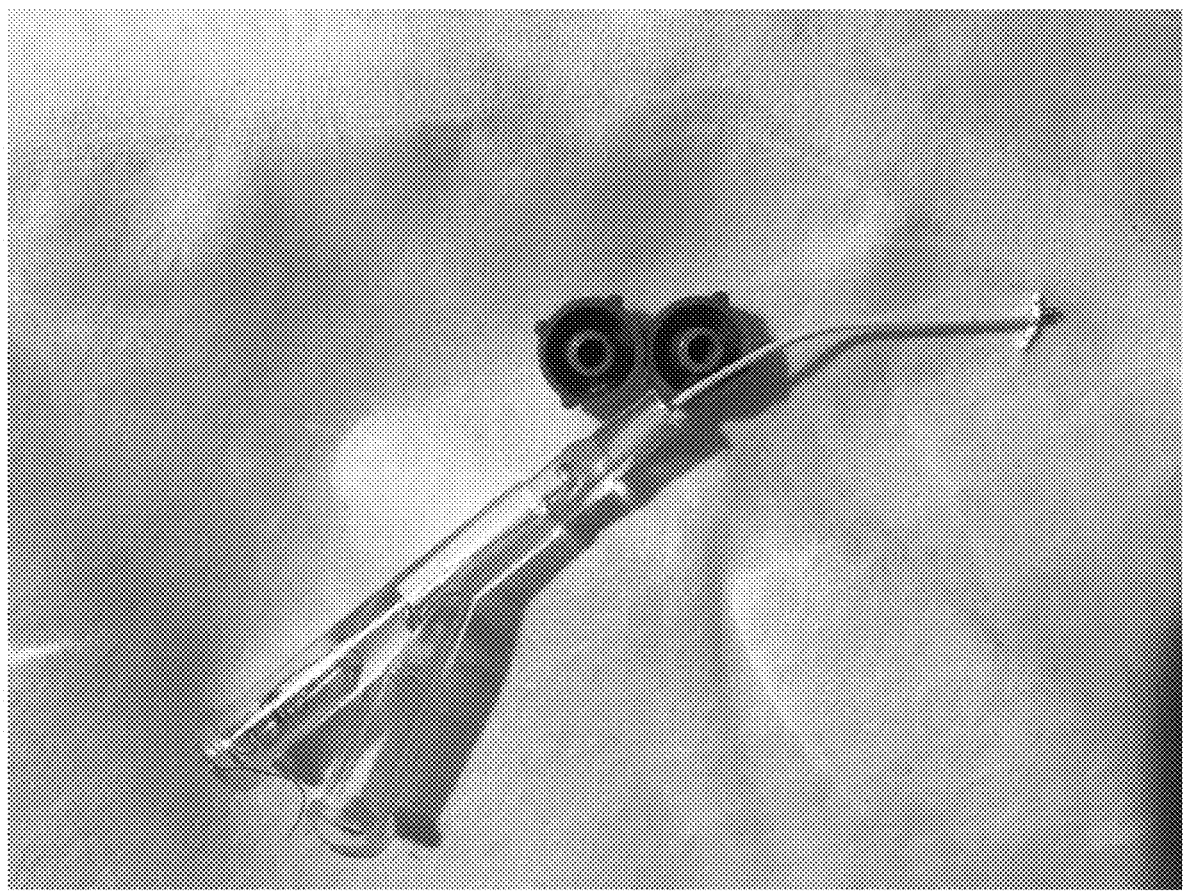
FIG. 21 depicts a combination bioelectric stimulation and stem cells and growth factors infusion catheter.

FIG. 21 depicts a combination bioelectric stimulation and stem cell and growth factor(s) infusion catheter usable with the described system.

Figure 22:
FIG. 22 is a close up view of the conductive and infusion cork screw tip for use with the catheter system of FIG. 21.

A corkscrew tip may be of a standard type utilized to secure most heart pacemakers in heart tissue. Wireless delivery of the signal or electro-acupuncture needle delivery is included. FIG. 22 is a close up of the conductive and infusion cork screw tip for getting deep into target tissue. The tip includes suture tabs for even more secure fixation to the target organ.

Additionally, the micro stimulator and micro pump and regeneration composition and bioelectric signaling programming may be used to generate tissue(s) and/or organ(s).

A preferred composition includes adipose-derived cells (or bone marrow derived MSCs or any pluripotent stem cell, such as iPS cells) and growth factor mix which should include (SDF-1, IGF-1, EGF, HGF, PDGF, VEGF, eNOS, activin A, activin B, follistatin, relaxin, GDF-10, GDF-11 and tropoelastin plus selected exosomes (miR-146a, miR-294, mES-Exo) plus selected alkaloids (harmine and tetra-hydroharmine) plus selected anti-inflammatory factors plus nutrient hydrogel (IGF-1, SDF-1, HGF plus FGF) plus organ specific matrix. For regenerating muscle, one includes into the composition skeletal muscle or cardiac muscle-derived cells. Also, preferably included are amniotic fluid, placenta, or cord blood when available.

For human use, longer repeat doses are needed and a natural release from a patient's own electrically stimulated cells leads to successful human heart regeneration. For example, the described signals for follistatin release match more closely with the natural low voltage signals in the human body.

There are three compositions, i.e., a basic composition, an intermediate composition, and an advanced composition. The basic composition includes MSCs or adipose derived cells, amniotic fluid, and myoblasts. The intermediate composition includes the ingredients of the basic composition together with a cocktail of growth factors (Follistatin rich). The advanced composition is adipose-derived or bone marrow-derived stem cells (MSCs), endothelial progenitor cells, selected growth factors cocktail, selected exosomes, selected Micro RNAs, selected alkaloids, selected anti-inflammatory agents, nutrient hydrogel, organ specific matrix, amniotic fluid (240 growth factors), and cardiac derived cells or immature myoblasts.

The concentration of cells in the compositions is preferably about 50,000,000 cells/ml. The amniotic fluid is preferably as described in Pierce et al. "Collection and characterization of amniotic fluid from scheduled C-section deliveries," *Cell Tissue Bank, DOI* 10.1007/s10561-016-9572-7 (Springer, 2012) and is available from Irvine Scientific.

In certain embodiments, an organ regeneration mixed composition (e.g., a cardio angiogenic and cardio myogenic "cocktail" for heart treatment/regeneration) is loaded into a micro infusion pump (or in the case of limb salvage injected directly in the patient's leg with a needle and syringe). The pump may be refilled, e.g., weekly to achieve a slow, timed infusion delivery of the composition to the heart scar tissue. Administration of the composition(s) is combined with bioelectric stimulation to control the release of more than twelve regeneration promoting proteins. Treatment times for assisting the heart may last 36 months.

Bioelectric stimulation can be done with the described microstimulator, which has a pacing infusion lead with a corkscrew lead placed/attached at, e.g., the center of heart scar tissue. The microstimulator is actuated and runs through programmed signals to signal the release of, e.g., SDF-1 and a differentiation signal. Described is a method of activating a tissue to differentiate a stem cell or to stimulate the tissue to produce a protein. The protein is selected from the group consisting of insulin-like growth factor 1 ("IGF1"), epidermal growth factor ("EGF"), hepatocyte growth factor ("HGF"), platelet-derived growth factor ("PDGF"), endothelial NOS ("eNOS"), vascular endothelial growth factor ("VEGF"), activin A, activin B, receptor activator of nuclear factor kappa-B ligand ("RANKL"), osteoprotegerin ("OPG"), tumor necrosis factor alpha ("TNF A"), follistatin, interleukin 6 ("IL-6"), hypoxia-inducible factor 1-alpha ("HIF-1-alpha"), and tropoelastin, the method including: stimulating the, e.g., human tissue with an electrical signal appropriate for the protein and tissue.

In such a method, when the electrical signal includes (within 15%): 0.1 V applied at a frequency of about 50 Hz with a duration of about three (3) minutes (wherein the electrical signal is as measured three (3) mm deep into the tissue), the protein produced is VEGF.

In such a method, when the electrical signal includes (within 2%): 200 picoamps for about 10 seconds for about one (1) hour and the pulse has an amplitude of about 5 volts and a width of about 0.5 milliseconds for about 1 hour, with a duration of about one (1) minute (wherein the electrical signal is as measured three (3) mm deep into the tissue), stem cells differentiate.

In such a method, when the electrical signal includes (within 15%): 10 V at 50 Hz and 100 Hz for about 12 hours each (duration 1 minute) (wherein the electrical signal is as measured three (3) mm deep into the tissue), the protein produced is follistatin.

In such a method, when the electrical signal includes (within 15%): 3.5 V stimulation in 10 second bursts, 1 burst every 30 seconds at a frequency of about 50 Hz (duration 5 minutes) (wherein the electrical signal is as measured three (3) mm deep into the tissue), the protein produced is HGF.

In such a method, when the electrical signal includes (within 15%): 3 mV with a frequency of about 22 Hz, and a current of 1 mA for about fifteen (15) minutes and 3 ma for about fifteen (15) minutes (duration 5 minutes) (wherein the electrical signal is as measured three (3) mm deep into the tissue), the protein produced is IGF-1.

In such a method, when the electrical signal includes (within 15%): 0.06 V with 50 Hz alternating electrical field and a current of about 1 mA for about fifteen (15) minutes and 3 mA for about fifteen (15) minutes (duration 2 minutes) (wherein the electrical signal is as measured three (3) mm deep into the tissue), the protein produced is tropoelastin.

In such a method, when the electrical signal includes (within 15%): alternating high-frequency (HF) and medium-frequency signals (MF), symmetric, biphasic, trapezoid pulses, with 400-µs pulse duration and 1.5/1-s ramp-up/ramp-down duration, respectively (wherein the electrical signal is as measured three (3) mm deep into the tissue), the protein produced is eNOS. In such a method, when the HF consists of about 75 Hz pulses with six (6) seconds on and 21 seconds off for about fifteen (15) minutes. In such a method, when the MF consists of about 45 Hz pulses with 5 seconds on 12 seconds off for about fifteen (15) minutes followed by stimulation duration set as 20 minutes. In such a method, when the electrical signal includes (within 15%): 1 Hz stimulation, stimulation applied for about nine (9) seconds, followed by a one (1) second silent period, a total of about 1080 stimulations for about 20 minutes. In such a method, when the electrical signal includes (within 15%): 20 Hz stimulation, stimulation applied for about two (2) seconds, followed by silent period for about 28 seconds, a total of about 1600 stimulations for about 20 minutes (duration 2 minutes).

In such a method, when the electrical signal includes (within 15%): 6 mV at 150 Hz Monophasic square wave pulse 0.1 ms in duration current of fifteen (15) mA for about fifteen (15) minutes (duration two (2) minutes) (wherein the electrical signal is as measured three (3) mm deep into the tissue), the protein produced is Activin B.

In such a method, when the electrical signal includes (within 15%): 10 V/cm, pulse-width 180 µs, 500 Hz (duration nine (9) minutes) (wherein the electrical signal is as measured three (3) mm deep into the tissue), the protein produced is EGF.

For example, up-regulation of RANKL, IGF-1, VEGF, and SDF-1 was achieved in cardiomyocytes using such signals. Up-regulation of SDF-1 was achieved in pig heart. Up-regulation of VEGF, endothelial NOS ("eNOS"), hypoxia-inducible factor 1-alpha ("HIF-1-alpha"), and IL-6 was achieved in eye cells. Up-regulation of RANKL and osteoprotegerin ("OPG") was achieved in bone, tooth and gum.

Also described is a method of activating a tissue to produce stromal cell-derived factor 1 ("SDF1"), the method including: stimulating the (e.g., human) tissue with an electrical signal, wherein the electrical signal includes (within 15%): 30 pulses per second with a voltage of about 3.5 mV, and successively alternating currents of about 700 to 1500 picoamps for about one minute, and again with 700 to 1500 picoamps for about one minute and stimulated with current of about 0.25 mA, pulse duration of about 40 pulses/s, pulse width of about 100 µs, wherein the electrical signal is as measured three (3) mm deep into the tissue.

Further described is a method of activating a tissue to attract a stem cell, the method including: stimulating the (e.g., human) tissue with an electrical signal, wherein the electrical signal includes (within 2%): fifteen (15) mV and a current of about 500 picoamps at 70 pulses per minute for about three (3) hours and 20 pulses per minute, a pulse amplitude of from about 2.5-6 volts, and a pulse width of from about 0.2-0.7 milliseconds for about three (3) hours for about three (3) minutes, wherein the electrical signal is as measured three (3) mm deep into the tissue.

A combination bioelectric stimulator that controls release in the scarred heart of SDF-1, IGF-1, HGF, EGF, eNOS, VEGF, Activin A and B, follistatin, tropoelastin, GDF-10, GDF-11 and Neurogenin 3 combined with repeat delivery of a mixed stem cell and growth factor cardiac matrix composition via an implantable re-fillable micro infusion pump may be advantageously used.

In some cases, SDF-1 recruits via a presumed homing signal new reparative stem cells to the damaged organ. VEGF causes new nutrient and oxygen producing blood vessels to grow into the area being treated. IGF-1 repairs damaged cells, tissues and organs. Follistatin repairs damaged muscle. Tropoelastin adds elasticity to treated tissues making them more compliant. HGF aides in all repair processes and in the specific case of the heart regeneration reduces the risk of arrhythmias. All of these proteins work together to fully regenerate an organ over time.

The healing process can be accelerated with the use of a micro infusion pump that is filled with various types of stem cells and growth factors and in some cases drugs.

In certain embodiments relating to the treatment of cancer and tumors, described is a method of inhibiting the growth of cancer cells in a target region, wherein the method includes treating the cancer cells with an anti-cancer drug; and applying an electric field to the target region for a period of time, wherein the electric field has frequency and field strength characteristics selected to inhibit the growth of cancer cells in the target region. In such a method, in the applying step, the field may be applied in at least two different directions in an alternating sequence.

In such a method, the drug dosage may be less than 20% of a standard dosage for the drug.

In such a method, the period of time is typically at least 24 hours.

In such a method, the field strength is typically at least 1 V/cm.

In such a method, the drug typically comprises at least one of paclitaxel, doxorubicin, cyclophosphamide, and cisplatin. In such a method, the field strength is typically at least 1 V/cm and the period of time is at least 24 hours.

Also described in certain embodiments is a method of killing or inhibiting the growth of cancer cells in a target region, wherein the method includes applying an electric field to the target region for a period of time while the cancer cells are being treated with an anti-cancer drug, wherein the electric field has a field strength in the target region of at least 1 V/cm. In such a method, the drug dosage is less than 20% of a standard dosage for the drug. In such a method, the period of time is at least 24 hours. In such a method, the drug comprises at least one of paclitaxel, doxorubicin cyclophosphamide, and cisplatin. In such a method, the field strength is between 1 V/cm and 5 V/cm and the period of time is at least 24 hours. In such a method, in the applying step, the field is applied in at least two different directions in an alternating sequence. Typically, the drug comprises cyclophosphamide, and typically, the period of time is at least 6 hours.

What follows are preferred signals from the stimulator. For example, described are two PDGF expression control signals, one low voltage and one higher voltage. The test tissue is sheep heart tissue. The test cells are mesenchymal stem cells.

30% PDGF increase >3 V/cm, 10 Hz, 2 micro amps (0.000002 amps) and the pulse duration 0.2 ms.

230% PDGF increase >20 V/cm 100 Hz, 0.25 mA (2.5e−7 amps) and pulse duration of 40 pulses/s, width of 100 µs.

40 minute treatment cycles 2 times a week for 4 weeks and then 3 times a week for 12 weeks.

PDGF Signal: 20 V for 1 minute, 20 mV for 10 minutes, current of 0.25 mA, pulse duration of 40 pulses/s, pulse width of 100 µs, and frequency of 100 Hz for 5 minutes followed by 528 Hz for 3 minutes and 432 Hz for 3 minutes and 50 Hz for 3 minutes.

VEGF—Blood vessel sprouting growth: 0.1 V applied at a frequency of 50 Hz.

Duration 3 minutes.

SDF-1—Stem cell recruiting signal: 30 pulses per second with a voltage of 3.5 mV, and successively alternating currents of 700 to 1500 picoamps for one minute, and again with 700 to 1500 picoamps for one minute and stimulated with current of 0.25 mA, pulse duration of 40 pulses/s, pulse width of 100 µs, and frequency of 100 Hz—each signal for 40 minutes to 8 hours a day for 2 to 36 months as needed for ideal results. Duration 7 minutes.

Stem cell proliferation signals: 15 mV and a current of 500 picoamps at 70 pulses per minute for 3 hours and 20 pulses per minute, a pulse amplitude of from 2.5-6 volts, and a pulse width of from 0.2-0.7 milliseconds for 3 hours. Duration 3 minutes.

Stem cell differentiation signals to become muscle: 200 picoamps for 10 seconds for 1 hour and the pulse has an amplitude of 5 volts and a width of 0.5 milliseconds for 1 hour. Duration 1 minute.

Another method is to reverse polarity and drop the voltage.

Follistatin -(muscle growth) production signal: 10 V at 50 Hz and 100 Hz 0.25 mA. Duration 1 minute.

HGF -Hepatocyte growth factor (arrhythmia reduction) signal: 3.5 V stimulation in 10 second bursts, 1 burst every 30 seconds at frequency 50 Hz. Duration 5 minutes.

IGF-1: 3 mV with electric frequency of 22 Hz, and electric current of 1 mA for 15 minutes and 3 mA for 15 minutes. Duration 5 minutes.

Tropoelastin: 0.06 V with 50 Hz alternating electrical field and electric current of 1 mA for 15 minutes and 3 mA for 15 minutes. Duration 2 minutes.

RANKL/TNF Alpha nuclear factor-kappa B (NF-κB) ligand/TNF Alpha: 3 mV at 2/100 Hz alternating frequency with current of 3 mA followed by 15 Hz, 1

Gauss EM field, consisting of 5-millisecond bursts with 5-microsecond pulses followed by 200-µs pulse duration at 30 Hz and with current amplitude of 140 mA. (Optional use depending on application.)

eNOS: Alternating high-frequency (HF) and medium-frequency signals (MF): Symmetric, biphasic, trapezoid pulses, with 400-µs pulse duration and 1.5/1-s ramp-up/ramp-down duration, respectively. HF consisted of 75 Hz pulses with 6 second on-21 second off for 15 minutes. MF consisted of 45 Hz pulses with 5 second on-12 second off for 15 minutes. Followed by stimulation duration set as 20 minutes for both 1 Hz and 20 Hz stimulations. For 1 Hz stimulation, stimulation is applied for 9 seconds, followed by a 1 second silent period, a total of 1080 stimulations for 20 min. For 20 Hz stimulation, stimulation is applied for 2 seconds, followed by silent period for 28 seconds, a total of 1600 stimulations for 20 min. Duration 2 minutes.

Activin B: 6 mV at 150 Hz Monophasic square wave pulse 0.1 ms in duration current of 15 mA for 15 minutes. Duration 2 minutes.

EGF—10 V/cm, pulse-width 180 µs, 500 Hz. Duration 9 minutes.

An exemplary bioelectric signal sequence suggested for heart regeneration in humans split into six phases is as follows.

Phase I—Prepare Scar ("soil prep"): 10 minutes
 IGF-1 signal 3 minutes
 PDGF signal 3 minutes
 HGF signal 2 minutes
 EGF signal 2 minutes
Phase II—Grow New Blood Vessels ("lay irrigation system"): 5 minutes
 VEGF signal—3 minutes
 SDF-1 signal—1 minute
 eNOS signal—1 minute
Phase III—Recruit and Inject Stem Cells ("plant"): 15 minutes
 SDF-1 signal—10 minutes
 PDGF-1 signal 5 minutes
Phase IV—Build Tissue ("grow"): 25 minutes
 Stem Cell Proliferation Signal—5 minutes
 Stem Cell Differentiation Signal—5 minutes
 Follistatin Signal—5 minutes
 Tropoelastin Signal—5 minutes GDF-10-2 minutes
GDF-11-3 minutes
Phase V—Post Tissue Growth Maintenance ("fertilize"): 30 minutes
VEGF—3 minutes
EGF—2 minutes
eNOS—2 minutes
HGF—5 minutes
PDGF—3 minutes
Tropoelastin—5 minutes
Relaxin—5 minutes
Follistatin—5 minutes
Phase VI—Protect Against Enemies ("pesticides"): 10 minutes
Activin A and B—5 minutes
IGF-1-5 minutes Results of Electrical Stimulation (ES) of Cells In Vitro IL-1 β: mRNA expression was up-regulated from 16 up to more than 400 times when cells were treated with 10 to 20 V between 3 and 20 hours.

IL-6: mRNA expression was up-regulated from 3 times—as soon as 15 minutes- to 10 times.

IL-8: mRNA expression was stimulated by 5 to 50 times.

HGF: mRNA expression was up-regulated by more than 10 times.

TNFα: mRNA expression was up-regulated by 9 to 24 times.

MMP9: mRNA expression was up-regulated 9 to 23 times with 3 and 24 hours of ES, respectively.

CCL2: mRNA expression was up-regulated 15 to 64 times.

CXCL5: mRNA expression up-regulated thousands of times.

CXCL10: mRNA expression up-regulated thousands of times.

A week after treatment, samples can be collected for morphometric evaluation by in-situ hybridization or RT-PCR.

FIGS. 6-20 are images of the corresponding signals with the name, voltage, and frequency of each signal written on each image. eNOS and differentiation signals were omitted due to of complexity or lack of frequency parameters. The signals are to be further defined in terms of current and frequency, not voltage and frequency as shown. The voltage delivered to the cells will be different for each tissue type, but with current all of the signals can be kept constant regardless of tissue type. The device should have a current driven signal (instead of voltage driven like most other devices).

Figure 6:
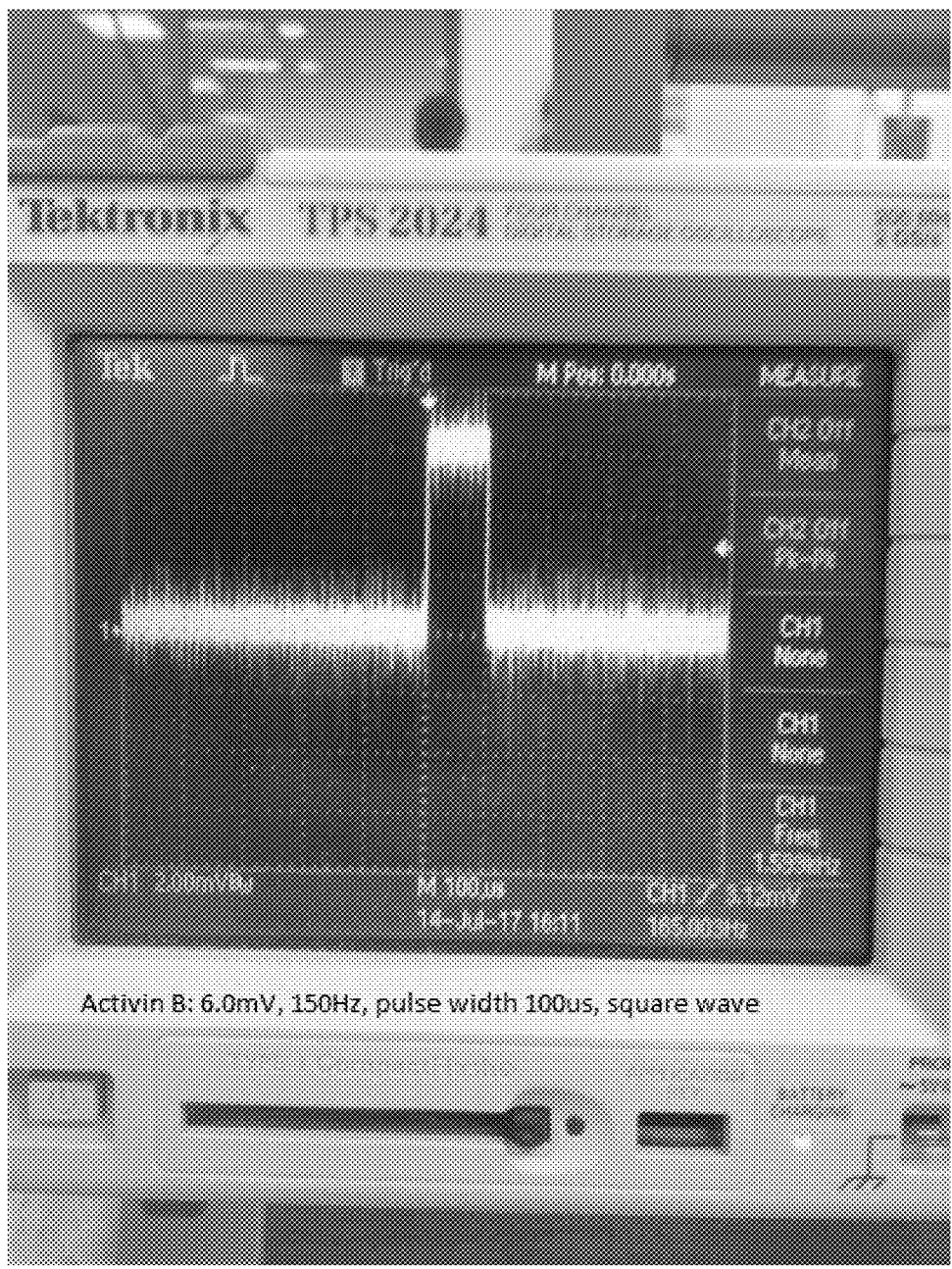
FIG. 6 depicts an image of the signal (voltage and frequency) associated with Activin B at 6.0 mV, pulse width 100 μs, square wave.
Figure 7:
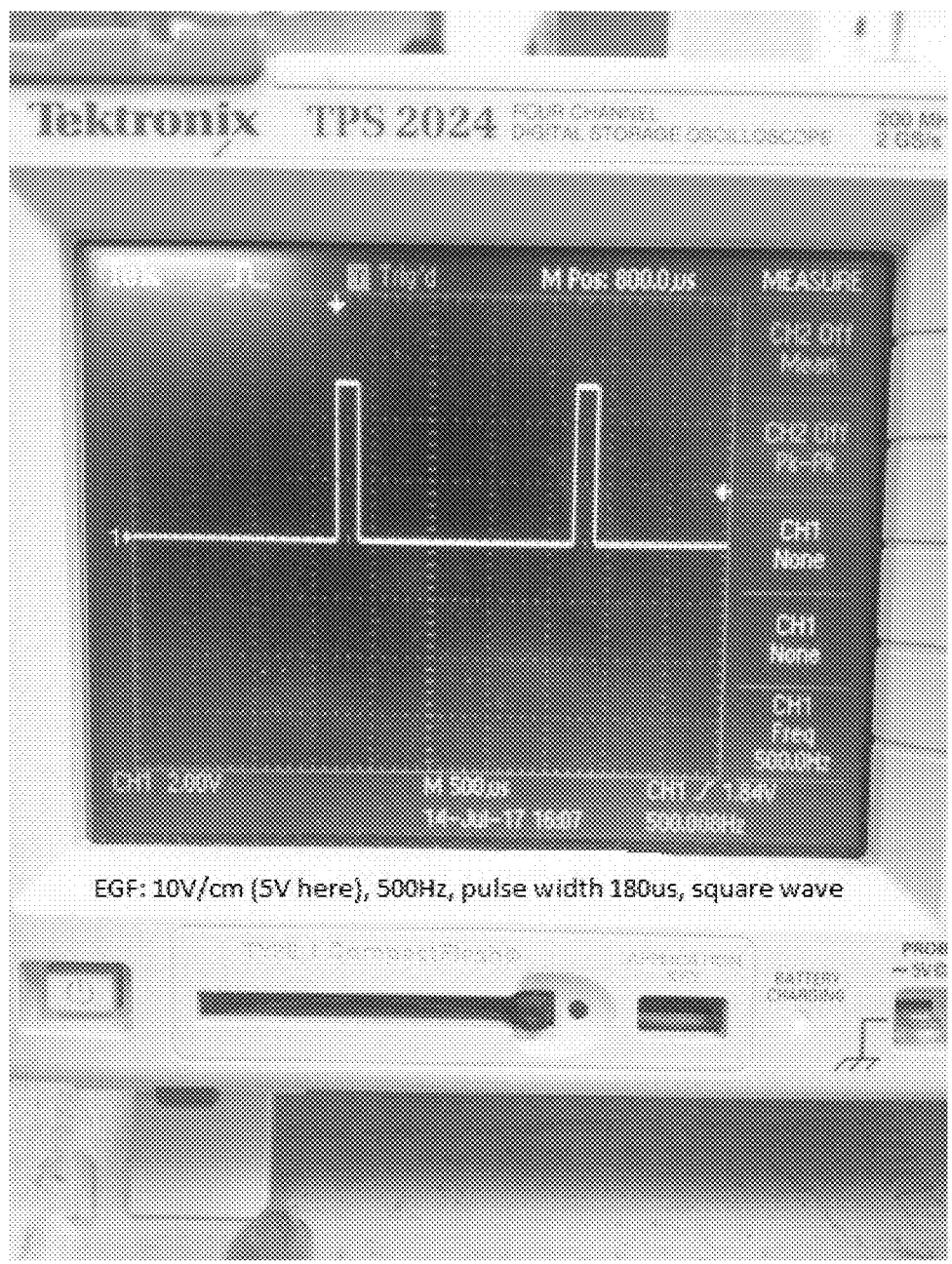
FIG. 7 depicts an image of the signal (voltage and frequency) associated with EGF at 10 V/cm (5 V here), 500 Hz, pulse width 180 μs, square wave.
Figure 8:
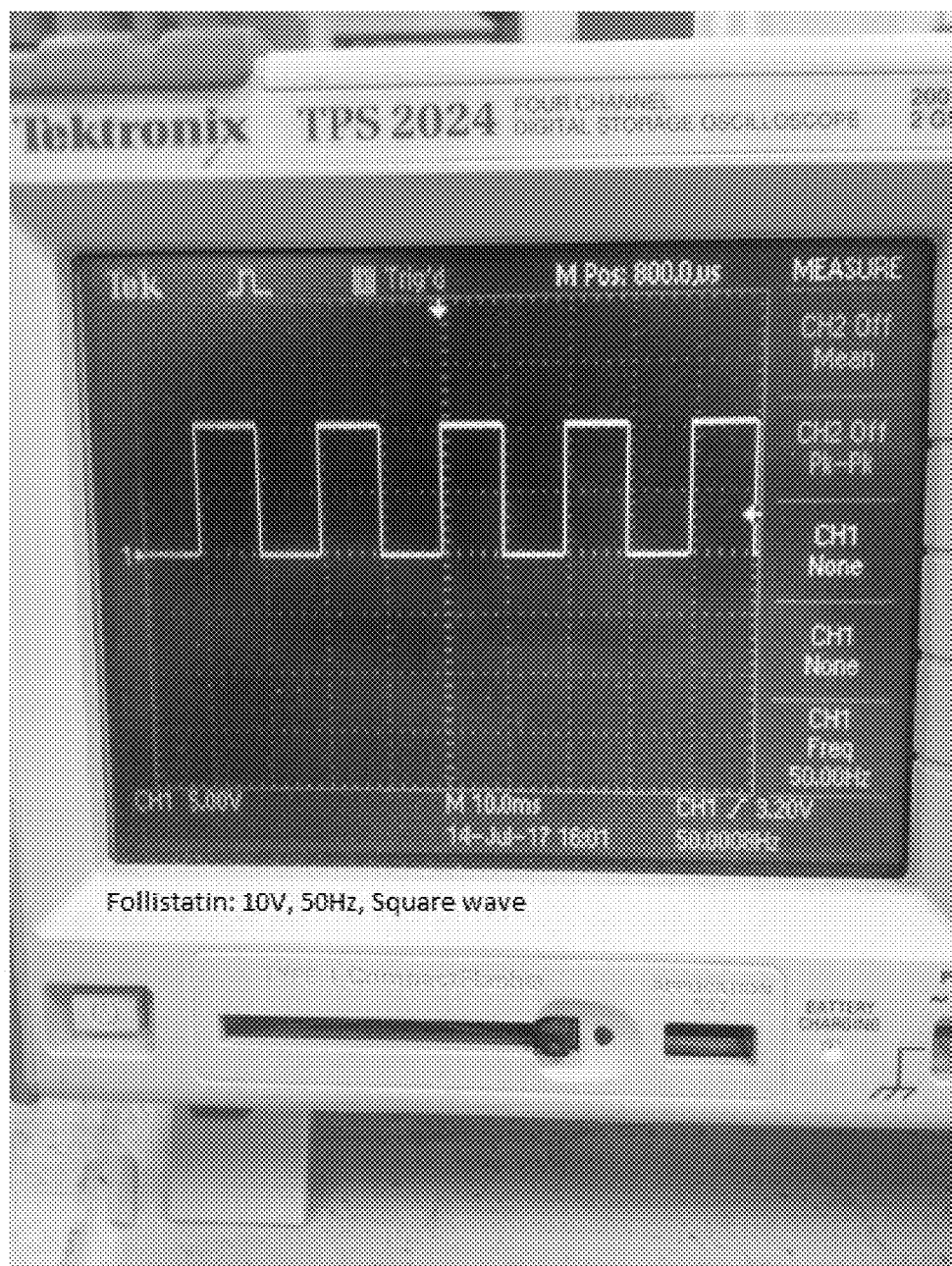
FIG. 8 depicts an image of the signal (voltage and frequency) associated with follistatin at 10 V/cm, 50 Hz, square wave.
Figure 9:
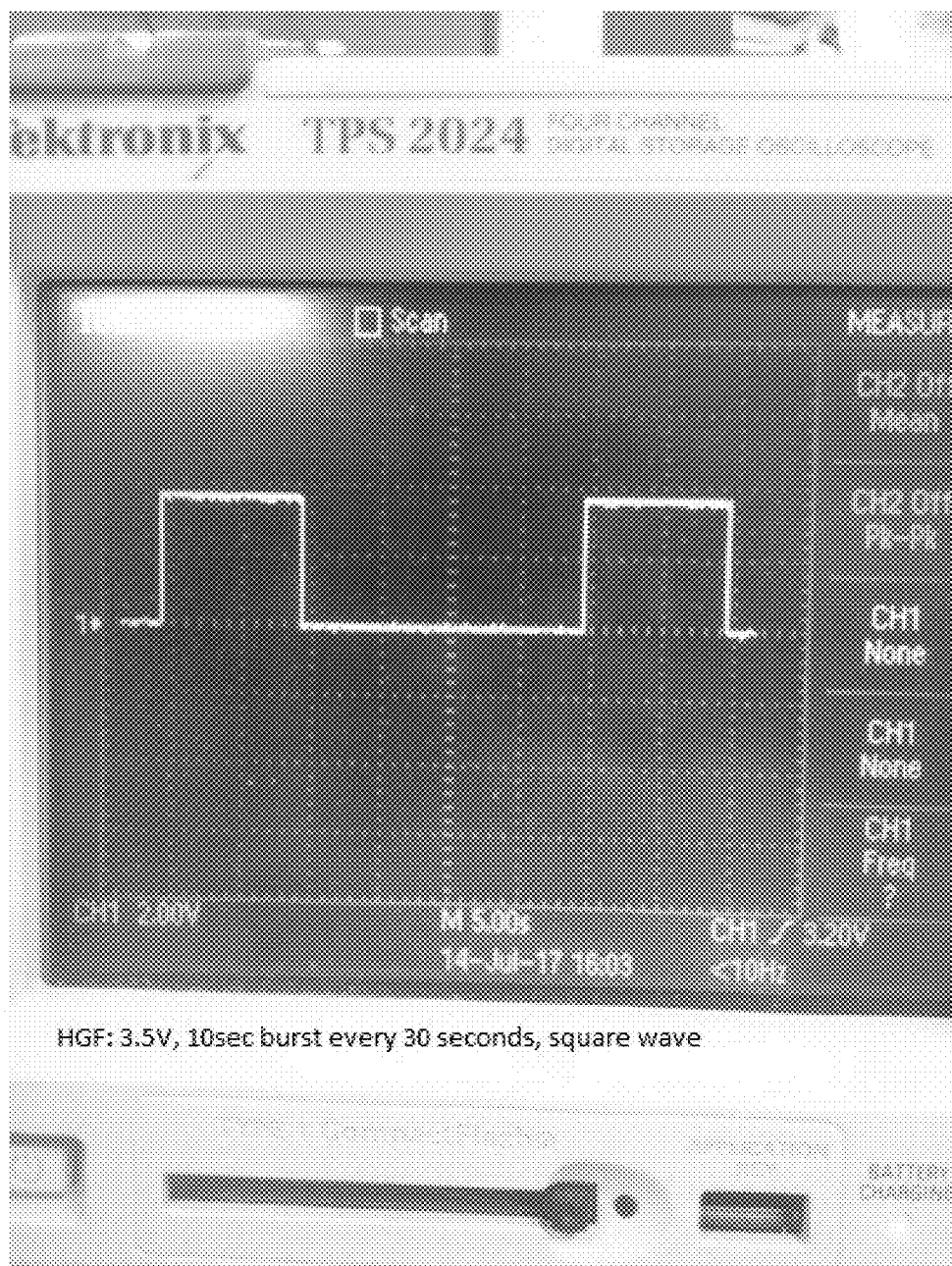
FIG. 9 depicts an image of the signal (voltage and frequency) associated with HGF at 3.5 V, 10 second burst every 30 seconds, square wave.
Figure 10:
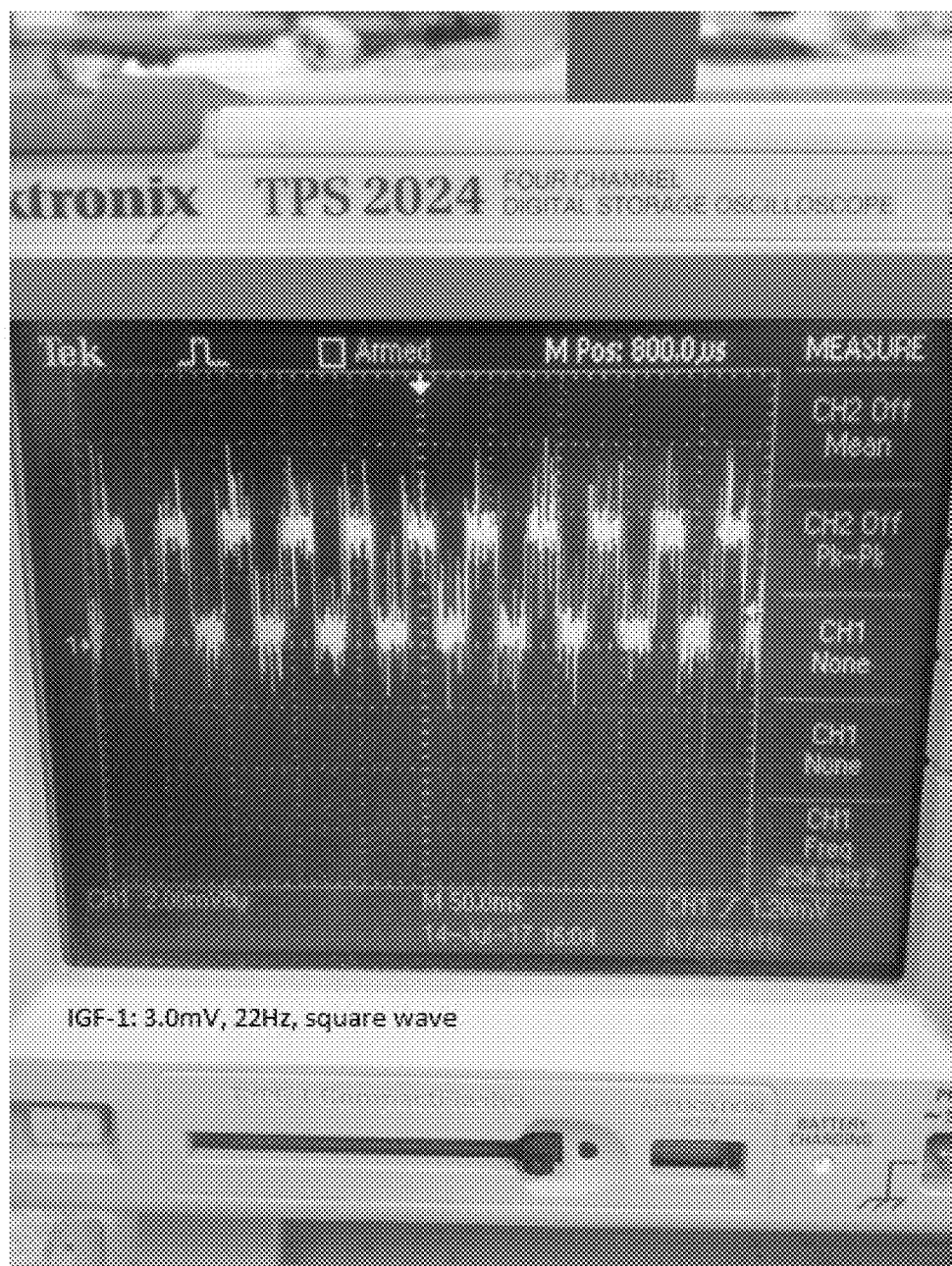
FIG. 10 depicts an image of the signal (voltage and frequency) associated with IGF-1: 3.0 mV, 22 Hz, square wave.
Figure 11:
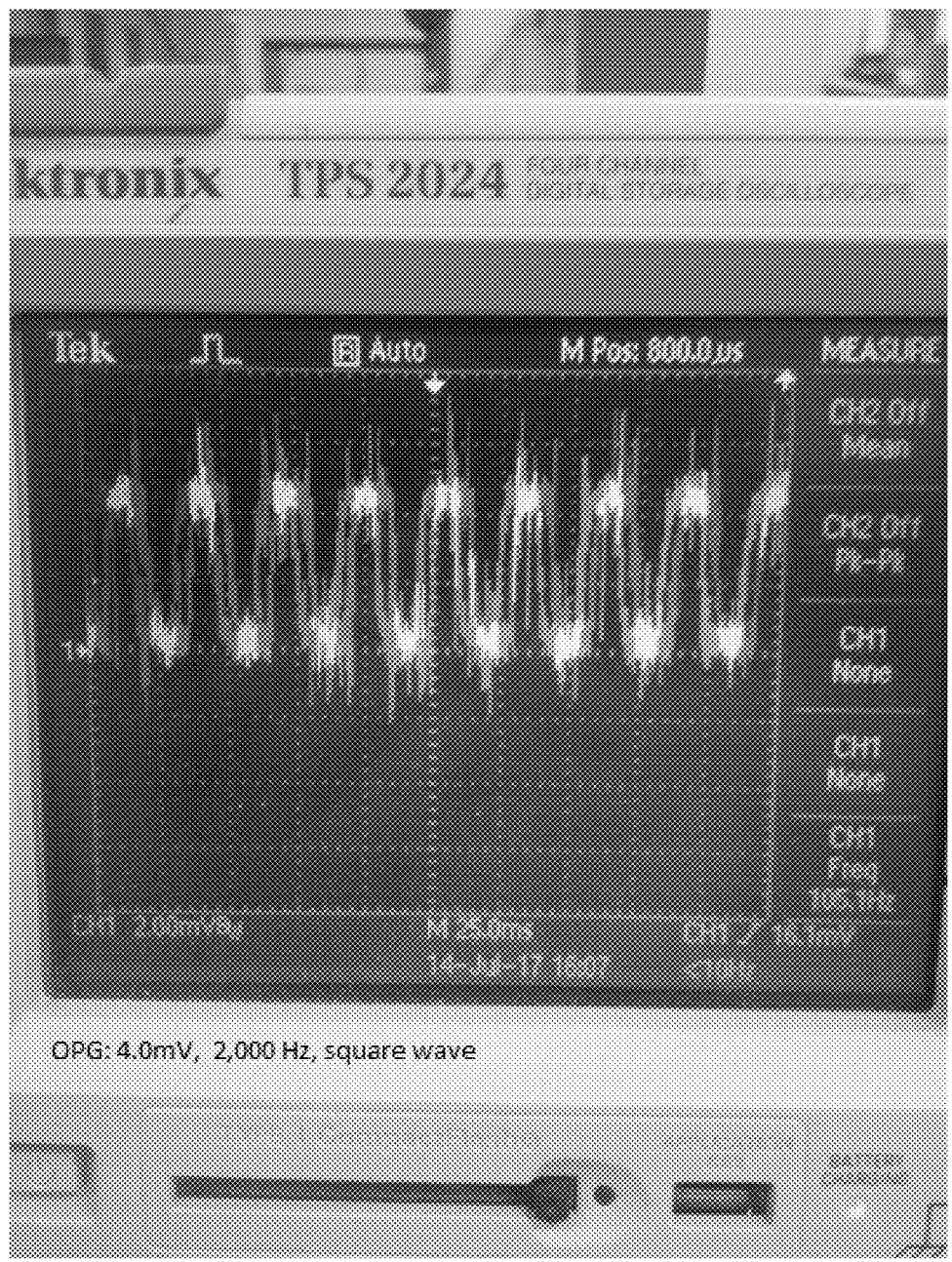
FIG. 11 depicts an image of the signal (voltage and frequency) associated with OPG: 4.0 mV, 2,000 Hz, square wave.
Figure 12:
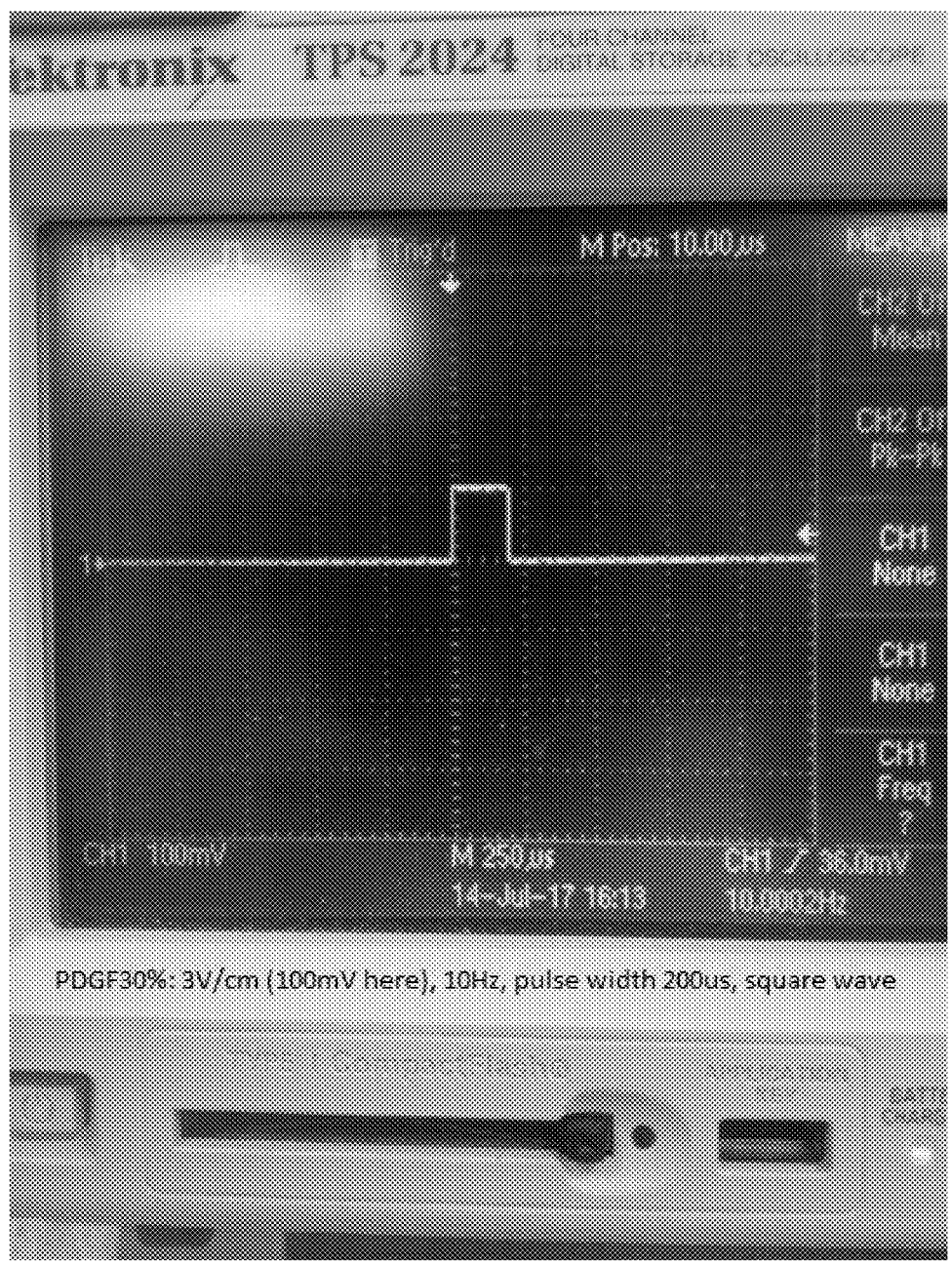
FIG. 12 depicts an image of the signal (voltage and frequency) associated with PDGF 30%: 3 V/cm (100 mV here), 10 Hz, pulse width 200 μs, square wave.
Figure 13:
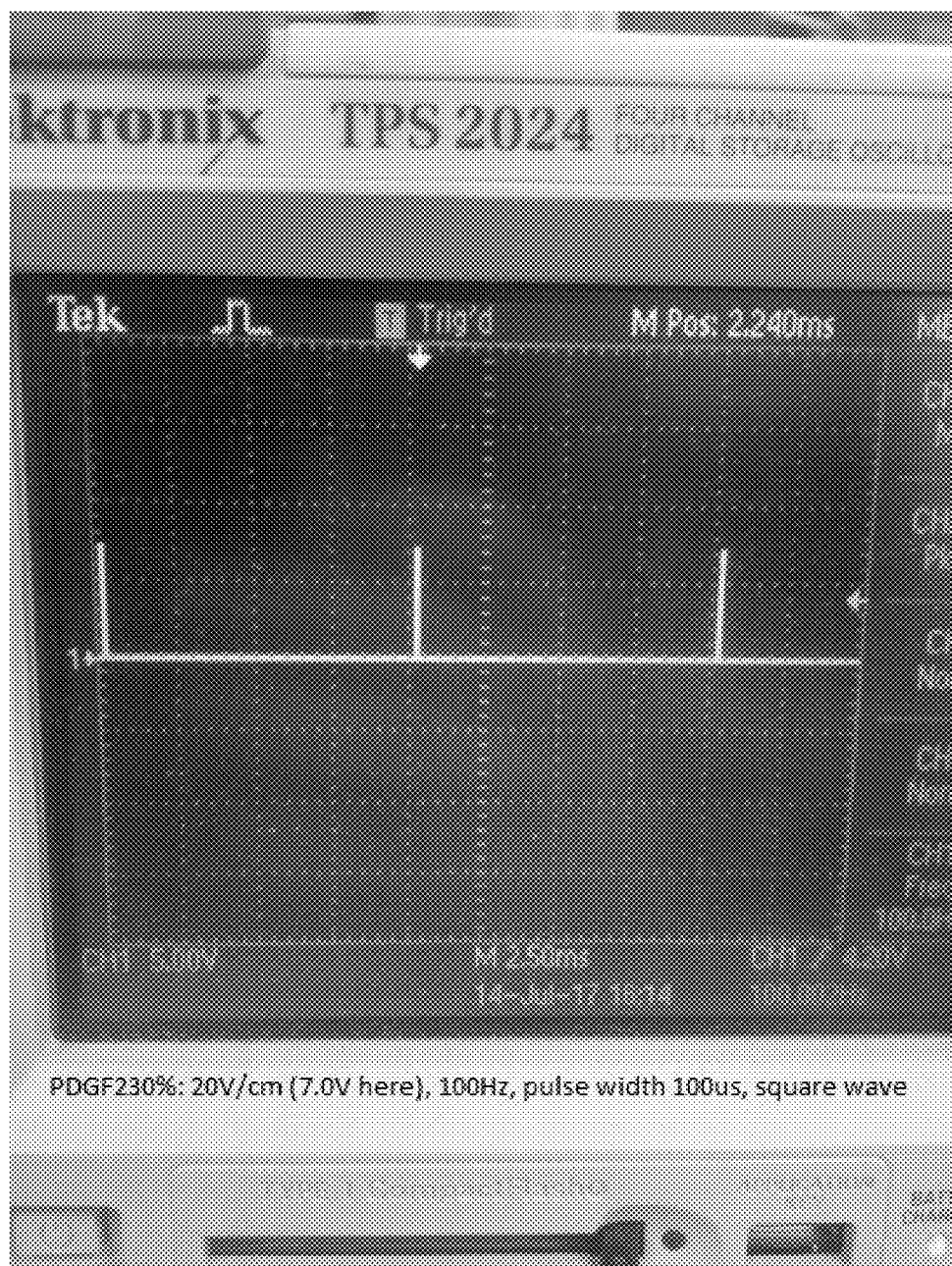
FIG. 13 depicts an image of the signal (voltage and frequency) associated with PDGF 230%: 20 V/cm (7.0 V here), 100 Hz, pulse width 100 μs, square wave.
Figure 14:
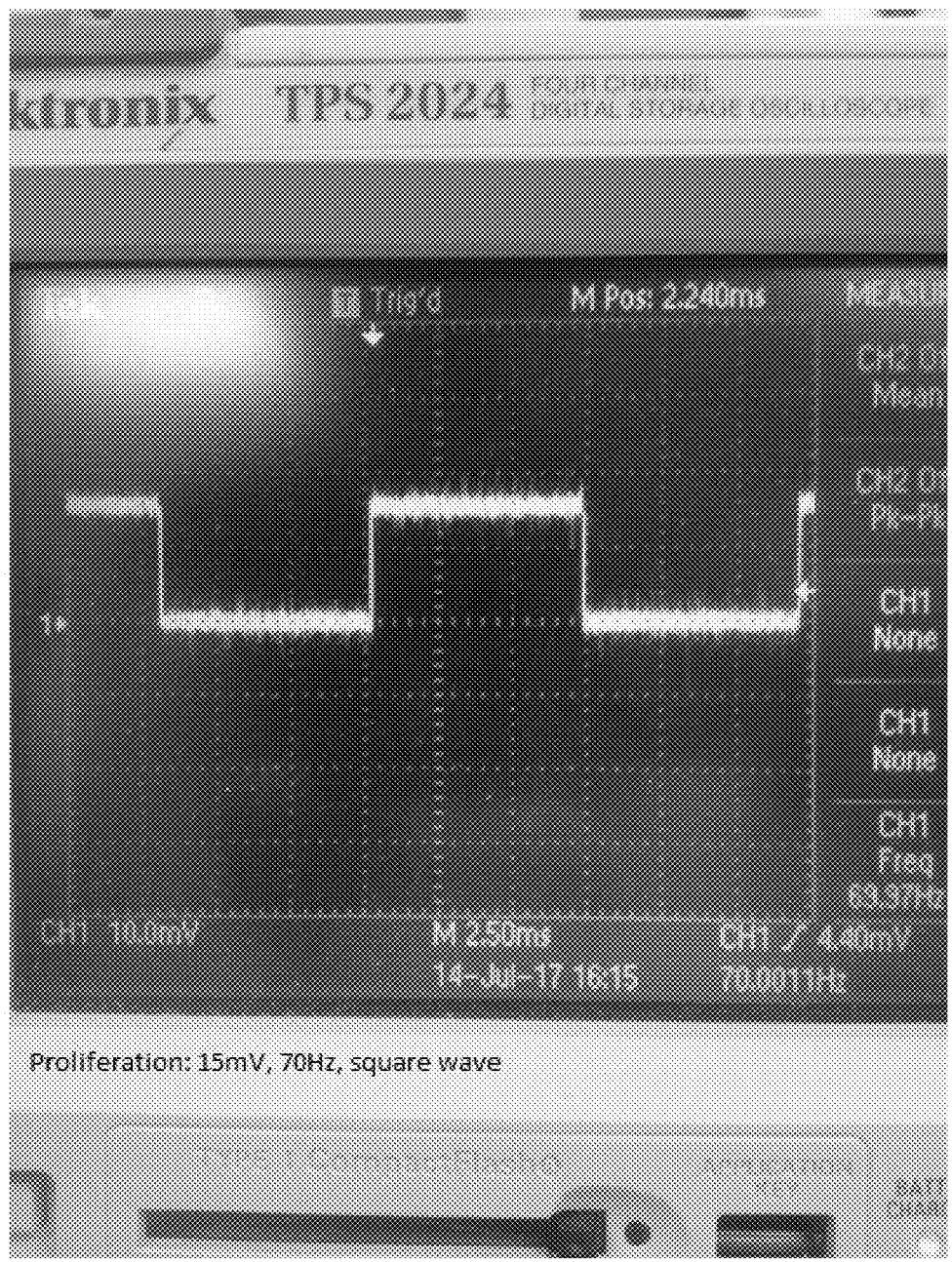
FIG. 14 depicts an image of the signal (voltage and frequency) associated with proliferation: 15 mV, 70 Hz, square wave.
Figure 15:
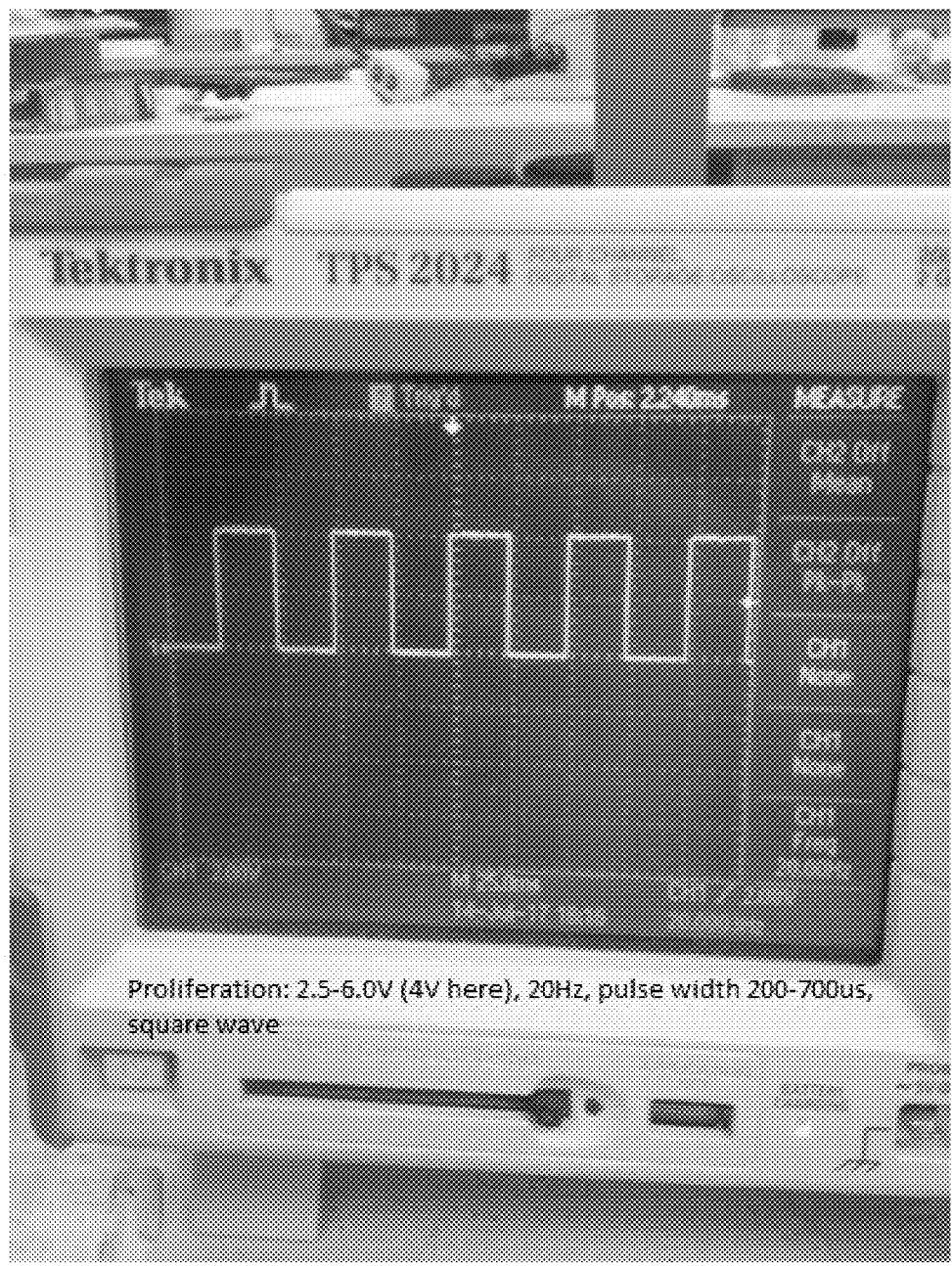
FIG. 15 depicts an image of the signal (voltage and frequency) associated with proliferation: 2.5-6.0 V (4 V here), 20 Hz, pulse width 200-700 μs, square wave.
Figure 16:
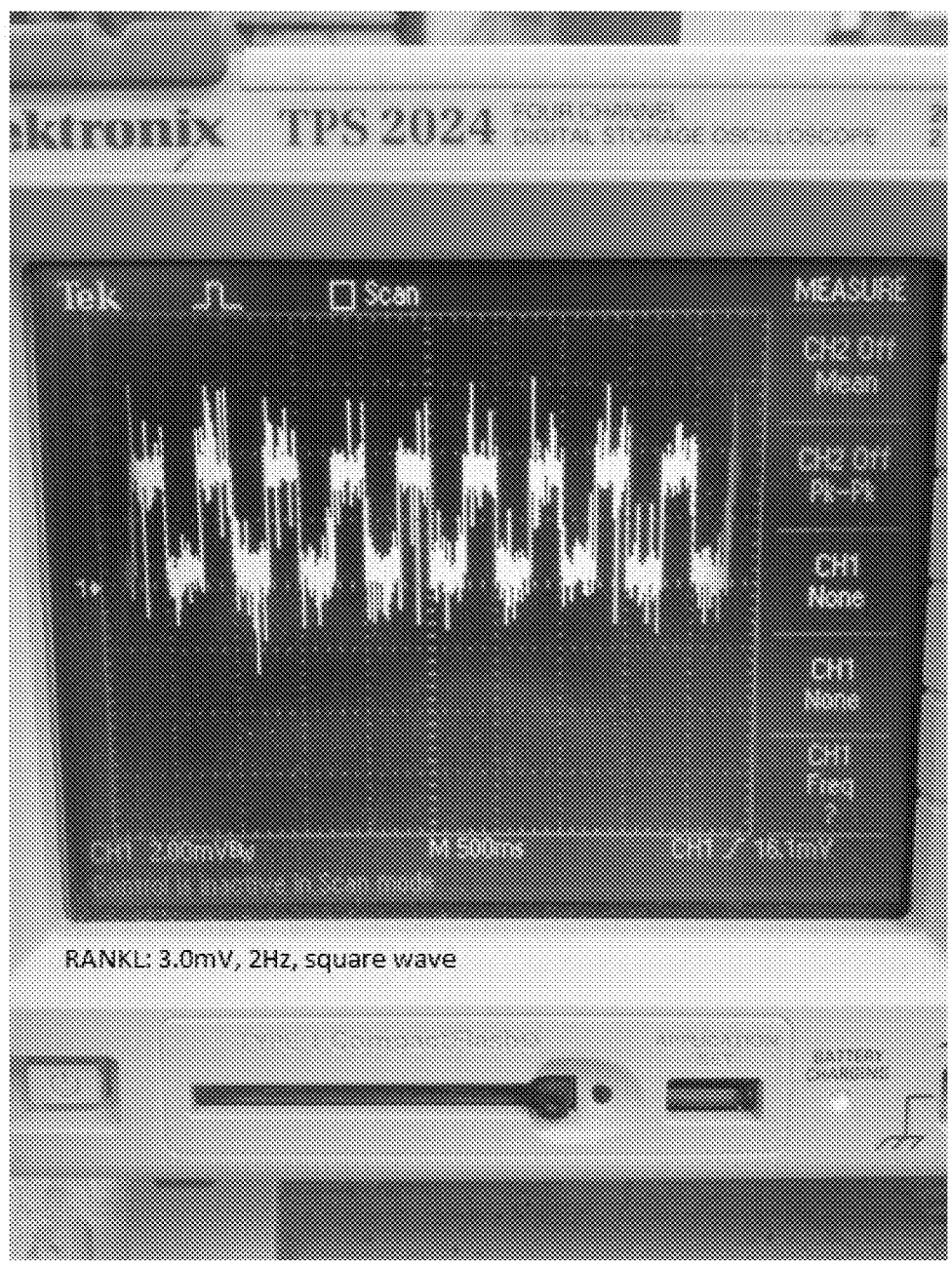
FIG. 16 depicts an image of the signal (voltage and frequency) associated with RANKL: 3.0 mV, 2 Hz, square wave.
Figure 17:
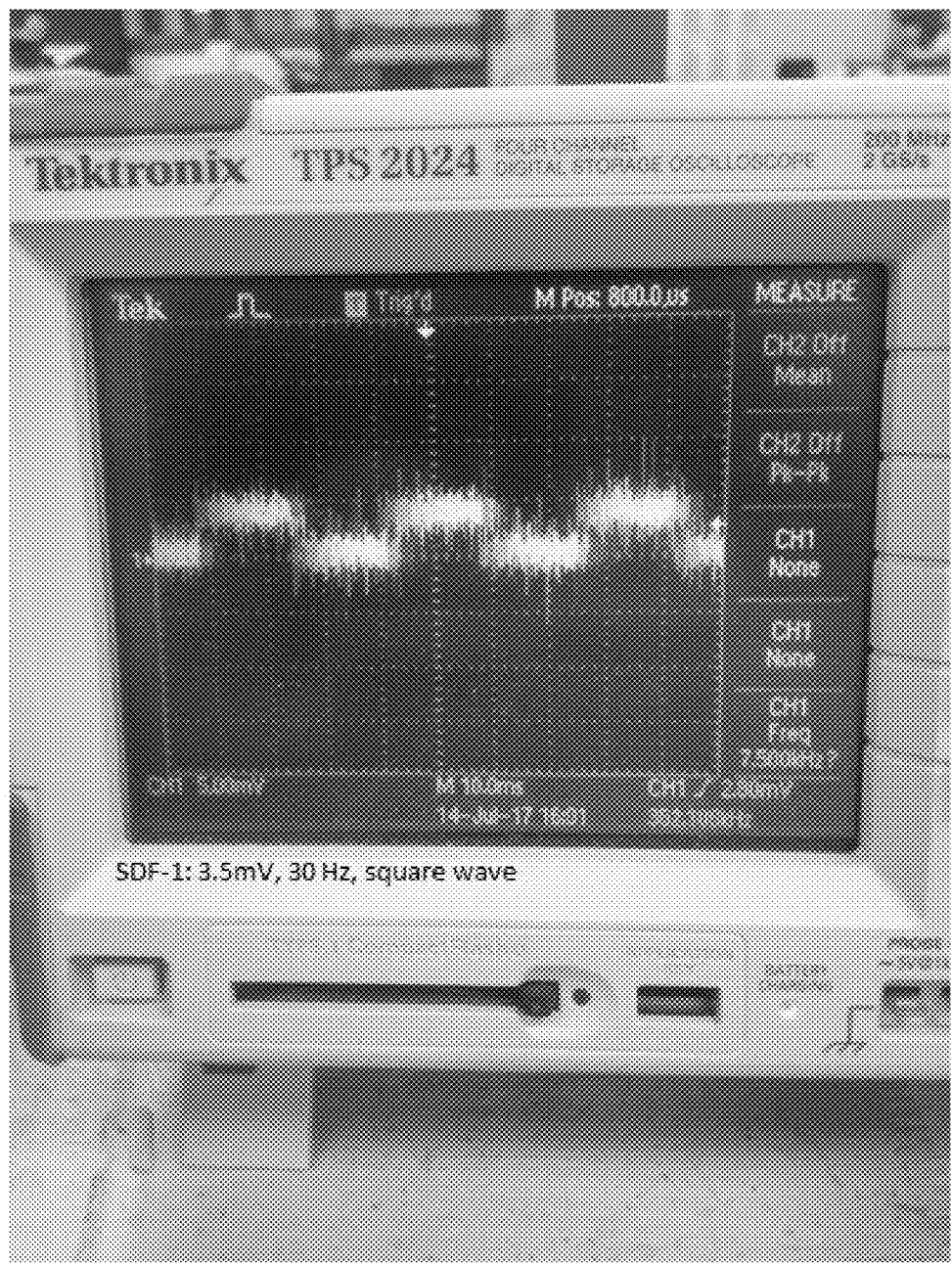
FIG. 17 depicts an image of the signal (voltage and frequency) associated with SDF-1: 3.5 mV, 30 Hz, square wave.
Figure 18:
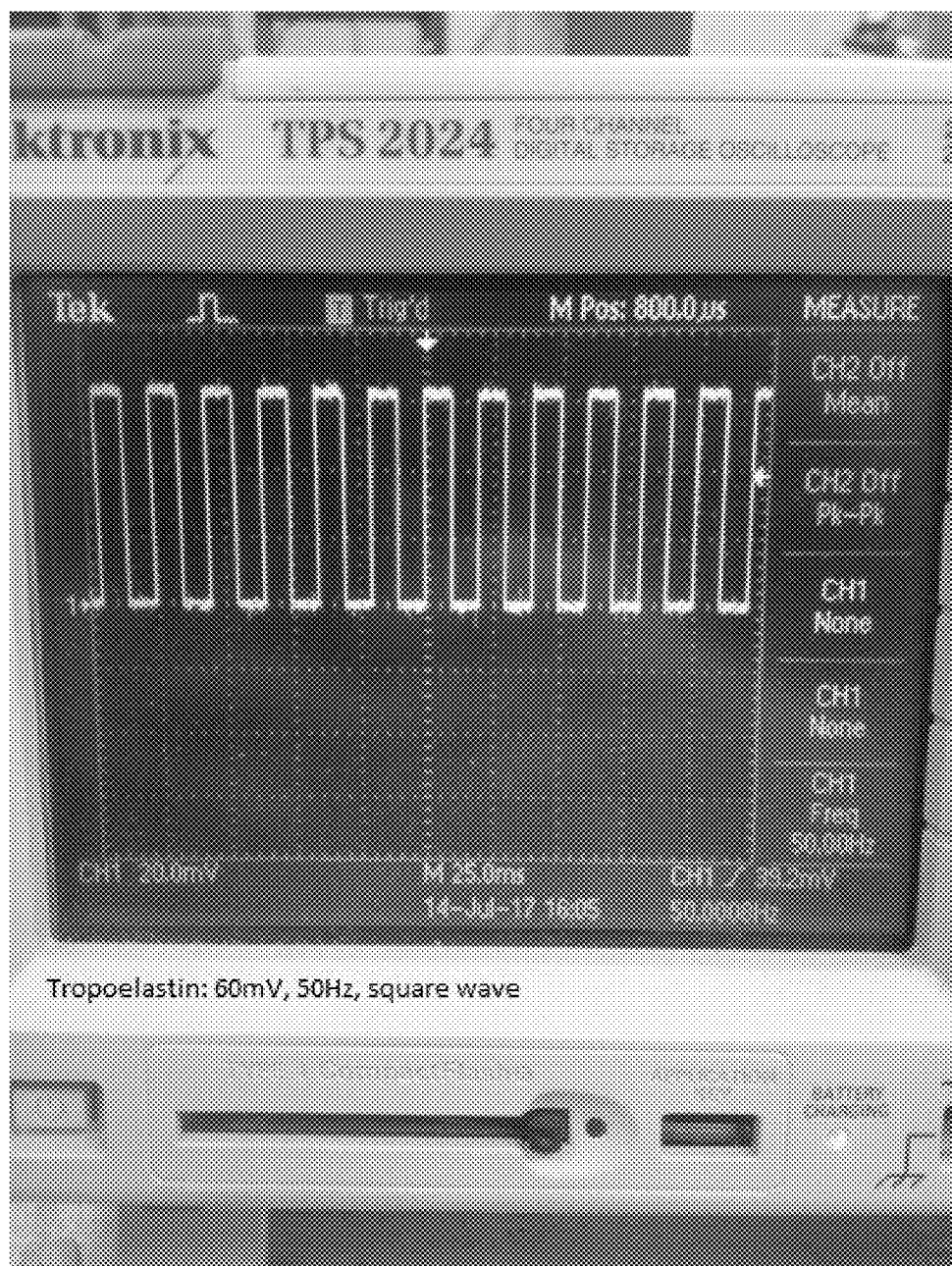
FIG. 18 depicts an image of the signal (voltage and frequency) associated with tropoelastin: 60 mV, 50 Hz, square wave.
Figure 19:
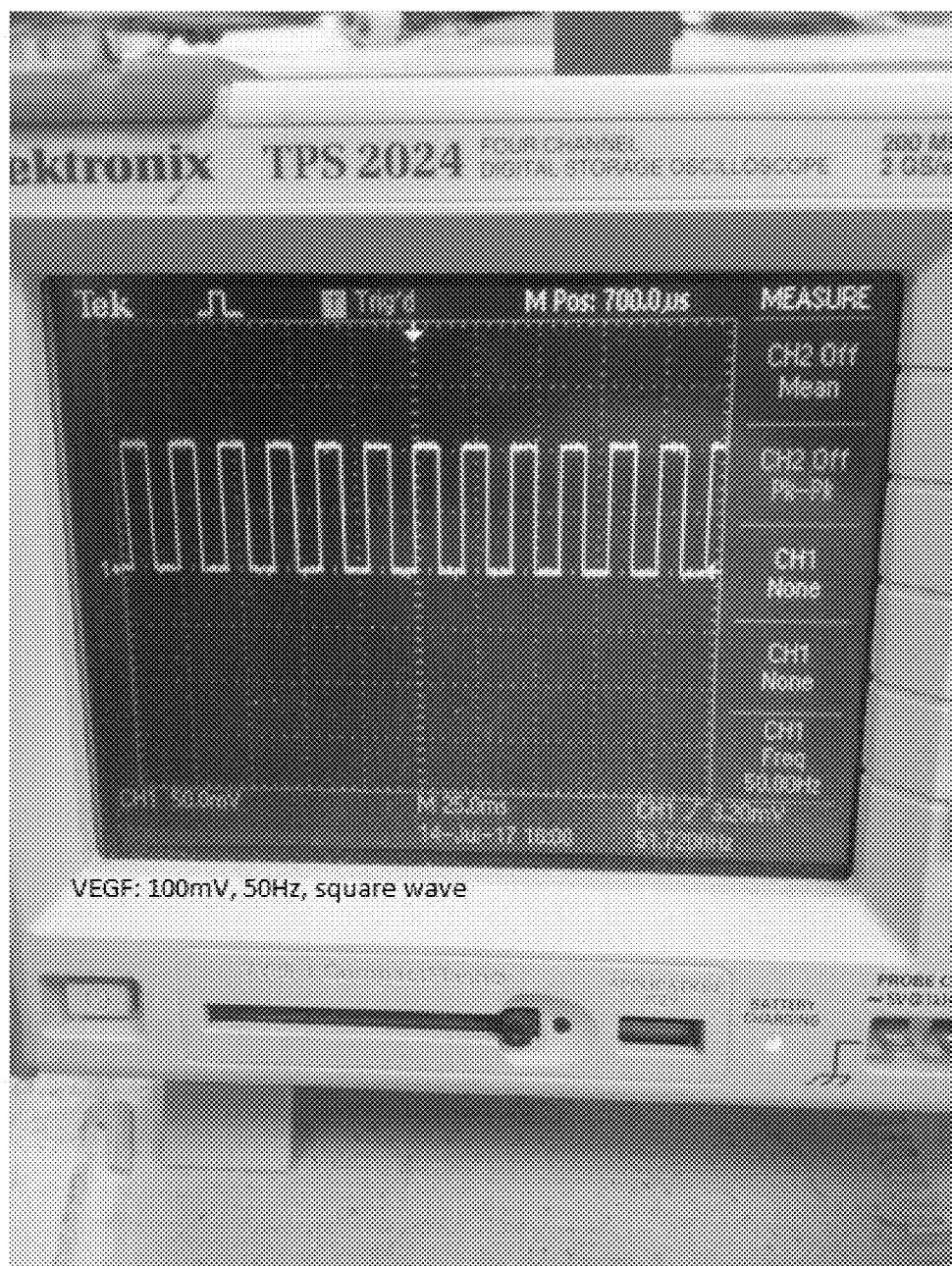
FIG. 19 depicts an image of the signal (voltage and frequency) associated with VEGF: 100 mV, 50 Hz, square wave.
Figure 20:
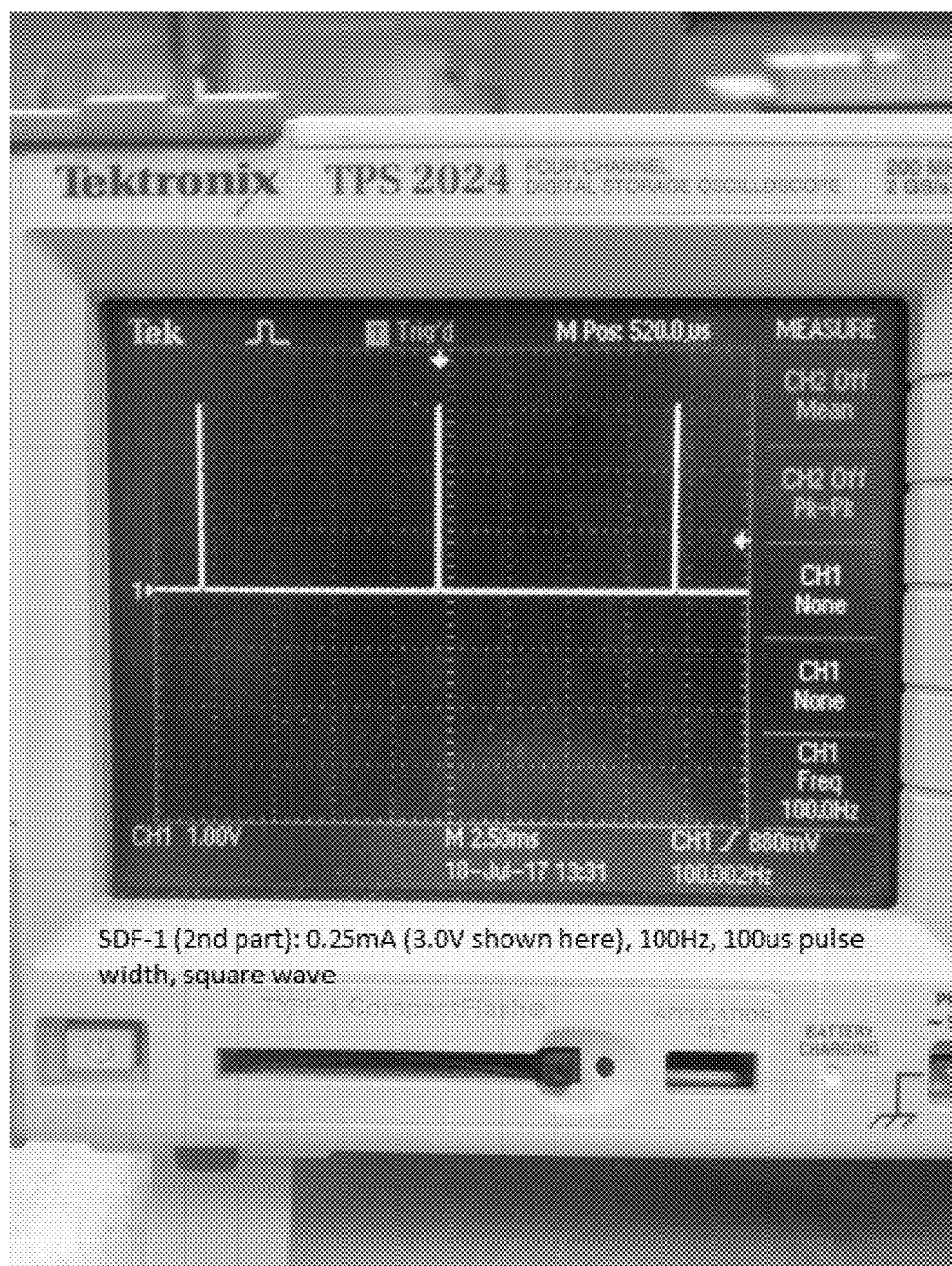
FIG. 20 depicts an image of the signal (voltage and frequency) associated with SDF-1 ($2^{nd}$ part): 0.25 mA (3.0 V shown here), 100 Hz, 100 μs pulse width, square wave.

Specifically, FIG. 6 depicts an image of the signal (voltage and frequency) associated with Activin B at 6.0 mV, pulse width 100 μs, square wave on a TEKTRONIX® TPS 2024 four channel digital storage oscilloscope. FIG. 7 depicts an image of the signal (voltage and frequency) associated with EGF at 10 V/cm (5 V here), 500 Hz, pulse width 180 μs, square wave. FIG. 8 depicts an image of the signal (voltage and frequency) associated with follistatin at 10 V/cm, 50 Hz, square wave. FIG. 9 depicts an image of the signal (voltage and frequency) associated with HGF at 3.5 V, 10 second burst every 30 seconds, square wave. FIG. 10 depicts an image of the signal (voltage and frequency) associated with IGF-1: 3.0 mV, 22 Hz, square wave. FIG. 11 depicts an image of the signal (voltage and frequency) associated with OPG: 4.0 mV, 2,000 Hz, square wave. FIG. 12 depicts an image of the signal (voltage and frequency) associated with PDGF 30%: 3 V/cm (100 mV here), 10 Hz, pulse width 200 μs, square wave. FIG. 13 depicts an image of the signal (voltage and frequency) associated with PDGF 230%: 20 V/cm (7.0 V here), 100 Hz, pulse width 100 μs, square wave. FIG. 14 depicts an image of the signal (voltage and frequency) associated with proliferation: 15 mV, 70 Hz, square wave. FIG. 15 depicts an image of the signal (voltage and frequency) associated with proliferation: 2.5-6.0 V (4V here), 20 Hz, pulse width 200-700 μs, square wave. FIG. 16 depicts an image of the signal (voltage and frequency) associated with RANKL: 3.0 mV, 2 Hz, square wave. FIG. 17 depicts an image of the signal (voltage and frequency) associated with SDF-1: 3.5 mV, 30 Hz, square wave. FIG. 18 depicts an image of the signal (voltage and frequency) associated with tropoelastin: 60 mV, 50 Hz, square wave. FIG. 19 depicts an image of the signal (voltage and frequency) associated with VEGF: 100 mV, 50 Hz, square wave. FIG. 20 depicts an image of the signal (voltage and frequency) associated with SDF-1 ($2^{nd}$ part): 0.25 mA (3.0 V shown here), 100 Hz, 100 μs pulse width, square wave.

In certain embodiments, a subject's organ(s) and/or tissue(s) are first scanned or analyzed with a device to determine what his or her needs may be before treatment begins. The scanning/analysis can be by, e.g., generating mechanical vibrations at position adjacent the location to be an analyzed as described in, e.g., U.S. 2003/0220556 A1 to Porat et al. (the contents of which are incorporated herein by this reference) and/or by measuring transmembrane voltage potential of a cell (see, e.g., Chernet and Levin, "Transmembrane voltage potential is an essential cellular parameter for the detection and control of the cancer tumor development in a *Xenopus* model," *Dis. Models and Mech.* 6, pp. 595-607 (2013); doi:10.1242/dmm.010835, the contents of which are also incorporated herein by this reference. See, also, Brooks et al. "Bioelectric impedance predicts total body water, blood pressure, and heart rate during hemodialysis in children and adolescents," *J. Ren. Nutr.*, 18(3):304-311 (May 2008); doi: 10.1053/j.jrn.2007.11.008, the contents of which are incorporated herein by this reference, describing the use of bioelectric impedance to evaluate the variability of blood pressure, systolic blood pressure, etc.

As used herein, "scanning" means measuring bioelectrical electrical activity of organs, sometimes by placement of a bion coil reader and transmitter in the organ, and direct that information to a computer. The computer stores the bioelectrical read measurements of diseased organs and healthy organs and makes a comparative exam classifying the organ into one category or another, which is much like a doctor using information to make a diagnosis.

Presently, the best approach for whole body and individual organ scanning is to use a combination of: (a) 3D Body Scannint, (b) Quantum Magnetic Resonance Scanning, (c) Biofeedback scanning, (d) Bioelectric scanning, (e) Bion implant scanning, (f) Nervous system scanning, and (g) Light-activated cell reaction reading.

Scanners such as the Ina'Chi scanner, the Quantum Magnetic Resonance Analyzer (QMRA), the 3D Quantum Health Analyzer Scan whole body organ health 2, Body-Scan® scanner, and the "BIONic muscle spindle" are also useful.

See, also, P. Collins "Bioelectric Signals Can Be Used to Detect Early Cancer," *Tufts News*, http://now.tufts.edu/news-releases/bioelectric-signals-used-detect-early-cancer (Feb. 1, 2013) reported that scientists had discovered a bioelectric signal that can identify cells likely to develop into tumors, and that they could lower the incidence of cancerous cells by manipulating the electrical charge across cell membranes. After the subject's needs in this regard are determined, then treatment (e.g., enhanced tissue growth or regeneration) may be initiated as needed and/or desired, preferably with the same device.

U.S. Pat. No. 9,032,964 (May 19, 2015) to Schuler et al., the contents of which are incorporated herein by this reference, describes a scientific computer system with processor capable of recording, storing, and reprogramming the natural electrical signals of cancer cells as found in tumors of humans and animals. The reprogramming process is designed to create a confounding electrical signal for retransmission into a malignant tumor to damage or shutdown the cellular internal electrical communication system. Altering the electrical charge on the glycocalyx of the outer cell membrane is also part of the treatment by application of ions. The system causes cancer cell death as a medical treatment using ultra-low voltage and amperage encoded signals which are reprogrammed from the cancer cell communication signals. The described system causes cancer cell death as a medical treatment. The computer system is used to record and store within a computer processor the resident electrical signals found in cancer cells. Stored data banks of cancer signals recorded from laboratory animals or from animal or human patients are available to study and compare by cancer researchers. Treatment signals likewise are also stored in a computer database for study and as a contribution to developing treatment modalities in cancer patients. The cellular signals are analog in nature and are reprogrammed within the processor to serve as confounding signals and then are saved in another database memory for later transmission into cancer cells as medical therapy. The embodiments shut down or damage the natural electrical signals and the affected processes of cancer cells so as to cause cell death.

For example, the subject is positioned for analysis with a device, preferably with a non-invasive testing device for evaluating, e.g., the autonomic nervous system, organ function(s), and risk factors associated with heart disease, diabetes, and stroke. The non-invasive testing device may analyze data from, e.g., the subject's skin galvanic response, skin color, oximeter, blood pressure, and body composition analyzer to determine hardening and thickening of the subject's arteries, the subject's heart health, exercise capacity, thyroid function, neurotransmitter balance, and multiple other markers for health. See, also, Fatemi et al. "Imaging elastic properties of biological tissues by low-frequency harmonic vibration," *Proceedings of the IEEE*, 91(10):1503-1519 (October 2003).

A method and system for processing cancer cell electrical signals for medical therapy is described in U.S. Pat. No. 8,656,930 to Schuler et al. (Feb. 25, 2014), the contents of the entirety of which is incorporated herein by this reference. In this patent, described is a method of treating cancer by causing apoptosis, comprising the steps of (a) determining a resident electrical signal found in the cancer, (b) modifying the resident electrical signal to form a confounding electrical signal, and (c) applying the confounding electrical signal to the cancer to cause apoptosis. In such a method, the confounding electrical signal is preferably applied with a voltage less than about 2 volts. In such a method, the confounding electrical signal is preferably applied with a voltage is greater than about 0.1 volt. In such a method, the confounding electrical signal is preferably applied with a current less than about 70 micro amps. In such a method, the confounding electrical signal is preferably applied with a current greater than about 2 micro amps. In such a method, the step of applying may have a duration of up to about 4 minutes. However, durations of, e.g., 40 minutes may be alternatively be used.

In an alternative embodiment, the analysis conducted by the device comprises (or further includes) detecting minute energy fields around the human body with, e.g., a "SQUID magnetometer" (SQUID is an acronym for "Superconducting Quantum Interference Device"), able to detect biomagnetic fields associated with physiological activities in the subject's body. A quantum resonant magnetic analyzer analyzes such fields. The magnetic frequency and energy of a subject's organ(s) and/or tissue(s) are collected by appropriately positioning the sensor with respect to the portion of the subject's organ(s) and/or tissue(s) to be analyzed, and after amplification of the signal by the instrument, the data are compared with standard quantum resonant spectrum of diseases, nutrition, and other indicators/markers to determine whether the sample waveforms are irregular using a Fourier approach.

Treatment may include, e.g., moving magnets or changing magnetic fields (pulsed electromagnetic fields) about the tissue and/or organ, for example, to reduce inflammation or treat pain or induce tissue growth in the subject.

The subject's body is scanned to detect non-cancerous tissue damage. When non-cancer damage is detected, treatment may be initiated/indicated/scheduled.

The invention is further described with the aid of the following illustrative Examples.

EXAMPLES

Relationship Between the Components:

The micro voltage signal generator is attached to the pacing infusion lead with, e.g., a corkscrew tip or conductive polymer bandage or patch to the tissue or organ to be treated. An external signal programmer may be used to program the micro voltage signal generator with the proper signals for treatment including the follistatin producing signal. The device battery may be re-chargeable with an external battery charging wand.

In use, the signal generator sends a signal to the target tissue organ that causes the genes within the DNA of that tissue to start the follistatin synthesis process on demand. The signal generator sends a signal to the target tissue organ that causes the genes within the DNA of that tissue to start releasing follistatin on demand. The follistatin -(muscle growth) production signal is preferably 10 V at 50 Hz and 100 Hz, 0.25 mA alternating back and forth. A 3 V signal is being developed.

The system not only controls the DNA to build ribosomes and proteins, but also controls the gates of the cell membranes opening and closing correctly to promote regeneration.

The essential elements are the micro voltage signal generator and the means for delivering the signal to the target tissue.

A micro infusion pump is included to the system for delivering other supportive substances or even follistatin in greater volume more quickly.

The signal generator may be external or internal. The transmission of the signal may be wireless, via liquid and/or via wires.

The tissue contact interface may be a patch or bandage or may be via electrodes or leads.

The described system produces follistatin under precise dosing control at safe and comfortable low voltages.

The signal generator programmed with the follistatin release signal is directed via a lead, bandage of patch to the target organ tissue in need of muscle repair or build up. As the signal is in stimulation mode the tissue releases follistatin and muscle is built or repaired as needed until full function resumes or the desired enhanced function is reached.

Example—Treatment of the Pancreas with Bioelectric Controlled Protein

Treatment of the pancreas with bioelectric controlled protein expression and micro infusion pump stem cell composition delivery.

A pancreas regeneration system includes three primary components. First, the micro bioelectric regeneration stimulator (micro-stimulator from QIG Greatbatch) that controls release of 10 regeneration promoting proteins including SDF-1 a stem cell homing signal, IGF-1, HGF, EGF, activin A and B, eNOS, VEGF, follistatin and tropoelastin. Second, a programmable, re-fillable micro infusion pump. Third, a fifteen component stem cell-based regeneration composition comprising a variety of cell types, growth factors, BMP-7, PDLI-1, HGH, selected alkaloids, micro RNAs, nutrient hydrogel, NADA and pancreatic matrix.

In use, the stimulator and pump are implanted just below the subject's skin with a re-fillable silicone septum port with pacing infusion lead directed to the pancreas with a total conductive infusion wrap tip that is gentle on the pancreatic tissue. One portion of the pacing infusion lead is directed to the interior portion of the pancreas.

Example—Brain and Organ Regeneration Device Based on Bioelectric IGF-1 Stimulation An organ regeneration device that produces controlled release of platelet-derived growth factor by bioelectric stimulation is disclosed. The system provides controlled sustained and repeated release of PDGF via a wire conduction lead or wireless signal delivery and may be combined with a micro infusion pump for maximum results in severe organ failure cases.

A Brain and Organ Regeneration Device based on Bioelectric IGF-1 Stimulation is disclosed. The system directs a lead to exactly the right position with the target organ and stimulates controlled expression of IGF-1 in combination with SDF-1, VEGF, HGH, HGF, Follistatin and tropoelastin in the proper sequence to optimize repair and regeneration.

Damaged aged or cancer stricken organs and tissues are unable to be regenerated back to their original health with current available therapies.

Injections wash away and needle pricks are painful and the entry site is too far away from the organ. Other electrical stimulation devices do not: produce the expression IGF-1 or other combination useful proteins in the most effective sequence.

The disclosed system directs a lead to exactly the right position with the target organ and stimulates controlled expression of IGF-1 in combination with SDF-1, VEGF, HGH, HGF, Follistatin, and tropoelastin in the proper sequence to optimize repair and regeneration.

IGF-1 can transport raw materials to the cells for repair and renovation. IGF-1 promotes raw material transport to the cells. Meanwhile, nucleic acids are helpful in repairing the damage in the DNA, while stimulating cell division. IGF-1 is able to minimize the DNA and cell stellar damage, but also treat the DNA and the cell. The IGF repair cells and thus tissues and organs, especially when delivered over time in combination with other factors such as SDF-1, VEGF, HGH, HGF, follistatin, and tropoelastin.

Controlled on demand expression of IGF-1 can help repair cells, tissues and organs including brain, muscle, pancreas, lung, skin, kidney and liver.

IGF-1 injections and infusions do not get enough repair material to the target organ or tissue and cause inflammation, which is counterproductive to regeneration. Thus electrical stimulation is preferred. Prior art electrical stimulation systems failed to express the right regenerative proteins at the right time.

The system directs a lead to exactly the right position with the target organ and stimulates controlled expression of IGF-1 in combination with SDF-1, VEGF, HGH, HGF, Follistatin, and tropoelastin in the proper sequence to optimize repair and regeneration. Also, it can produce hearts, kidneys, livers, lungs, brains, pancreas, lung, skin, knees, and elbows, skin, penis, breasts, aorta, arteries, and limbs.

The version of the system discussed for this Example includes the following components: bioelectric regeneration stimulator (micro-stimulator from QIG Greatbatch); signal for causing controlled release of IGF-1: applied 20V at 1 Hz with a frequency of 5 ms for 24 hours; signal for causing controlled release of SDF-1; signal for causing controlled release of VEGF; signal for causing controlled release of HGH; signal for controlled release of HGF; signal for controlled release of follistatin; signal for controlled release of tropoelastin; pacing infusion lead to implant in organ or tissue to be treated; infusion and electrode wide area patch (optional); wireless transmitter for all signals listed above (optional); refillable micro pump (optional); external programmer; and external battery charger.

The regeneration stimulator may be implanted just below the skin of the patient or may be external, especially if the wireless option is chosen. For the implantable model, an infusion conduction lead is directed from the stimulator to the organ or tissue to be repaired. The tip of the lead is lodged into the tissue with a corkscrew or other fixation tip. The regeneration stimulator is programmed by an external programmer. The stimulator is programmed to cause release of specific regeneration proteins in a preferred sequence to optimize organ repair starting with VEGF, then SDF-1, then IGF-1, then HGH, then HGF, then follistatin, then tropoelastin. The wireless version is applied externally with the signal pointed to the organ to be regenerated. The signal may be constantly calibrated to adjust for fat, skin, and other obstacles between the signal generator and the organ of Interest to be treated. The device may be recharged with an external charger. In cases of very widespread organ damage, a wide array infusion and electrode patch may be used to cover the damaged organ area more completely. To accelerate the organ regeneration, an implantable, programmable, refillable micro infusion pump may be used to deliver various stem cells, nutrient hydrogels Micro RNA's and growth factors and (in some cases) drugs.

SDF-1 recruits via homing signal new reparative stem cells to the damaged organ, VEGF causes new nutrient and oxygen producing blood vessels to grow into the area being treated and increasing local oxidation in a beneficial way (e.g., high oxidation is a signal for p53 activation in cancer cell apoptosis in different systems such as pancreas cancer cells). IGF-1 repairs damaged cells, tissues and organs. Follistatin repairs damaged muscle. Tropoelastin adds elasticity to treated tissues making them more compliant. HGF aides in all repair processes and in the specific case of heart regeneration, reduces the risk of arrhythmias. All of these proteins work together to fully regenerate an organ over time. The process am be accelerated with the use of a micro infusion pump that is filled with various types of stem cells and growth factors and in some cases drugs.

The construction of electric signal generators, and pacemakers, are known to the art and can be obtained from OEM suppliers as well as their accompanying chargers and programmers. What is unique is the programming of specific signals to use specific protein expressions at precisely the right time for optimal organ regeneration. Pacing infusion leads may be purchased from a variety of OEM vendors. An infusion and electrode wide area pitch may be constructed by cutting conduction polymer to shape and forming plastic into a flat bag with outlet ports in strategic locations.

Any one of the protein expression signals work well on their own for organ regeneration, but they work better together. As previously identified herein, SDF-1 is the most powerful regeneration protein followed by IGF-1.

A wireless, single lumen infusion pacing lead or infusion conduction wide array patch may all be used to deliver the regeneration signals and substances to the organ of interest to be treated or they may be used in combination.

A bionic neuron ("BION") device (injectable microstimulator) may be adapted to provide the requisite stimulation. Such a device is typically the size of a long grain of rice (2 mm wide by 15 mm long) and comprises an integrated circuit chip sandwiched inside an antenna coil.

The regeneration stimulator lead or wireless signal is directed to the organ to be regenerated and the protein signals are delivered. Again, the most important is SDF-1 which recruits new stem cells to the site and its accompanying reverse polarity signal which triggers differentiation of the recruited stem cells into useful tissues.

The second most important is IGF-1, which is highly potent in cell repair. VE'GF helps grow in blood vessels for feeding the newly created and newly regenerated tissues.

Example—PDGF

Described herein is the bioelectric controlled expression of platelet derived growth factor (PDGF). PDGF is a powerful organ regeneration protein/cytokine. PDGF is one of the most potent growth factors in promoting cell, tissue and organ repair applicable to a wide variety of uses. It has been demonstrated to be especially useful in heart regeneration.

Described is the precise bioelectric signal for triggering PDGF expression from tissues. PDGF combined with the programmable micro-infusion pump and fifteen component organ regeneration composition is to help patients with degenerating and diseased organs to recover. Both wireless non-invasive and implantable wire lead based means may be utilized to get the regeneration and healing promoting bioelectric signals to organs.

PDGF constitute a family of four gene products (PDGF-A-D) acting by means of two receptor tyrosine kinases, PDGFRα and β. Three of the ligands (PDGF-A, PDGF-B, and PDGF-C) bind to PDGFRα with high affinity. PDGF signaling is essential for epicardial cell proliferation. PDGF signaling plays important roles in coronary vessel formation.

PDGF also induces DNA synthesis in cardiomyocytes. PDGF recruits stem/progenitor cells. PDGF can trigger controlled cell proliferation. PDGF can contribute to cell reprogramming and transformation into induced multipotent stem cells. PDGF downstream effects include regulation of gene expression and the cell cycle. PDGF can be used to create cell-specific antifibrotic compounds including those needed for liver regeneration. PDGFs are required for normal kidney development via recruitment of mesenchymal cells to both glomeruli and the interstitium. PDGF exerts essential roles from the gastrulation period to adult neuronal maintenance by contributing to the regulation of development of preplacodal progenitors, placodal ectoderm, and neural crest cells to adult neural progenitors, in coordinating with other factors. PDGF plays critical roles for maintenance of many specific cell types in the nervous system together with vascular cells through controlling the blood brain barrier homeostasis. PDGF modulates neuronal excitability through adjusting various ion channels, and affecting synaptic plasticity and function. PDGF stimulates survival signals, majorly PI3-K/Akt pathway but also other ways, rescuing cells from apoptosis. PDGF in dendrite spine morphology is critical for memory in the developing brain. PDGF has been found to stimulate regeneration of periodontal tissues and bone. PDGF has been found to highly stimulate hair regeneration. PDGF signaling is essential in regeneration of hearts in animals. PDGF signaling induces DNA synthesis in the cells and is required for cardiomyocyte proliferation during heart regeneration. PDGF was used in biological pacemaker development, and it worked well to help form new sino atrial node cells from atrial myocytes. PDGF has been found useful in regeneration of other organs such as eyes, lungs, kidneys, brains, hair and aortas.

Described is an organ regeneration device that produces controlled release of PDGF by bioelectric stimulation. Failing organs cannot produce enough PDGF to fully regenerate.

Other devices only provide one time delivery of PDGF, which is insufficient to fully regenerate a failing organ. Infusion systems lose too much therapeutic agent.

The system provided herein provides controlled sustained and repeated delivery of PDGF via a wire conduction lead or wireless signal delivery and may be combined with a micro infusion pump for maximum results in severe organ failure cases.

The bioelectric stimulator preferably reads the needs of an organ and produces release of PDGF in just needed amounts to enhance organ regeneration. Researchers previously conducted organ regeneration studies of one time injection of PDGF with a needle and syringe. This is impractical and will not work for major organ repair.

A onetime dose is not enough to fully regenerate an organ. To access the organ with a needle and syringe is very invasive, dangerous and painful. Injected or infused PDGF has a high wash out loss rate.

The system provides controlled sustained and repeated release of PDGF via, e.g., a wire conduction lead or wireless signal delivery and may be combined with a micro infusion pump for maximum results in severe organ failure cases.

Also, it can produce the device may also be used for organ enhancement instead of just organ repair such as brain function enhancement.

The version of the system discussed for this Example includes the following components: micro bioelectric signal generator; programming wand; programming computer; pacing infusion lead; micro infusion pump; PDGF bioelectric signal program; PDGF solution; organ reading device and processor; organ reading software program and analysis software; and wireless energy beam transmitter.

Relationship Between the Components:

The micro bioelectric stimulator is programmed with the programming wand connected to the programming computer with the PDGF bioelectric signal of 20 V, 50 Hz, and 0.2 amps. The micro stimulator is connected to the pacing infusion lead and the other side of that lead is affixed in the central portion of the damaged or diseased target organ. The programming wand connected to the programming computer can active the micro bioelectric stimulator to become an organ reading device. When programmed with the organ reading and analysis software the organ reader is able to read all the bioelectric activity of the failing organ as well as its phenotype, genotype including genetic defects and variation and chemical and biologically metabolism.

The bioelectric stimulation controlled PDGF expression causing new blood vessels to grow into the failing organ(s) and new healthy organ tissue to form. The reader adjusts the therapeutic dose as needed. The micro infusion pump re-filled daily with a mixed stem cell based composition that includes PDGF and may also include SDF-1, IGF, EGF, HGF, HGH, Activin A and B, eNOS, VEGF, follistatin, tropoelastin. GDF-10, GDF-11 and Neurogenin-3, selected alkaloids, and selected anti-inflammatory factors may be used to supplement the bioelectric stimulation therapy for organ repair in seriously failing organs.

If the organ failure is severe, an added programmable, implantable, re-fillable micro infusion pump may be added to the therapy. The micro pump is refilled daily with about 2 ml of stem cell-based organ regeneration composition that includes PDGF. If it is not easy or desirable to reach the organ to be treated with a wire-based pacing infusion lead, the operator may utilize a wireless energy beam transmitter to deliver the bioelectric regeneration signals wirelessly to the organ.

In this embodiment, the stimulator, lead, and programmer are essential. The micro infusion pump and mixed organ regeneration composition are optional.

The micro stimulator, and if chosen, the micro infusion pump are implanted somewhere below the skin of the patient with the pump silicone septum ports accessible for re-filling just below the skin. The stimulator must be in a location reachable by the programming wand attached to a portable computer. The pacing infusion lead form the stimulator and pump is directed to the central damaged portion of the damaged organ i.e., heart, kidney, pancreas, liver. The micro stimulator may optionally be non-invasive and external and can deliver its signal to the failing organ via a focalized wireless energy beam. Much like how they focalize radiation to treat cancer tumors, but this energy stimulates organ regeneration.

Additionally: The micro stimulator may be programmed for additional protein expressions. The micro pump may be used a stand-alone device. The sequence of use may be changed.

The device may also be used for organ enhancement instead of just organ repair such as brain function enhancement.

Two PDGF expression control signals. One low voltage and one higher voltage.

The test tissue is sheep heart tissue, while the test cells are mesenchymal stem cells. 30% PDGF increase with 3 V/cm, 10 Hz, 2 micro amps (0.000002 amps) and the pulse duration 0.2 ms. 230% PDGF increase with 20 V/cm 100 Hz, 0.25 mA ($2.5e^{-7}$ amps) and pulse duration of 40 pulses/s, width of 100 μs.

Example—Treating Cancer Tumors Using Bioelectric Stimulation in Combination with Micro Infusion Previous cancer treatments failed to address the combination of stopping cell proliferation and blood supply followed by regenerating the damaged tissue or organ.

Cytokine and Chemotherapeutic and regenerative treatment for certain cancers may be combined with low intensity, intermediate frequency alternating electric fields that are tuned to release specific beneficial proteins at specific time intervals. More specifically, cell proliferation inhibition and halting blood supply to tumors in the first treatment stage. The bioelectric stimulation treatment may be increased in volume and efficacy by the combination use of an implantable, programmable, re-fillable micro infusion pump that delivers anti-cell proliferation and anti-blood vessel growth proteins as well, if desired, standard cancer treatment drugs such as chemo therapy agents. The second stage of treatment is focused regeneration of cancer damaged tissues back to their most optimal healthy state. The regenerative phase comprises a sequence of recruiting reparative stem cells to the damaged organ by bioelectrically stimulating the release of SDF-1 (stem cell homing factor), followed by a controlled proliferation signal, a controlled blood vessel supply signal (VEGF) and if desired and useful release of Follistatin, tropoelastin, HGF, IGF-1 and Activin. The stimulation cycle causing release of beneficial proteins for regeneration may be upgraded in volume and speed of delivery by the combination use of an implantable, re-fillable, programmable micro infusion pump for delivering a higher quantity of stem cells, nutrient hydrogel, matrix and beneficial tissue and organ regeneration promotion proteins.

Cytokine and Chemotherapeutic and regenerative treatment for certain cancers comprising a combination low intensity, intermediate frequency alternating electric fields that are tuned to release particular beneficial proteins in two stages, stage (1) is stopping cancer spread by halting cell proliferation and halting tumor blood supply and stage (2) regenerating the cancer damaged tissue or organ back to optimal health. In many cases, the resulting cell proliferation inhibition is significantly higher than the inhibition obtained by drug-only regimens of treatment.

A method of killing or inhibiting the growth of cancer cells in a target region followed by regenerating the tissue or organ back to optimal health, the method comprising the steps of:

Stage 1=Stop Cancer Growth by:

Applying, to the target region, a series of bioelectric signals that damages the cancer cells or inhibits the growth of the cancer cells via stopping cell proliferation and halting blood supply temporarily, but leaves normal cells in the target region substantially unharmed; and Treating the cancer cells with another anti-cancer regimen via programmable micro pump infusion, wherein the applying step and the treating step are performed simultaneously.

Stage 2=Regeneration of Post-Cancer Tissue or Organ by:

Treating the target region with a series of bioelectric signals to recruit stem cells, grow healthy blood vessels and re-grow healthy functional tissues in the previous cancer damaged region In such a method, in the applying step, the field may be applied in at least two different directions in an alternating sequence to halt cell proliferation and to stop blood supply to the cancer tumor.

In such a method, the other anti-cancer regimen may comprise treating the cancer cells with an anti-cancer drug. In this method, the drug may comprise at least one drug selected from the group consisting of paclitaxel, doxorubicin cyclophosphamide, and cisplatin. In such a case, the drug dosage may be less than 20% of a standard dosage for the drug.

In such a method, the bioelectric stimulation may release any one of these regeneration of tissue and organ beneficial proteins SDF-1, IGF-1, Activin, HGF, VEGF, Follistatin or tropoelastin and in specific sequences for optimal organ health.

In such a method, all bioelectric regeneration signal may be delivered wirelessly and/or non-invasively.

In such a method, the target cancer may be breast cancer and the target regenerative organ may be breast reconstruction.

In such a method, the target cancer may be brain cancer and the target regenerative organ is brain.

In such a method, the target cancer may be prostate cancer and the target regenerative organ may be the prostate.

In such a method, the target cancer may be colon cancer and the target regenerative organ may be the colon.

In such a method, the target cancer may be throat or esophageal cancer and the target regenerative organ may be throat or esophagus.

In such a method, the target cancer may be pancreas cancer and the target regenerative organ may be the pancreas with improved insulin production.

In such a method, the target cancer may be lung cancer and the target regenerative organ may be lung(s).

In such a method, the target cancer may be eye cancer and the target regenerative organ may be the eye.

Example

In bioelectric stimulation tissue studies, a 2000% increase in IL-6 was achieved. IL-6 is a key promoter of regeneration. With respect to IL-6, Mosteiro et al. (2016) shows that tissue damage is a relevant factor for cells to go back to an embryonic state. Nobel Prize winner Shinya Yamanaka opened the door to regenerative medicine by cell reprogramming, based on introducing a combination of four genes known as OSKM (for genes, OCT4, SOX2, KLF4, and MYC), which reverts adult cells to an embryonic-like state, and transforms these cells into pluripotent cells. Cell reprogramming was later achieved within a living organism (i.e., a mouse) in 2013.

Mosteiro et al. (2016) analyzes what happens in living tissues when reprogramming is induced using OSKM. OSKM was found to be inefficient at inducing reprogramming or pluripotency in the highly specialized cells that constitute adult tissues. Tissue damage plays a critical role by complementing the activity of the OSKM genes.

This relationship between damage and reprogramming is mediated by the proinflammatory molecule, interleukin-6 (IL-6). Without IL-6 presence, the OSKM genes are far less efficient at inducing the reprogramming process. These findings suggest the following sequence of events: the expression of the OSKM genes results in damage to the cells; accordingly, they secrete IL-6; the presence of this molecule induces the reprogramming of some neighboring cells.

Both wireless non-invasive and/or implantable wire lead ("electrode") based means may be used to deliver the regeneration and healing promoting bioelectric signals to target organs.

The controlled expression of Hypoxia Inducible Factor 1 ("HIF-1α") for, e.g., promoting organ regeneration (particularly liver regeneration) is also described herein. HIF-1α is a powerful organ regeneration protein. A more than 286% increase of HIF-1α on demand in test article tissues was achieved with a specific, optimized bioelectric signal. In other experiments, a 2300% increase in expression of HIF-1α was achieved.

Hypoxia has been proven as a critical element in the organ regeneration process. HIF-1α is a master regulator of the adaptive response to hypoxia. HIF-1α over expression in cells mimics the mechanisms triggered by hypoxia in injured or diseased tissues and increases their therapeutic potential without direct hypoxia stimulation.

Potential useful properties of HIF-1α for organ regeneration include: HIF-1α signaling promotes heart regeneration, HIF-1α signaling reduces infarction size and attenuates cardiac dysfunction, HIF-1α induces coronary collateral vessel formation, HIF-1α is a cancer tumor suppressor, HIF-1α has been reported a gateway controller of cancer, HIF-1α promotes liver regeneration, HIF-1a promotes lung regeneration via alveolar development, HIF-1α promotes brain saving following traumatic brain injury or stroke, HIF-1α promotes retinal eye regeneration, HIF-1α management seems to be important to healthy kidney function and can protect against kidney injury, HIF-1α helps promote muscle regeneration, HIF-1α helps promote wound healing, HIF-1α has a supportive role in hair regeneration, HIF-1α promotes extracellular matrix, HIF-1α has a critical role in bone development and healing, HIF-1α may be important to stabilize teeth positions after accelerated tooth movement, and HIF-1α is an essential regulator of inflammation.

Example

Prospective, randomized, blinded, and placebo-controlled study of multi-stage bioelectric therapy for cancer tumor treatment in a murine glioma xenograft model In this study, we will measure the effects of a multi-stage bioelectric therapy on a murine xenograft model of cancer to determine the optimal parameters using this approach.

Bioluminescence imaging (BLI) and caliper measurements will be used to track tumor growth from two weeks post-inoculation of cancerous cells to four weeks post-inoculation. We expect a significant decrease in tumor size in the treatment condition when compared to the sham condition. Results showing a decrease in tumor size in the treatment arm will provide important evidence moving forward to determine optimal frequency and tuning parameters of multi-stage bioelectric therapy.

Brain imaging studies are performed in order to show the presence, size, and location of the glioblastoma GBM. The most common brain imaging study used in the diagnosis of GBM is gadolinium-enhanced magnetic resonance imaging (MRI). GBM is most visible in T1-weighted MRIs and differences between white and gray matters are visible because of changes in contrast.

The described multi-stage bioelectric therapy comprises: bioelectric and cytokine reading of the cancer tumor, customized jamming of communications within the cancer tumor, reducing blood supply to the cancer tumor to starve it, changing surface proteins and electrical charge of the cancer tumor so that the patient's own immune system attacks the cancer tumor ("immunotherapy"), stopping cell division in and around the cancer tumor, managing and modulating inflammation in the subject, particularly in and around the cancer tumor, and encouraging stem cell and protein expression based organ regeneration.

Materials

Mouse Strain.

NSG NOD scid gamma (00557) will be acquired from Jackson Laboratory, shipped to University, and then allowed to acclimate for three to seven days in the animal facility prior onset of experimental procedures.

Cancer Cell Line.

Bioware Brite Cell Line—GL261 Red-FLuc. Codon-optimized luciferase from Luciola Italica (RedLuc) with a red-shifted emission peak wavelength of 617 nm (as compared to 550 nm [Luc] and 590 nm [Luc2]) and approximately 100-fold higher signal intensity compared to the other firefly luciferases.

Tumor Model.

An Ectopic tumor xenograft model will be used with subcutaneous injection of cells into the flank of the rodent. Subjects will be inoculated with cancer cells shortly after arrival at University.

Bioelectric Stimulation.

The proposed treatment (FIG. 1) will be applied by means of pairs of wires/electrodes with leads, which will be placed intradermally on the back of a mouse. Tumors will be inoculated intradermally in between the pair of implanted wires/electrodes with a separation of millimeters between the pairs. A signal generator coupled with a voltage amplifier is set to apply electrical stimulation via the wire/electrode pair to tumors. Mice in the sham (control group) will have the wire/electrode setup, but will not receive therapy. Mettler, Rigol, or other suitable stimulator will be used for the study.

Procedure

Schedule.

The study will begin approximately 14 days post-inoculation of cancerous cells. Expected tumor size will be approximately 400 mm3 based on growth rate curves from validation studies.

Day 0: Mice arrive from Jackson Labs
Day 3: Mice engrafted with tumor cells at University
Day 17: Bioluminescence imaging; caliper measurement
Day 17: Treatment/sham 40 minutes
Day 20: Bioluminescence imaging; caliper measurement
Day 20: Treatment/sham 40 minutes
Day 24: Bioluminescence imaging; caliper measurement
Day 24: Treatment/sham 40 minutes
Day 27: Bioluminescence imaging; caliper measurement
Day 27: Treatment/sham 40 minutes
Day 31: Bioluminescence imaging; caliper measurement All possible efforts will be made to minimize animals' suffering and the number of animals used. All experimental procedures will be conducted under the guidelines set forth by the UNIVERSITY and IACUC.

Outcome Measures

Bioluminescence.

Over the past decade, in vivo bioluminescent imaging has emerged as a non-invasive and sensitive tool for studying ongoing biological processes within living organisms. Based on the detection and quantitation of the photons produced by the oxidation of luciferin by luciferase enzymes, this technique has proved to be particularly useful in analyzing cancerous cells and monitoring tumor growth, providing a cost-effective insight into how the disease progresses in vivo, without the need of serial sacrifice of animals. Bioluminescence will be utilized in this study providing (1) the biodistribution of antibodies, (2) the distribution of immune cells in tumor-bearing animals, (3) quantification of cancer-related biomarkers, and (4) size and location of the cancer tumors. The luminescence, which is the consequence of the photon flux emitted by the luciferase-expressing cells, directly correlates to the size of the cancer tumor and can be measured at the site of injection using a region of interest (ROI) tool.

Caliper Measurement.

To determine tumor volume by external caliper, the greatest longitudinal diameter (length) and the greatest transverse diameter (width) were determined. Tumor volume based on caliper measurements were calculated by the modified ellipsoidal formula.

REFERENCES (The contents of the entirety of each of which is incorporated herein by this reference.)

Beebe et al. "Bioelectric Applications for Treatment of Melanoma," Cancers (Basel). 2010 September; 2(3): 1731-1770, published online 2010 Sep. 27; doi: 10.3390/cancers20317

B. Borgobello "FDA approves the treatment of brain tumors with electrical fields," New Atlas, http://newatlas.com/treatment-of-brain-tumors-with-electrical-fields/21433/ (Feb. 13, 2012).

"Cancer reversed in frogs by hacking cells' electricity with light," New Scientist This Week, 16 Mar. 2016.

J. Cervera "The interplay between genetic and bioelectrical signaling permits a spatial regionalisation of membrane potentials in model multicellular ensembles," Nature, Scientific Reports, 12 Oct. 2016 volume 6, Article number: 35201 (2016).

Chernet, B., and Levin, M. (2014). Transmembrane voltage potential of somatic cells controls oncogene-mediated tumorigenesis at long-range. Oncotarget, 5 (May 1, 2014).

Dai et al. "Nanosecond Pulsed Electric Fields Enhance the Anti-tumour Effects of the mTOR Inhibitor Everolimus against Melanoma," Scientific Reports volume 7, Article number: 39597 (2017).

"Electric Tumor Treatment Fields," No. 0827 Policy, aetna.com/cpb/medical/data/800_899/0827.html (Nov. 18, 2016).

Fatemi et al. "Imaging elastic properties of biological tissues by low-frequency harmonic vibration," Proceedings of the IEEE, 91(10):1503-1519 (October 2003) DOI: 10.1109/JPROC0.20030.817865.

D. Grady "Electrical Scalp Device Can Slow Progression of Deadly Brain Tumors," New York Times, https://www.nytimes.com/2014/11/16/health/electrical-scalp-device-can-slow-progression-of-deadly-brain-tumors.html?_r=0 (Nov. 15, 2014).

J. Hamzelou "Bioelectric cancer hack," New Scientist, Volume 229, Issue 3065, 19 Mar. 2016, Page 8.

W. Hoffmann "Regeneration of the gastric mucosa and its glands from stem cells," Curr. Med. Chem, 15(29):3133-44 (2008).

Keunen et al. "Anti-VEGF treatment reduces blood supply and increases tumor cell invasion in glioblastoma," Proc. Natl. Acad. Sci. U.S.A. 2011 Mar. 1; 108(9): 3749-3754, published online 2011 Feb. 14; doi: 10.1073/pnas.1014480108.

Lanzetto et al. "Fundamental principles of an anti-VEGF treatment regimen: optimal application of intravitreal anti-vascular endothelial growth factor therapy of macular diseases," Graefes Arch. Clin. Exp. Ophthalmol. 2017; 255(7): 1259-1273 (published online 2017 May 19); doi: 10.1007/s00417-017-3647-4

Meadows et al. "Anti-VEGF Therapies in the Clinic," Cold Spring Harb. Perspect. Med. 2012 October; 2(10): a006577: doi: 10.1101/cshperspect.a006577.

A. Mishra "Angiogenic neovessels promote tissue hypoxia," Proc. Natl. Acad. Sci. U.S.A. 2016 Sep. 20; 113(38): 10458-10460, published online 2016 Sep. 13; doi: 10.1073/pnas.1612427113.

Mosteiro et al. "Tissue damage and senescence provide critical signals for cellular reprogramming in vivo," Science, 2016; 354 (6315): aaf4445 DOI: 10.1126/science.aaf4445.

Puro et al. "Bioelectric impact of pathological angiogenesis on vascular function," *PNAS* Aug. 30, 2016 113 (35) 9934-9939; published ahead of print Aug. 22, 2016 https://doi.org/10.1073/pnas.1604757113.

Silvers et al. "The Bioelectric Code: Reprogramming Cancer and Aging from the Interface of Mechanical and Chemical Microenvironments," *Front. Cell Dev. Biol.*, 6 Mar. 2018; doi.org/10.3389/fcell.2018.00021.

Tajima et al. "HIF-1αlpha is necessary to support gluconeogenesis during liver regeneration," *Biochem. Biophys. Res. Commun.* 2009 Oct. 2; 387(4):789-94. doi: 10.1016/j.bbrc.2009.07.115. Epub 2009 Jul. 28.

What is claimed is:

1. A method of treating a subject having a cancer tumor, the method comprising:
   reading the cancer tumor real time; and
   custom delivering individualized bioelectric therapy comprising at least one bioelectric signal to the subject and/or the cancer tumor in response to the reading,
   wherein the bioelectric therapy acts to starve the cancer tumor of blood supply and alter the cancer tumor's surface proteins and/or surface charge so that the subject's immune system attacks the cancer tumor.

2. The method according to claim 1, wherein the individualized bioelectric therapy is delivered to the subject and/or the cancer tumor by a device comprising:
   a probe for determining a resident electrical signal found in the cancer tumor;
   a computer system comprising a processor for modifying each determined resident electrical signal to form at least one confounding electrical signal unique to each determined resident electrical signal, and data storage for storing all confounding electrical signals; and
   a probe for applying the confounding electrical signal(s) to the cancer tumor.

3. The method according to claim 2, wherein the computer system utilizes a data base including a bioelectrical signal read profile of healthy organs and is adapted to distinguish when an organ is affected by a cancer tumor as being different than a healthy normal organ.

4. The method according to claim 1, further comprising:
   re-reading the cancer tumor after delivery of the individualized bioelectric therapy; and
   delivering revised individualized bioelectric therapy to jam communication signaling within the cancer tumor based upon changes in communication patterns of the cancer tumor after the custom delivery of the individualized bioelectric therapy.

5. The method according to claim 4, wherein jamming of communication of the cancer tumor occurs by application of two frequencies in succession, wherein the first frequency is 200 kHz±10% and the second frequency is 300 kHz±10% alternating in bursts back and forth, and wherein the amplitude is at least 0.6 V/cm root mean square ("RMS").

6. The method according to claim 1, wherein the bioelectric therapy includes a bioelectric signal comprising: 1 Hz, pulse width 5 milliseconds.

7. The method according to claim 6, wherein the bioelectric signal comprises:
   10 to 20 V pulse width 5 milliseconds, 1 Hz, for 3 to 24 hours.

8. The method according to claim 1, further comprising applying resonance signals to the cancer tumor so as to burst cells in the cancer tumor.

9. The method according to claim 1, further comprising a real time read bioelectric modulation of inflammation.

10. The method according to claim 1, further comprising applying at least one bioelectric signal to the subject so as to increase concentration of at least one protein about the cancer tumor.

11. The method according to claim 1, further comprising administering to the subject an infusion of a composition comprising stem cells.

12. The method according to claim 1, wherein reading the cancer tumor real time comprises utilizing an implantable and/or wireless external, chronic, closed-loop neuromodulation device with concurrent sensing and stimulation.

13. The method according to claim 1, further comprising applying to the cancer tumor a bioelectric signal of 30 Hz, square wave and/or a bioelectric signal of 100 Hz, 100 μs pulse width, square wave.

14. The method according to claim 1, wherein at least one bioelectric signal manages inflammation in the subject.

15. The method according to claim 1, wherein the bioelectric signals re-program cancer tumor cells to be non-cancerous.

16. The method according to claim 1, wherein the bioelectric therapy includes bioelectric signals comprising:
   first, 300 ns, 1.8-7 kV/cm, 50-700 pulses and, second, 300 ns pulses with a threshold of greater than 20 kV/cm and an effective electric field of 40 kV/cm.

17. The method according to claim 1, wherein the bioelectric therapy includes a bioelectric signal having a voltage of from greater than 0.1 volts to less than about 2 volts, and a current greater than 2 micro amps, but less than about 70 micro amps, and wherein said bioelectric signal is applied for a duration of about 4 minutes.

18. A method for treating a subject with a cancer tumor, the method comprising:
   bioelectrically scanning the cancer tumor;
   reading and analyzing the cancer tumor to determine electrical communications within the cancer tumor;
   delivering communication jamming signals to the cancer tumor to stop said electrical communications within the cancer tumor;
   applying a bioelectrical signal sequence to the cancer tumor that stops cell division in the cancer tumor;
   applying a bioelectrical signal sequence about the cancer tumor so as to starve the cancer tumor of blood supply;
   analyzing surface protein expression on the cancer tumor; and
   delivering bioelectric signals to the cancer tumor to change the surface protein expression on the cancer tumor so that the subject's immune system attacks the cancer tumor as an enemy.

19. The method according to claim 18, further comprising:
   providing immuno-response therapy to the subject.

20. The method according to claim 18, further comprising:
   applying an organ regeneration sequence to recover an organ affected by the cancer tumor.

* * * * *